US007217789B2

(12) United States Patent
Fradkov et al.

(10) Patent No.: US 7,217,789 B2
(45) Date of Patent: *May 15, 2007

(54) FLUORESCENT TIMER PROTEINS AND METHODS FOR THEIR USE

(75) Inventors: Arcady Fedorovich Fradkov, Moscow (RU); Alexey Terskikh, Santa Clara, CA (US)

(73) Assignee: Clontech Laboratories, Inc., Mountain View, CA (US)

( * ) Notice: Subject to any disclaimer, the term of this patent is extended or adjusted under 35 U.S.C. 154(b) by 464 days.

This patent is subject to a terminal disclaimer.

(21) Appl. No.: 10/315,920

(22) Filed: Dec. 9, 2002

(65) Prior Publication Data

US 2003/0175809 A1    Sep. 18, 2003

Related U.S. Application Data

(63) Continuation-in-part of application No. PCT/US01/19097, filed on Jun. 13, 2001.

(60) Provisional application No. 60/211,607, filed on Jun. 14, 2000.

(51) Int. Cl.
| | |
|---|---|
| *C07K 14/435* | (2006.01) |
| *C12N 15/12* | (2006.01) |
| *C12N 15/79* | (2006.01) |
| *G01N 21/64* | (2006.01) |
| *C12Q 1/68* | (2006.01) |

(52) U.S. Cl. .................. 530/350; 435/6; 435/69.1; 435/252.3; 435/320.1; 536/23.5; 436/164

(58) Field of Classification Search .............. None
See application file for complete search history.

(56) References Cited

U.S. PATENT DOCUMENTS

| | | | | |
|---|---|---|---|---|
| 6,969,597 B2* | 11/2005 | Lukyanov et al. | ......... | 435/69.1 |
| 2002/0160473 A1* | 10/2002 | Lukyanov et al. | .......... | 435/183 |
| 2002/0197676 A1* | 12/2002 | Lukyanov et al. | ......... | 435/69.1 |
| 2004/0171107 A1* | 9/2004 | Nelson et al. | ............. | 435/69.1 |
| 2005/0032085 A1* | 2/2005 | Labas et al. | ................... | 435/6 |
| 2006/0035330 A1* | 2/2006 | Lukyanov et al. | ......... | 435/69.1 |

FOREIGN PATENT DOCUMENTS

WO    WO 00/34326    6/2000

OTHER PUBLICATIONS

Baird et al. Biochemistry, mutagenesis and oligomerization of Dsred, a red fluorescent protein from coral. Oct. 24, 2000. Proc. Natl. Acad. Sci., USA 97 (22) :11984-11989.*

(Continued)

*Primary Examiner*—Nashaat T. Nashed
*Assistant Examiner*—William W. Moore
(74) *Attorney, Agent, or Firm*—Bret E. Field; Bozicevic, Field & Francis LLP

(57) ABSTRACT

Fluorescent timer proteins, which undergo a spectral shift over time after synthesis, as well as nucleic acid compositions encoding the same, are provided. Also provided are fragments of the subject proteins and nucleic acids encoding the same, as well as antibodies to the subject proteins and transgenic cells and organisms including the subject nucleic acid molecules. The subject protein and nucleic acid compositions find use in a variety of different applications. Finally, kits for use in such applications that include the subject nucleic acid compositions are provided.

32 Claims, 20 Drawing Sheets

OTHER PUBLICATIONS

Labas et al. Diversity and evolution of the green fluorescent protein family, Apr. 2, 2002. Proc. Nat. Acad. Sci., USA 99(7): 4256-4261.*

Cormack et al. FACS-optimized mutants of the green fluorescent protein (GFP) *Gene* 173 (996) 33-38.

Matz et al. "Fluorescent proteins from nonbioluminescent Anthozoa species" *Nature Biotechnology,* vol. 17, Oct. 1999 pp. 969-973.

Ormo et al "Crystal structure of the *Aequorea victoria* Green Fluorescent Protein" *Science* vol. 273, Sep. 6, 1996, pp. 1392-1395.

Tsien et al "The Greeen Fluorescent Protein" *Annu. Rev. Biochem,* 1998, 67:609-44.

Terskikh et al. "Fluorescent Timer": Protein that changes color with time, *Science,* vol. 290, Nov. 24, 2000.

* cited by examiner

FIGURE 1
Sequence of humanized drFP583 (SEQ ID NO:01 and NO:02)

```
  1  Met Arg Ser Ser Lys Asn Val Ile Lys Glu Phe Met Arg Phe Lys Val    16
  1  ATG CGC TCC TCC AAG AAC GTC ATC AAG GAG TTC ATG CGC TTC AAG GTG    48

17  Arg Met Glu Gly Thr Val Asn Gly His Glu Phe Glu Ile Glu Gly Glu    32
 49  CGC ATG GAG GGC ACC GTG AAC GGC CAC GAG TTC GAG ATC GAG GGC GAG    96

33  Gly Glu Gly Arg Pro Tyr Glu Gly His Asn Thr Val Lys Leu Lys Val    48
 97  GGC GAG GGC CGC CCC TAC GAG GGC CAC AAC ACC GTG AAG CTG AAG GTG   144

49  Thr Lys Gly Gly Pro Leu Pro Phe Ala Trp Asp Ile Leu Ser Pro Gln    64
145  ACC AAG GGC GGC CCC CTG CCC TTC GCC TGG GAC ATC CTG TCC CCC CAG   192

65  Phe Gln Tyr Gly Ser Lys Val Tyr Val Lys His Pro Ala Asp Ile Pro    80
193  TTC CAG TAC GGC TCC AAG GTG TAC GTG AAG CAC CCC GCC GAC ATC CCC   240

81  Asp Tyr Lys Lys Leu Ser Phe Pro Glu Gly Phe Lys Trp Glu Arg Val    96
241  GAC TAC AAG AAG CTG TCC TTC CCC GAG GGC TTC AAG TGG GAG CGC GTG   288
                                           105
 97  Met Asn Phe Glu Asp Gly Gly Val Val Thr Val Thr Gln Asp Ser Ser   112
289  ATG AAC TTC GAG GAC GGC GGC GTG GTG ACC GTG ACC CAG GAC TCC TCC   336

113  Leu Gln Asp Gly Cys Phe Ile Tyr Lys Val Lys Phe Ile Gly Val Asn   128
337  CTG CAG GAC GGC TGC TTC ATC TAC AAG GTG AAG TTC ATC GGC GTG AAC   384

129  Phe Pro Ser Asp Gly Pro Val Met Gln Lys Lys Thr Met Gly Trp Glu   144
385  TTC CCC TCC GAC GGC CCC GTG ATG CAG AAG AAG ACC ATG GGC TGG GAG   432

145  Ala Ser Thr Glu Arg Leu Tyr Pro Arg Asp Gly Val Leu Lys Gly Glu   160
433  GCC TCC ACC GAG CGC CTG TAC CCC CGC GAC GGC GTG CTG AAG GGC GAG   480

161  Ile His Lys Ala Leu Lys Leu Lys Asp Gly Gly His Tyr Leu Val Glu   176
481  ATC CAC AAG GCC CTG AAG CTG AAG GAC GGC GGC CAC TAC CTG GTG GAG   528

177  Phe Lys Ser Ile Tyr Met Ala Lys Lys Pro Val Gln Leu Pro Gly Tyr   192
529  TTC AAG TCC ATC TAC ATG GCC AAG AAG CCC GTG CAG CTG CCC GGC TAC   576
                                  197
193  Tyr Tyr Val Asp Ser Lys Leu Asp Ile Thr Ser His Asn Glu Asp Tyr   208
577  TAC TAC GTG GAC TCC AAG CTG GAC ATC ACC TCC CAC AAC GAG GAC TAC   624

209  Thr Ile Val Glu Gln Tyr Glu Arg Thr Glu Gly Arg His His Leu Phe   224
625  ACC ATC GTG GAG CAG TAC GAG CGC ACC GAG GGC CGC CAC CAC CTG TTC   672

225  Leu ***
673  CTG TAA
```

FIGURE 2
Sequence of E5 (SEQ ID NO:03 and NO:04)

```
  1  Met Arg Ser Ser Lys Asn Val Ile Lys Glu Phe Met Arg Phe Lys Val    16
  1  ATG CGC TCC TCC AAG AAC GTC ATC AAG GAG TTC ATG CGC TTC AAG GTG    48

17  Arg Met Glu Gly Thr Val Asn Gly His Glu Phe Glu Ile Glu Gly Glu    32
 49  CGC ATG GAG GGC ACC GTG AAC GGC CAC GAG TTC GAG ATC GAG GGC GAG    96

33  Gly Glu Gly Arg Pro Tyr Glu Gly His Asn Thr Val Lys Leu Lys Val    48
 97  GGC GAG GGC CGC CCC TAC GAG GGC CAC AAC ACC GTG AAG CTG AAG GTG   144

49  Thr Lys Gly Gly Pro Leu Pro Phe Ala Trp Asp Ile Leu Ser Pro Gln    64
145  ACC AAG GGC GGC CCC CTG CCC TTC GCC TGG GAC ATC CTG TCC CCC CAG   192

65  Phe Gln Tyr Gly Ser Lys Val Tyr Val Lys His Pro Ala Asp Ile Pro    80
193  TTC CAG TAC GGC TCC AAG GTG TAC GTG AAG CAC CCC GCC GAC ATC CCC   240

81  Asp Tyr Lys Lys Leu Ser Phe Pro Glu Gly Phe Lys Trp Glu Arg Val    96
241  GAC TAC AAG AAG CTG TCC TTC CCC GAG GGC TTC AAG TGG GAG CGC GTG   288
                                         105
 97  Met Asn Phe Glu Asp Gly Gly Val Ala Thr Val Thr Gln Asp Ser Ser   112
289  ATG AAC TTC GAG GAC GGC GGC GTG GCG ACC GTG ACC CAG GAC TCC TCC   336

113  Leu Gln Asp Gly Cys Phe Ile Tyr Lys Val Lys Phe Ile Gly Val Asn   128
337  CTG CAG GAC GGC TGC TTC ATC TAC AAG GTG AAG TTC ATC GGC GTG AAC   384

129  Phe Pro Ser Asp Gly Pro Val Met Gln Lys Lys Thr Met Gly Trp Glu   144
385  TTC CCC TCC GAC GGC CCC GTG ATG CAG AAG AAG ACC ATG GGC TGG GAG   432

145  Ala Ser Thr Glu Arg Leu Tyr Pro Arg Asp Gly Val Leu Lys Gly Glu   160
433  GCC TCC ACC GAG CGC CTG TAC CCC CGC GAC GGC GTG CTG AAG GGC GAG   480

161  Ile His Lys Ala Leu Lys Leu Lys Asp Gly Gly His Tyr Leu Val Glu   176
481  ATC CAC AAG GCC CTG AAG CTG AAG GAC GGC GGC CAC TAC CTG GTG GAG   528

177  Phe Lys Ser Ile Tyr Met Ala Lys Lys Pro Val Gln Leu Pro Gly Tyr   192
529  TTC AAG TCC ATC TAC ATG GCC AAG AAG CCC GTG CAG CTG CCC GGC TAC   576
                         197
193  Tyr Tyr Val Asp Thr Lys Leu Asp Ile Thr Ser His Asn Glu Asp Tyr   208
577  TAC TAC GTG GAC ACC AAG CTG GAC ATC ACC TCC CAC AAC GAG GAC TAC   624

209  Thr Ile Val Glu Gln Tyr Glu Arg Thr Glu Gly Arg His His Leu Phe   224
625  ACC ATC GTG GAG CAG TAC GAG CGC ACC GAG GGC CGC CAC CAC CTG TTC   672

225  Leu ***
     CTG TAA
```

FIGURE 3
Sequence of non-aggregating mutant of E5, E5NA (SEQ ID NO :05 and NO :06)

```
  1   Met Ala Ser Ser Glu Asn Val Ile Thr Glu Phe Met Arg Phe Lys Val    16
  1   ATG GCC TCC TCC GAG AAC GTC ATC ACC GAG TTC ATG CGC TTC AAG GTG    48

17   Arg Met Glu Gly Thr Val Asn Gly His Glu Phe Glu Ile Glu Gly Glu    32
 49   CGC ATG GAG GGC ACC GTG AAC GGC CAC GAG TTC GAG ATC GAG GGC GAG    96

33   Gly Glu Gly Arg Pro Tyr Glu Gly His Asn Thr Val Lys Leu Lys Val    48
 97   GGC GAG GGC CGC CCC TAC GAG GGC CAC AAC ACC GTG AAG CTG AAG GTG   144

49   Thr Lys Gly Gly Pro Leu Pro Phe Ala Trp Asp Ile Leu Ser Pro Gln    64
145   ACC AAG GGC GGC CCC CTG CCC TTC GCC TGG GAC ATC CTG TCC CCC CAG   192

65   Phe Gln Tyr Gly Ser Lys Val Tyr Val Lys His Pro Ala Asp Ile Pro    80
193   TTC CAG TAC GGC TCC AAG GTG TAC GTG AAG CAC CCC GCC GAC ATC CCC   240

81   Asp Tyr Lys Lys Leu Ser Phe Pro Glu Gly Phe Lys Trp Glu Arg Val    96
241   GAC TAC AAG AAG CTG TCC TTC CCC GAG GGC TTC AAG TGG GAG CGC GTG   288
                                          105
 97   Met Asn Phe Glu Asp Gly Gly Val Ala Thr Val Thr Gln Asp Ser Ser   112
289   ATG AAC TTC GAG GAC GGC GGC GTG GCG ACC GTG ACC CAG GAC TCC TCC   336

113   Leu Gln Asp Gly Cys Phe Ile Tyr Lys Val Lys Phe Ile Gly Val Asn   128
337   CTG CAG GAC GGC TGC TTC ATC TAC AAG GTG AAG TTC ATC GGC GTG AAC   384

129   Phe Pro Ser Asp Gly Pro Val Met Gln Lys Lys Thr Met Gly Trp Glu   144
385   TTC CCC TCC GAC GGC CCC GTG ATG CAG AAG AAG ACC ATG GGC TGG GAG   432

145   Ala Ser Thr Glu Arg Leu Tyr Pro Arg Asp Gly Val Leu Lys Gly Glu   160
433   GCC TCC ACC GAG CGC CTG TAC CCC CGC GAC GGC GTG CTG AAG GGC GAG   480

161   Ile His Lys Ala Leu Lys Leu Lys Asp Gly Gly His Tyr Leu Val Glu   176
481   ATC CAC AAG GCC CTG AAG CTG AAG GAC GGC GGC CAC TAC CTG GTG GAG   528

177   Phe Lys Ser Ile Tyr Met Ala Lys Lys Pro Val Gln Leu Pro Gly Tyr   192
529   TTC AAG TCC ATC TAC ATG GCC AAG AAG CCC GTG CAG CTG CCC GGC TAC   576

193   Tyr Tyr Val Asp Thr Lys Leu Asp Ile Thr Ser His Asn Glu Asp Tyr   208
577   TAC TAC GTG GAC ACC AAG CTG GAC ATC ACC TCC CAC AAC GAG GAC TAC   624

209   Thr Ile Val Glu Gln Tyr Glu Arg Thr Glu Gly Arg His His Leu Phe   224
625   ACC ATC GTG GAG CAG TAC GAG CGC ACC GAG GGC CGC CAC CAC CTG TTC   672

225   Leu ***
      CTG TAA
```

FIGURE 6
0h　　　　　24h

FIG. 12
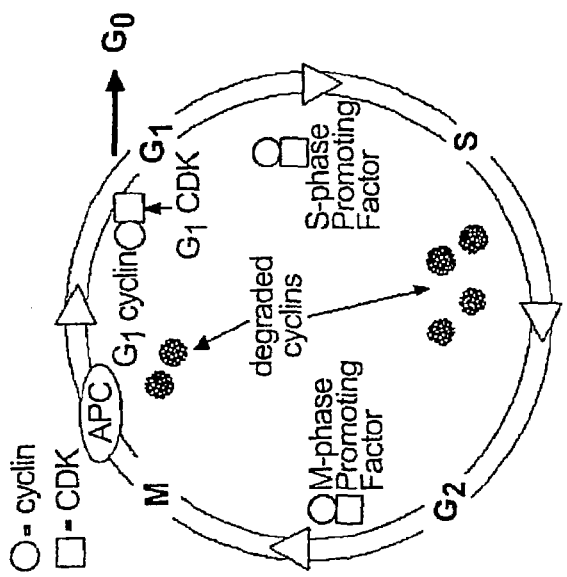
E2F1 promoter:
- increases approximately 80-fold at the G1/S-phase boundary
- regulated by G0-specific repression via the E2F sites

SEQUENCE LISTING

```
<160> NUMBER OF SEQ ID NOS: 22

<210> SEQ ID NO 1
<211> LENGTH: 678
<212> TYPE: DNA
<213> ORGANISM: Artificial Sequence
<220> FEATURE:
<223> OTHER INFORMATION: variant of sequence from Discosoma sp.

<400> SEQUENCE: 1
atgcgctcct ccaagaacgt catcaaggag ttcatgcgct tcaaggtgcg catggagggc        60
accgtgaacg gccacgagtt cgagatcgag ggcgagggcg agggccgccc ctacgagggc       120
cacaacaccg tgaagctgaa ggtgaccaag ggcggccccc tgcccttcgc ctgggacatc       180
ctgtcccccc agttccagta cggctccaag gtgtacgtga agcaccccgc cgacatcccc       240
gactacaaga agctgtcctt ccccgagggc ttcaagtggg agcgcgtgat gaacttcgag       300
gacggcggcg tggtgaccgt gacccaggac tcctccctgc aggacggctg cttcatctac       360
aaggtgaagt tcatcggcgt gaacttcccc tccgacggcc ccgtgatgca gaagaagacc       420
atgggctggg aggcctccac cgagcgcctg taccccgcg acgcgtgct gaagggcgag        480 atccacaagg ccctgaagct gaaggacggc ggccactacc tggtggagtt caagtccatc       540
```

```
tacatggcca agaagcccgt gcagctgccc ggctactact acgtggactc caagctggac    600
atcacctccc acaacgagga ctacaccatc gtggagcagt acgagcgcac cgagggccgc    660
caccacctgt tcctgtaa                                                   678
```

<210> SEQ ID NO 2
<211> LENGTH: 225
<212> TYPE: PRT
<213> ORGANISM: Discosoma sp.

<400> SEQUENCE: 2

```
Met Arg Ser Ser Lys Asn Val Ile Lys Glu Phe Met Arg Phe Lys Val
  1               5                  10                  15

Arg Met Glu Gly Thr Val Asn Gly His Glu Phe Glu Ile Glu Gly Glu
             20                  25                  30

Gly Glu Gly Arg Pro Tyr Glu Gly His Asn Thr Val Lys Leu Lys Val
         35                  40                  45

Thr Lys Gly Gly Pro Leu Pro Phe Ala Trp Asp Ile Leu Ser Pro Gln
     50                  55                  60

Phe Gln Tyr Gly Ser Lys Val Tyr Val Lys His Pro Ala Asp Ile Pro
 65                  70                  75                  80

Asp Tyr Lys Lys Leu Ser Phe Pro Glu Gly Phe Lys Trp Glu Arg Val
                 85                  90                  95

Met Asn Phe Glu Asp Gly Gly Val Val Thr Val Thr Gln Asp Ser Ser
            100                 105                 110

Leu Gln Asp Gly Cys Phe Ile Tyr Lys Val Lys Phe Ile Gly Val Asn
        115                 120                 125

Phe Pro Ser Asp Gly Pro Val Met Gln Lys Lys Thr Met Gly Trp Glu
    130                 135                 140

Ala Ser Thr Glu Arg Leu Tyr Pro Arg Asp Gly Val Leu Lys Gly Glu
145                 150                 155                 160

Ile His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
            180                 185                 190

Tyr Tyr Val Asp Ser Lys Leu Asp Ile Thr Ser His Asn Glu Asp Tyr
        195                 200                 205

Thr Ile Val Glu Gln Tyr Glu Arg Thr Glu Gly Arg His His Leu Phe
    210                 215                 220

Leu
225
```

<210> SEQ ID NO 3
<211> LENGTH: 678
<212> TYPE: DNA
<213> ORGANISM: Artificial Sequence
<220> FEATURE:
<223> OTHER INFORMATION: variant of sequence from Discosoma sp.

<400> SEQUENCE: 3

```
atgcgctcct ccaagaacgt catcaaggag ttcatgcgct tcaaggtgcg catggagggc    60
accgtgaacg gccacgagtt cgagatcgag ggcgagggcg agggccgccc ctacgagggc    120
cacaacaccg tgaagctgaa ggtgaccaag ggcggccccc tgcccttcgc ctgggacatc    180
ctgtcccccc agttccagta cggctccaag gtgtacgtga agcaccccgc cgacatcccc    240
gactacaaga agctgtcctt ccccgagggc ttcaagtggg agcgcgtgat gaacttcgag    300
```

```
gacggcggcg tggcgaccgt gacccaggac tcctccctgc aggacggctg cttcatctac      360
aaggtgaagt tcatcggcgt gaacttcccc tccgacggcc ccgtgatgca aaagaagacc      420
atgggctggg aggcctccac cgagcgcctg taccccgcg acggcgtgct gaagggcgag       480
atccacaagg ccctgaagct gaaggacggc ggccactacc tggtggagtt caagtccatc      540
tacatggcca agaagcccgt gcagctgccc ggctactact acgtggacac caagctggac      600
atcacctccc acaacgagga ctacaccatc gtggagcagt acgagcgcac cgagggccgc      660
caccacctgt tcctgtaa                                                    678
```

```
<210> SEQ ID NO 4
<211> LENGTH: 225
<212> TYPE: PRT
<213> ORGANISM: Artificial Sequence
<220> FEATURE:
<223> OTHER INFORMATION: variant of sequence from Discosoma sp.

<400> SEQUENCE: 4

Met Arg Ser Ser Lys Asn Val Ile Lys Glu Phe Met Arg Phe Lys Val
 1               5                  10                  15

Arg Met Glu Gly Thr Val Asn Gly His Glu Phe Glu Ile Glu Gly Glu
             20                  25                  30

Gly Glu Gly Arg Pro Tyr Glu Gly His Asn Thr Val Lys Leu Lys Val
         35                  40                  45

Thr Lys Gly Gly Pro Leu Pro Phe Ala Trp Asp Ile Leu Ser Pro Gln
     50                  55                  60

Phe Gln Tyr Gly Ser Lys Val Tyr Val Lys His Pro Ala Asp Ile Pro
 65                  70                  75                  80

Asp Tyr Lys Lys Leu Ser Phe Pro Glu Gly Phe Lys Trp Glu Arg Val
                 85                  90                  95

Met Asn Phe Glu Asp Gly Gly Val Ala Thr Val Thr Gln Asp Ser Ser
            100                 105                 110

Leu Gln Asp Gly Cys Phe Ile Tyr Lys Val Lys Phe Ile Gly Val Asn
        115                 120                 125

Phe Pro Ser Asp Gly Pro Val Met Gln Lys Lys Thr Met Gly Trp Glu
    130                 135                 140

Ala Ser Thr Glu Arg Leu Tyr Pro Arg Asp Gly Val Leu Lys Gly Glu
145                 150                 155                 160

Ile His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
            180                 185                 190

Tyr Tyr Val Asp Thr Lys Leu Asp Ile Thr Ser His Asn Glu Asp Tyr
        195                 200                 205

Thr Ile Val Glu Gln Tyr Glu Arg Thr Glu Gly Arg His His Leu Phe
    210                 215                 220

Leu
225

<210> SEQ ID NO 5
<211> LENGTH: 678
<212> TYPE: DNA
<213> ORGANISM: Artificial Sequence
<220> FEATURE:
<223> OTHER INFORMATION: variant of sequence from Discosoma sp.
```

<400> SEQUENCE: 5

```
atggcctcct ccgagaacgt catcaccgag ttcatgcgct tcaaggtgcg catggagggc      60
accgtgaacg ccacgagtt cgagatcgag ggcgagggcg agggccgccc ctacgagggc     120
cacaacaccg tgaagctgaa ggtgaccaag ggcggccccc tgcccttcgc ctgggacatc     180
ctgtccccc agttccagta cggctccaag gtgtacgtga agcaccccgc cgacatcccc     240
gactacaaga agctgtcctt ccccgagggc ttcaagtggg agcgcgtgat gaacttcgag     300
gacggcggcg tggcgaccgt gacccaggac tcctccctgc aggacggctg cttcatctac     360
aaggtgaagt tcatcggcgt gaacttcccc tccgacggcc ccgtgatgca gaagaagacc     420
atgggctggg aggcctccac cgagcgcctg taccccgcg acggcgtgct gaagggcgag     480
atccacaagg ccctgaagct gaaggacggc ggccactacc tggtggagtt caagtccatc     540
tacatggcca agaagcccgt gcagctgccc ggctactact acgtggacac caagctggac     600
atcacctccc acaacgagga ctacaccatc gtggagcagt acgagcgcac cgagggccgc     660
caccacctgt tcctgtaa                                                   678
```

<210> SEQ ID NO 6
<211> LENGTH: 225
<212> TYPE: PRT
<213> ORGANISM: Artificial Sequence
<220> FEATURE:
<223> OTHER INFORMATION: variant of sequence from Discosoma sp.

<400> SEQUENCE: 6

```
Met Ala Ser Ser Glu Asn Val Ile Thr Glu Phe Met Arg Phe Lys Val
  1               5                  10                  15

Arg Met Glu Gly Thr Val Asn Gly His Glu Phe Glu Ile Glu Gly Glu
             20                  25                  30

Gly Glu Gly Arg Pro Tyr Glu Gly His Asn Thr Val Lys Leu Lys Val
         35                  40                  45

Thr Lys Gly Gly Pro Leu Pro Phe Ala Trp Asp Ile Leu Ser Pro Gln
     50                  55                  60

Phe Gln Tyr Gly Ser Lys Val Tyr Val Lys His Pro Ala Asp Ile Pro
 65                  70                  75                  80

Asp Tyr Lys Lys Leu Ser Phe Pro Glu Gly Phe Lys Trp Glu Arg Val
                 85                  90                  95

Met Asn Phe Glu Asp Gly Gly Val Ala Thr Val Thr Gln Asp Ser Ser
            100                 105                 110

Leu Gln Asp Gly Cys Phe Ile Tyr Lys Val Lys Phe Ile Gly Val Asn
        115                 120                 125

Phe Pro Ser Asp Gly Pro Val Met Gln Lys Lys Thr Met Gly Trp Glu
    130                 135                 140

Ala Ser Thr Glu Arg Leu Tyr Pro Arg Asp Gly Val Leu Lys Gly Glu
145                 150                 155                 160

Ile His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
            180                 185                 190

Tyr Tyr Val Asp Thr Lys Leu Asp Ile Thr Ser His Asn Glu Asp Tyr
        195                 200                 205
```

-continued

```
Thr Ile Val Glu Gln Tyr Glu Arg Thr Glu Gly Arg His His Leu Phe
    210                 215                 220
Leu
225

<210> SEQ ID NO 7
<211> LENGTH: 7
<212> TYPE: PRT
<213> ORGANISM: Artificial Sequence
<220> FEATURE:
<223> OTHER INFORMATION: nuclear localization signal

<400> SEQUENCE: 7

Pro Lys Lys Lys Arg Lys Val
1               5

<210> SEQ ID NO 8
<211> LENGTH: 7
<212> TYPE: PRT
<213> ORGANISM: Artificial Sequence
<220> FEATURE:
<223> OTHER INFORMATION: nuclear localization signal

<400> SEQUENCE: 8

Lys Lys Lys Arg Lys Val Cys
1               5

<210> SEQ ID NO 9
<211> LENGTH: 7
<212> TYPE: PRT
<213> ORGANISM: Artificial Sequence
<220> FEATURE:
<223> OTHER INFORMATION: nuclear localization signal

<400> SEQUENCE: 9

Gly Lys Lys Arg Ser Lys Ala
1               5

<210> SEQ ID NO 10
<211> LENGTH: 5
<212> TYPE: PRT
<213> ORGANISM: Artificial Sequence
<220> FEATURE:
<223> OTHER INFORMATION: nuclear localization signal

<400> SEQUENCE: 10

Lys Arg Pro Arg Pro
1               5

<210> SEQ ID NO 11
<211> LENGTH: 10
<212> TYPE: PRT
<213> ORGANISM: Artificial Sequence
<220> FEATURE:
<223> OTHER INFORMATION: nuclear localization signal

<400> SEQUENCE: 11

Gly Asn Lys Ala Lys Arg Gln Arg Ser Thr
1               5                   10

<210> SEQ ID NO 12
<211> LENGTH: 10
<212> TYPE: PRT
<213> ORGANISM: Artificial Sequence
<220> FEATURE:
<223> OTHER INFORMATION: nuclear localization signal
```

```
<400> SEQUENCE: 12

Gly Gly Ala Ala Lys Arg Val Lys Leu Asp
 1               5                  10

<210> SEQ ID NO 13
<211> LENGTH: 12
<212> TYPE: PRT
<213> ORGANISM: Artificial Sequence
<220> FEATURE:
<223> OTHER INFORMATION: nuclear localization signal

<400> SEQUENCE: 13

Ser Ala Leu Ile Lys Lys Lys Lys Lys Met Ala Pro
 1               5                  10

<210> SEQ ID NO 14
<211> LENGTH: 8
<212> TYPE: PRT
<213> ORGANISM: Artificial Sequence
<220> FEATURE:
<223> OTHER INFORMATION: nuclear localization signal

<400> SEQUENCE: 14

Arg Lys Leu Lys Lys Leu Gly Asn
 1               5

<210> SEQ ID NO 15
<211> LENGTH: 7
<212> TYPE: PRT
<213> ORGANISM: Artificial Sequence
<220> FEATURE:
<223> OTHER INFORMATION: nuclear localization signal

<400> SEQUENCE: 15

Pro Gln Pro Lys Lys Lys Pro
 1               5

<210> SEQ ID NO 16
<211> LENGTH: 9
<212> TYPE: PRT
<213> ORGANISM: Artificial Sequence
<220> FEATURE:
<223> OTHER INFORMATION: nuclear localization signal

<400> SEQUENCE: 16

Ala Ser Lys Ser Arg Lys Arg Lys Leu
 1               5

<210> SEQ ID NO 17
<211> LENGTH: 5
<212> TYPE: PRT
<213> ORGANISM: Artificial Sequence
<220> FEATURE:
<223> OTHER INFORMATION: nuclear localization signal

<400> SEQUENCE: 17

Lys Lys Lys Tyr Lys
 1               5

<210> SEQ ID NO 18
<211> LENGTH: 6
<212> TYPE: PRT
<213> ORGANISM: Artificial Sequence
<220> FEATURE:
<223> OTHER INFORMATION: nuclear localization signal
```

-continued

```
<400> SEQUENCE: 18

Lys Lys Lys Tyr Lys Cys
1               5

<210> SEQ ID NO 19
<211> LENGTH: 5
<212> TYPE: PRT
<213> ORGANISM: Artificial Sequence
<220> FEATURE:
<223> OTHER INFORMATION: nuclear localization signal

<400> SEQUENCE: 19

Lys Ser Lys Lys Lys
1               5

<210> SEQ ID NO 20
<211> LENGTH: 6
<212> TYPE: PRT
<213> ORGANISM: Artificial Sequence
<220> FEATURE:
<223> OTHER INFORMATION: nuclear localization signal

<400> SEQUENCE: 20

Ala Lys Arg Val Lys Leu
1               5

<210> SEQ ID NO 21
<211> LENGTH: 6
<212> TYPE: PRT
<213> ORGANISM: Artificial Sequence
<220> FEATURE:
<223> OTHER INFORMATION: nuclear localization signal

<400> SEQUENCE: 21

Lys Arg Val Lys Leu Cys
1               5

<210> SEQ ID NO 22
<211> LENGTH: 7
<212> TYPE: PRT
<213> ORGANISM: Artificial Sequence
<220> FEATURE:
<223> OTHER INFORMATION: nuclear localization signal

<400> SEQUENCE: 22

Arg Arg Met Lys Trp Lys Lys
1               5
```

FLUORESCENT TIMER PROTEINS AND METHODS FOR THEIR USE

CROSS-REFERENCE TO RELATED APPLICATIONS

This application claims the benefit of U.S. Provisional Patent Application No. 60/211,607, filed Jun. 14, 2000, which application is hereby incorporated by reference in its entirety.

FIELD OF THE INVENTION

The field of this invention is fluorescent proteins and detectable labeling of proteins, cells, and organisms.

BACKGROUND OF THE INVENTION

Labeling is a tool for marking a protein, cell, or organism of interest and plays a prominent role in many biochemistry, molecular biology and medical diagnostic applications. A variety of different labels have been developed, including radiolabels, chromolabels, fluorescent labels, chemiluminescent labels, etc.

Fluorescent labels that are increasing in application are fluorescent proteins. Various fluorescent proteins have been described. For example, green fluorescent protein (GFP), a protein of the jellyfish *Aequorea victoria*, has an excitation maximum at 395 nm, a second excitation peak at 475 nm and an emission maximum at 510 nm. Other fluorescent proteins derived from Anthozoa species, e.g., corals, have been described. See the Literature section, below.

Fluorescent proteins are used in a wide variety of applications involving labeling of a protein, a cell, or a subcellular structure. Such applications include assessing gene expression during development of a multicellular organism, during the process of cellular differentiation, in response to a drug or other inducer of promoter activity. In these types of applications, a fluorescent protein is frequently used as a reporter to serve as a read-out of promoter activity. Other applications include monitoring intracellular protein movement or translocation, e.g., from one subcellular compartment to another, and monitoring protein intercellular protein movement.

Currently available fluorescent proteins exhibit emission spectra that do not change over time. Certain studies cannot be conducted effectively using these fluorescent proteins. For example, one cannot accurately study transient protein expression using fluorescent proteins currently available because one cannot tell from the signal of the protein whether the protein is newly synthesized or has been present in the cell for a long period of time.

As such, there is great interest in developing fluorescent proteins that change emission spectra over time.

Literature

For GFP, see, e.g., Haas, et al. (1996) *Current Biology* 6:315–324; Yang, et al. (1996) *Nucleic Acids Research* 24:4592–4593. GFP crystal structure is reported in Ormö et al. (1996) *Science* 273:1392–1395; and Yang et al. (1996) *Nature Biotechnol* 14:1246–1251. For Anthozoa-derived fluorescent proteins, see, e.g., WO 00/34318, WO 00/34319, WO 00/34320, WO 00/34321, WO 00/34322, WO 00/34323, WO 00/34324, WO 00/34325, WO 00/34326, and WO 00/34526. See also Matz et al. (1999) *Nature Biotechnol.* 17:969–973; and Terskikh et al. (November, 2000) *Science* 290:1585–1588.

SUMMARY OF THE INVENTION

Fluorescent "timer" proteins, which undergo a spectral shift over time after synthesis, as well as nucleic acid compositions encoding the same, are provided. Also provided are fragments of the subject proteins and nucleic acids encoding the same, as well as antibodies to the subject proteins and transgenic cells and organisms that include the subject nucleic acid molecules. The subject protein and nucleic acid compositions find use in a variety of different applications. Finally, kits for use in such applications that include the subject nucleic acid and protein compositions are provided.

BRIEF DESCRIPTIONS OF THE DRAWINGS

This patent or patent application file contains at least one drawing executed in color. Copies of this patent or patent application publication with color drawings will be provided by the U.S. Patent and Trademark Office upon request and payment of the necessary fee.

FIG. 1 provides the nucleotide and amino acid sequences of a humanized version of drFP583, i.e., E. (SEQ ID NO:1 (nt), 2 (aa)).

FIG. 2 provides the nucleotide and amino acid sequences of the fluorescent timer protein designated E5 (SEQ ID NO:3 (nt), 4 (aa)).

FIG. 3 provides the nucleotide and amino acid sequences of a non-aggregating mutant of E5, designated E5NA (SEQ ID NO:5 (nt), 6 (aa)).

FIGS. 4A–D are graphs depicting the results of in vitro spectral analysis of the E5 mutant. FIGS. 4A and 4C depict the emission spectra of the E5 and drFP583 proteins, respectively. FIG. 4B depicts the time course of green and red fluorescence development in E5 at 37° C. and 50° C. FIG. 4D depicts the absorption spectra of acid- or alkali-denatured E5, compared to the absorption spectra in PBS.

FIG. 6 depicts fluorescent images of 293 Tet-Off cells transfected with the E5 mutant.

Figure 7:
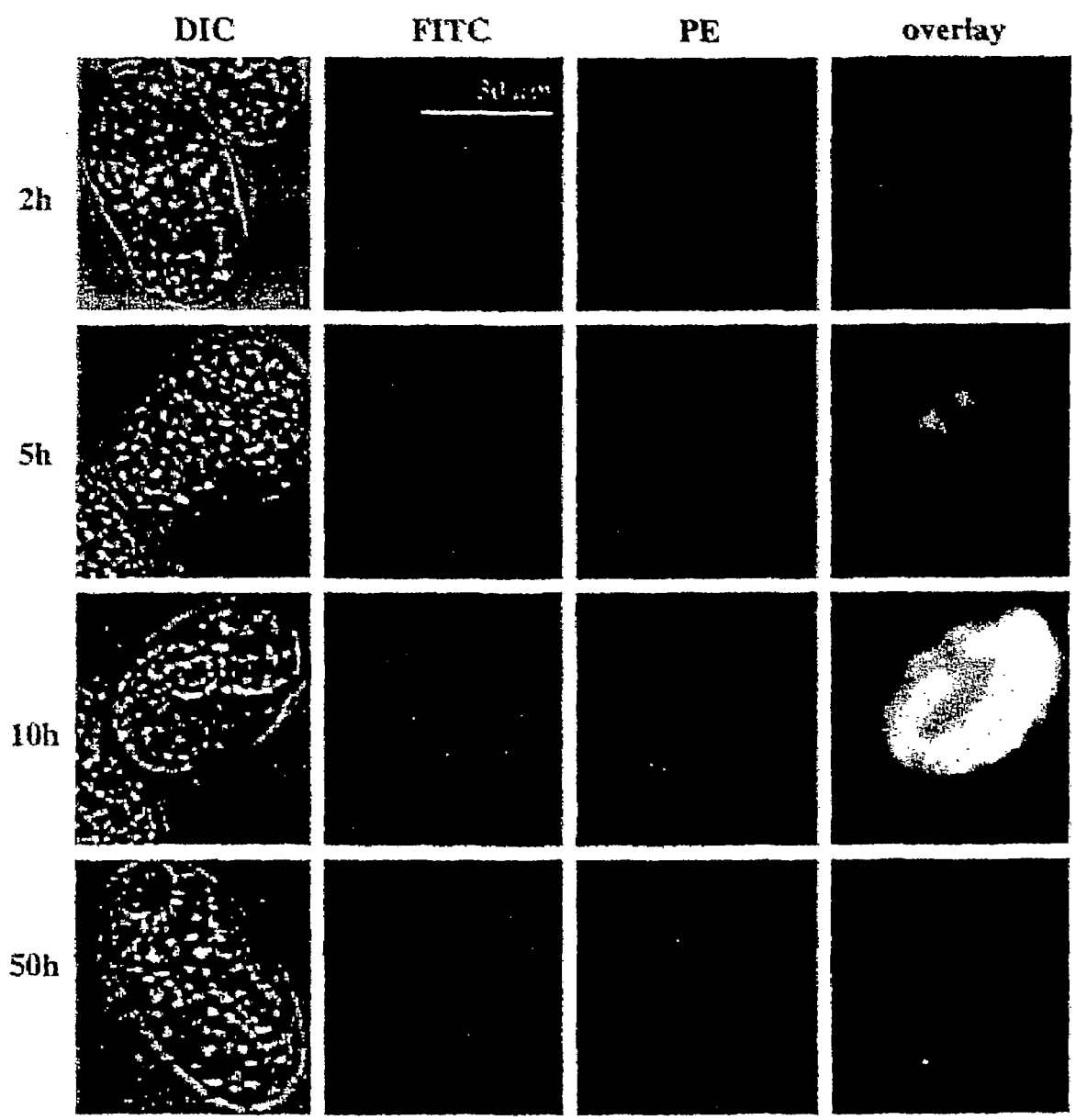

FIG. 7 depicts heat shock-regulated expression of E5 in *C. elegans*. Images are bright field (DIC); FITC filter; PE filter; and overlay at 2, 5, 10, and 50 hours after heat shock.

Figure 8:
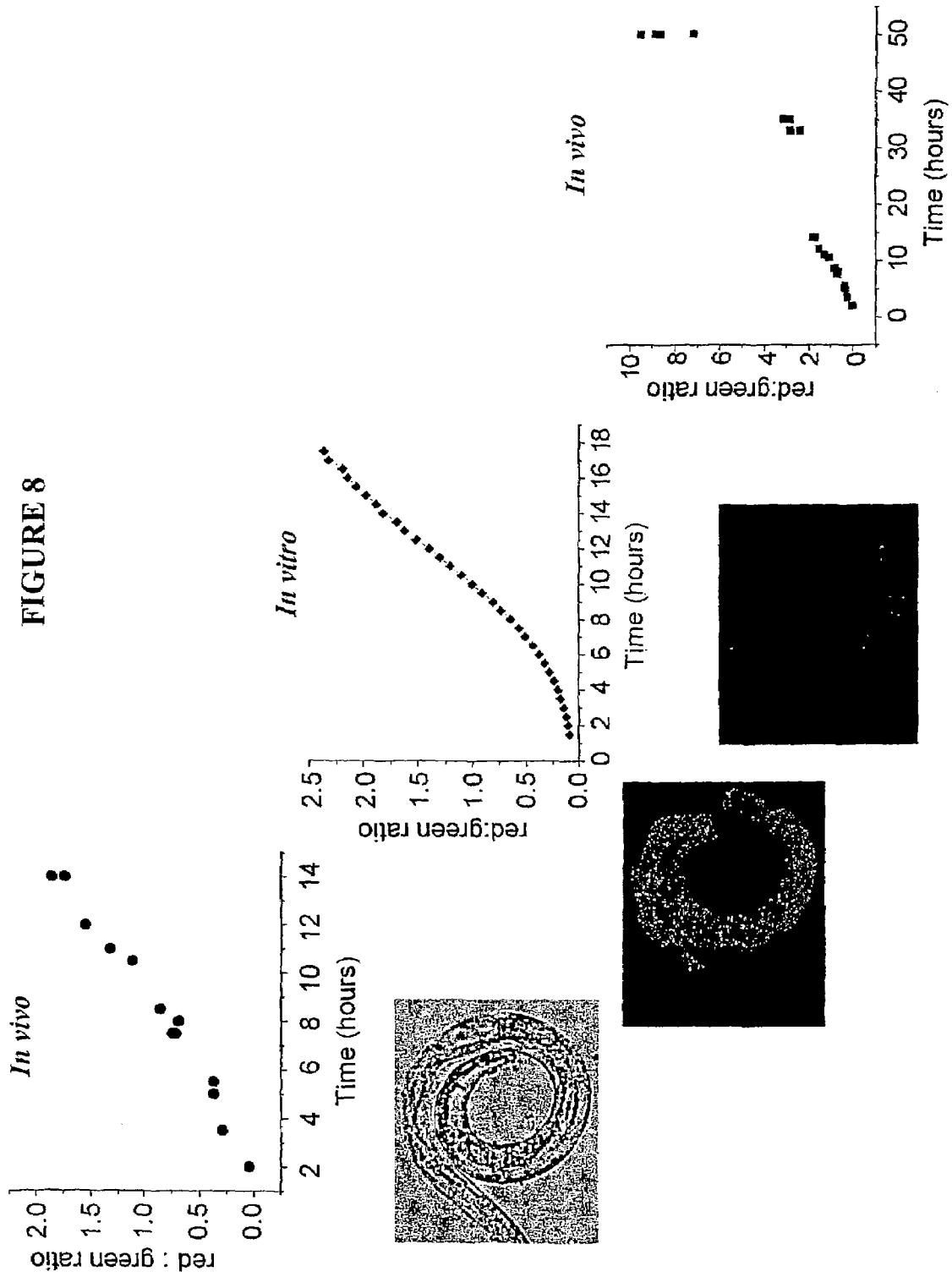

FIG. 8 depicts the spectral shift that E5 undergoes in *C. elegans*, and provides graphs depicting the red:green ratio over time both in vivo In *C. elegans*, and in vitro.

Figure 9:
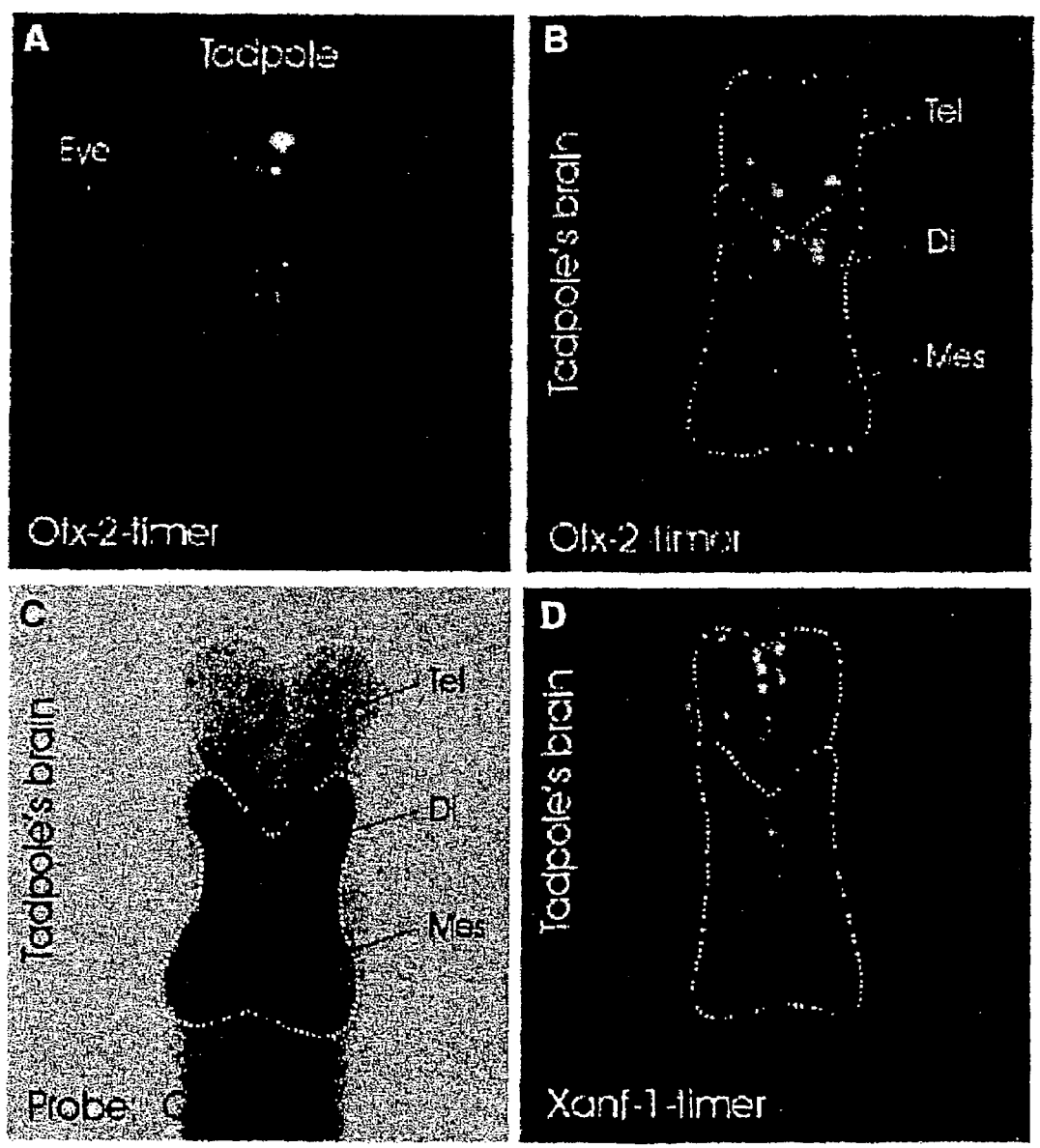

FIGS. 9A–D depict expression of E5 in a developing *Xenopus* embryo. FIG. 9A depicts a dorsal view of the tadpole expressing E5 under control of the Oxt-2 promoter. FIG. 9B depicts the brain region of the tadpole of FIG. 9A, where telencephalic (Tel) and di-and mesencephalic (Di and Mes, respectively) borders are designated by a dotted line. FIG. 9C depicts the dorsal view of the whole-mount in situ hybridization with an Oxt-2 probe. FIG. 9D depicts the dorsal view of the brain region of the tadpole expressing E5 under control of the Xanf-1 promoter.

Figure 10:
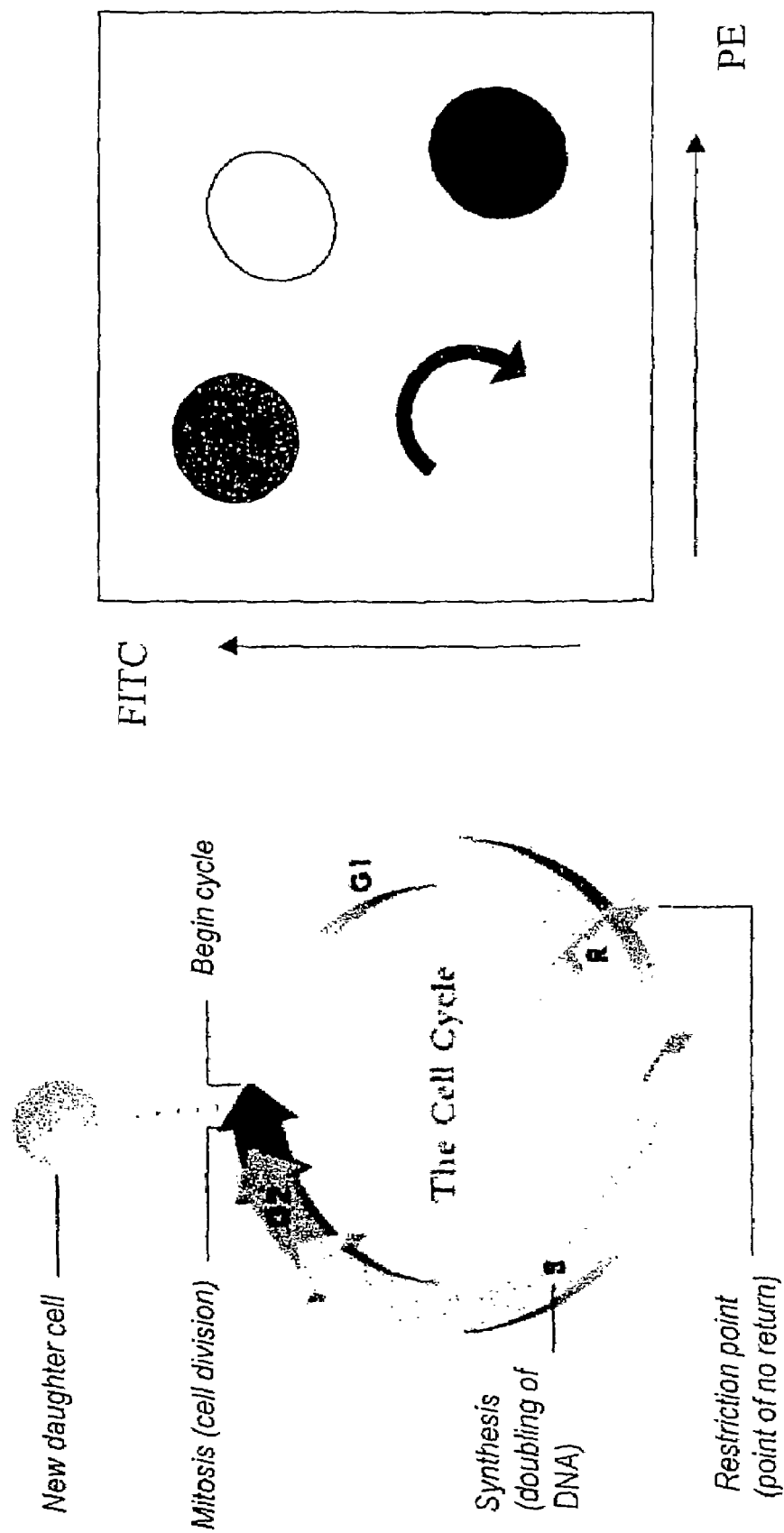

FIG. 10 shows the strategy for using a fluorescent timer protein to study cell cycle-regulated promoters.

Figure 11:
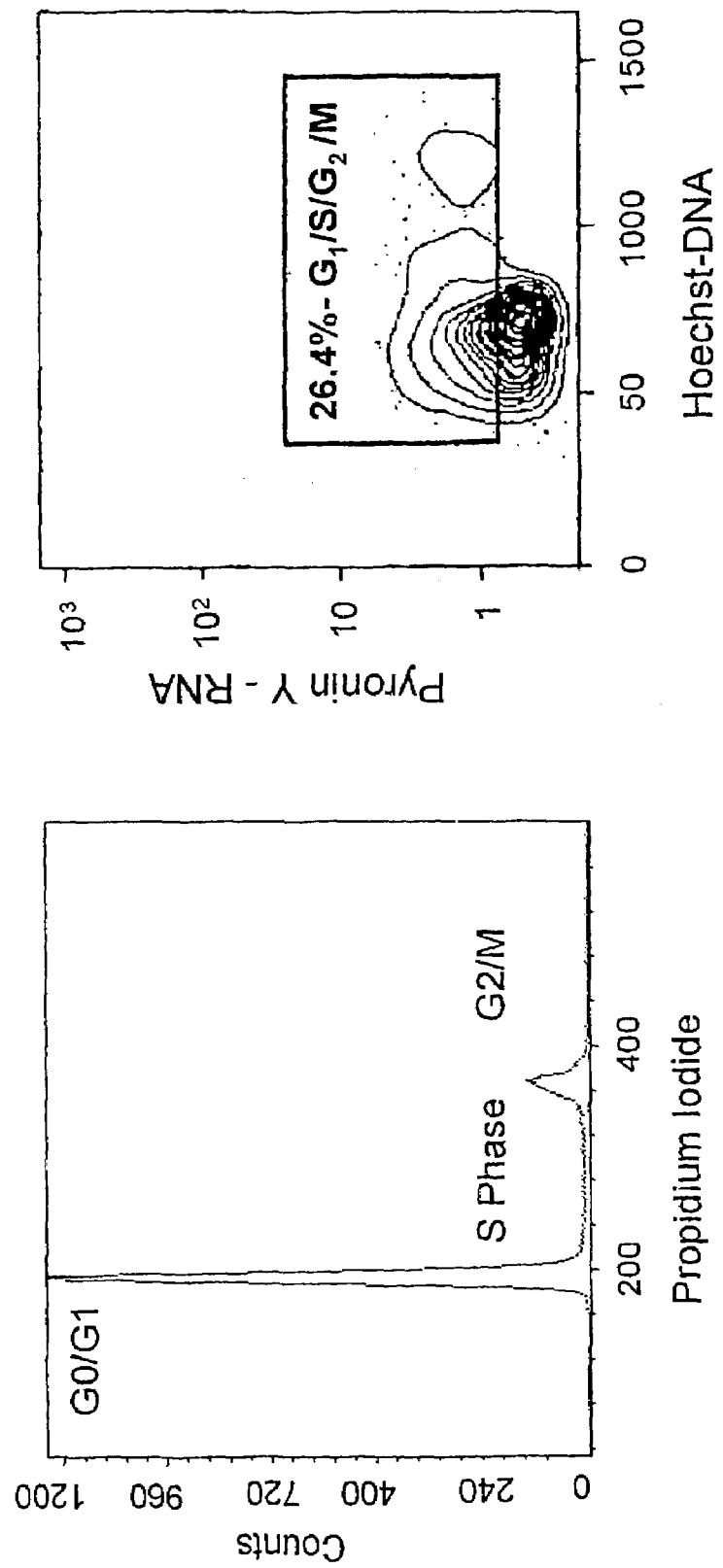

FIG. 11 depicts previously available methods of analyzing the cell cycle.

FIG. 12 provides a schematic representation of a construct including a cell cycle-regulated promoter, E2F1, driving transcription of a timer protein (left side); and depicts schematically the points in the cell cycle during which various cyclins are active, and where they are degraded (right side).

Figure 13:
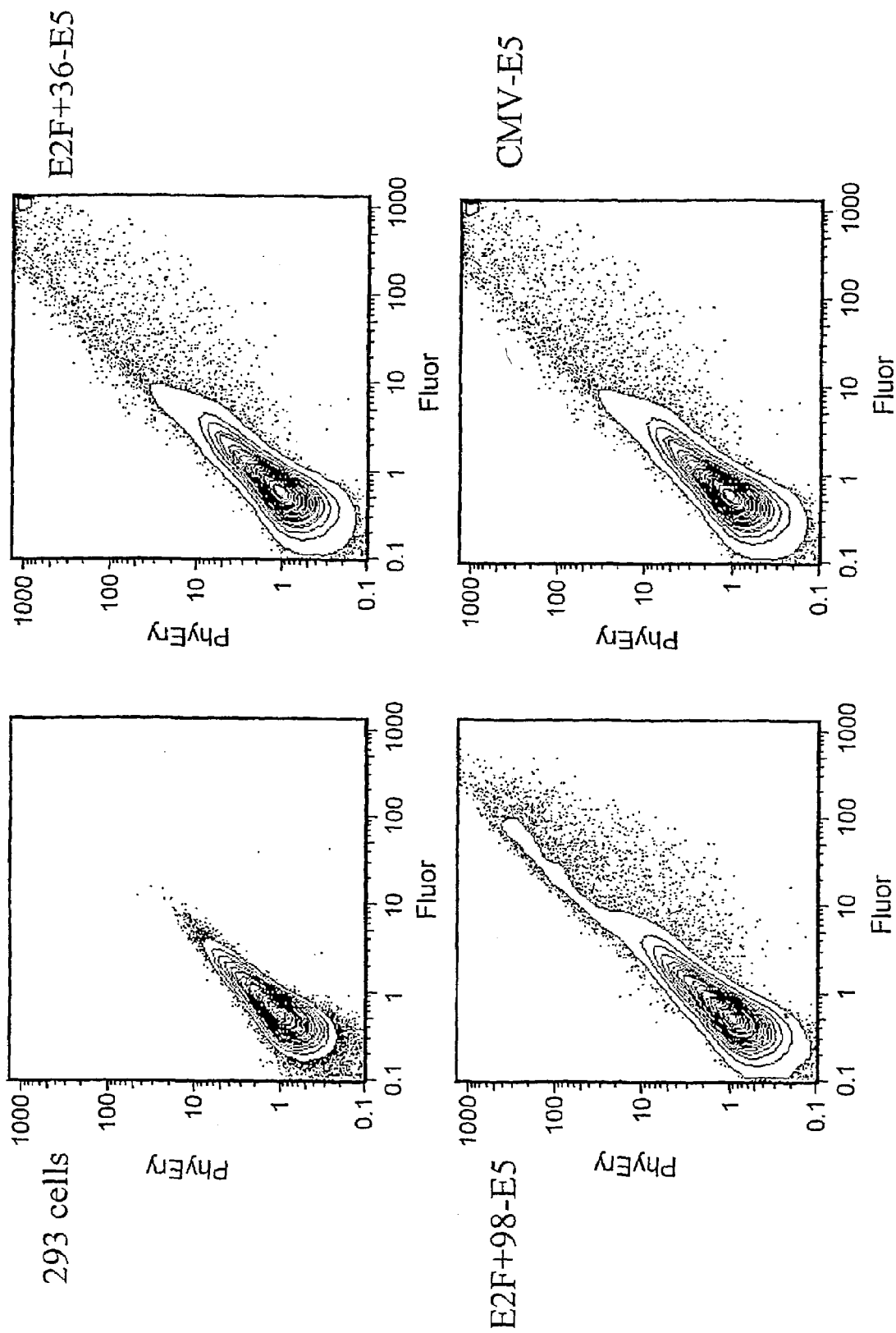

FIG. 13 depicts FACS plots of mock-transfected 293 cells ("293 cells"), and 293 cells transfected with plasmid constructs containing: an E2F promoter driving transcription of 36-E5 ("E2F+36-E5"); an E2F promoter driving transcription of 98-E5 ("E2F+98-E5"); a CMV promoter driving transcription of E5 ("CMV-E5").

Figure 14:
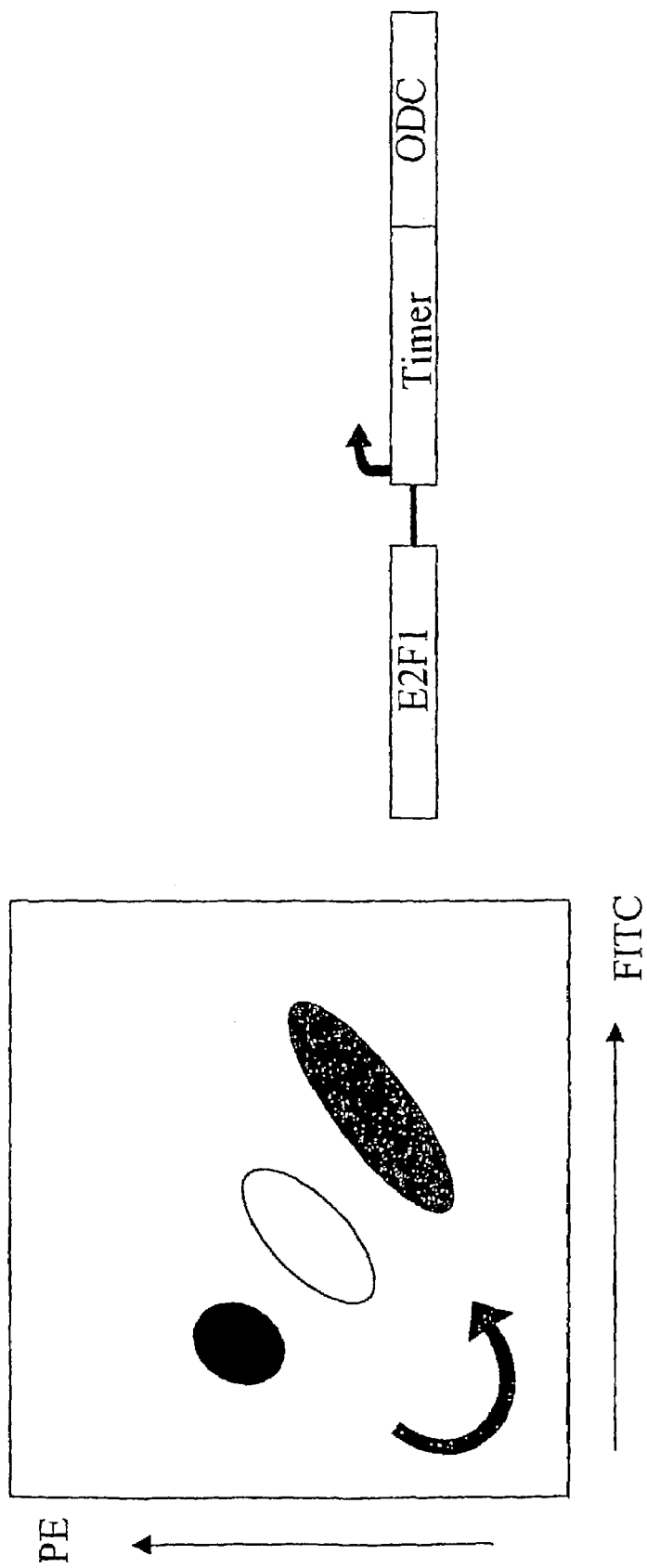

FIG. 14 depicts schematically a construct including a cell cycle regulated promoter driving transcription of a fluorescent timer-ODC fusion protein (right panel); and provides an expected distribution of fluorescence in cells containing such a construct (left panel).

Figure 15:
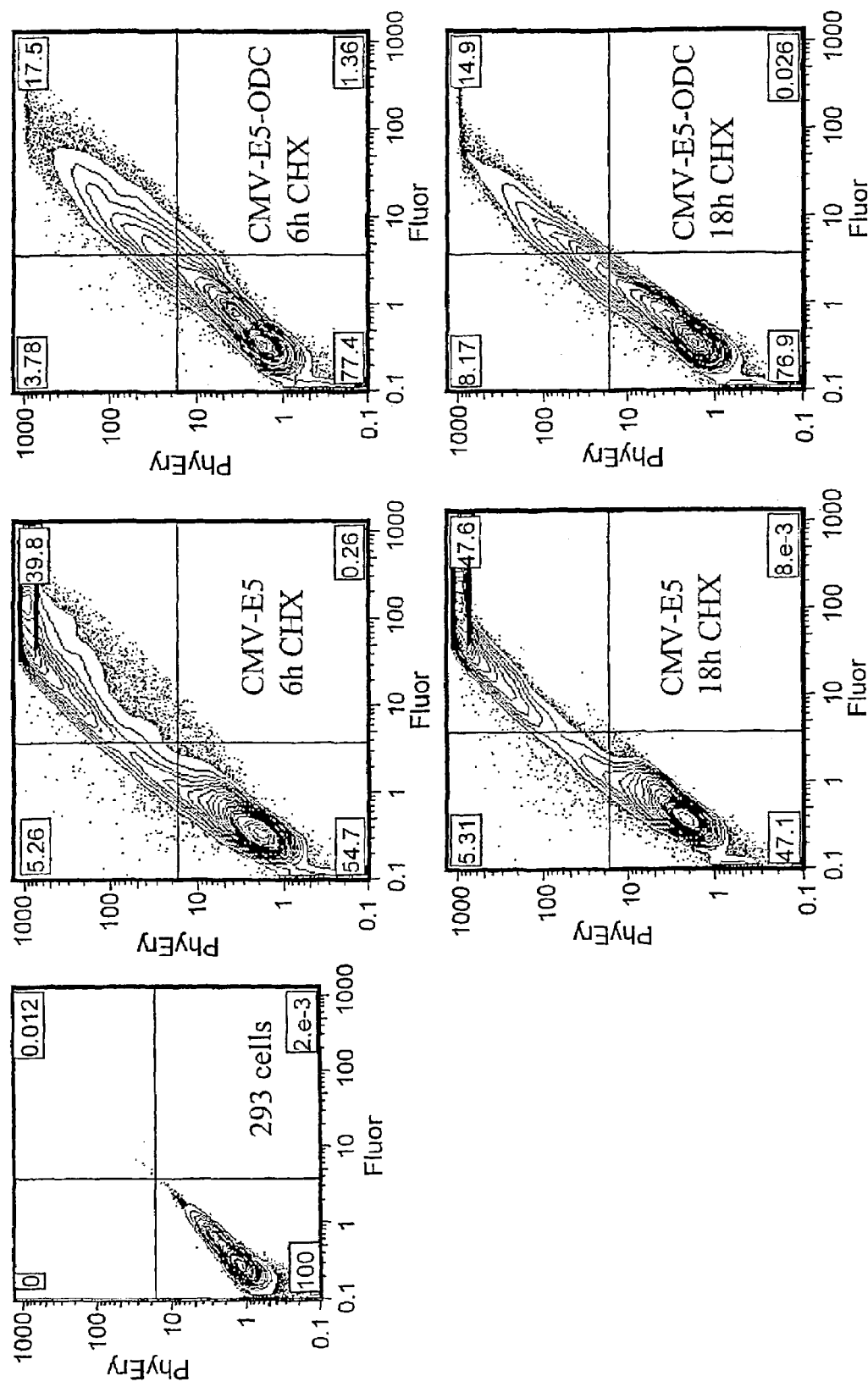

FIG. 15 depicts FACS plots of mock-transfected 293 cells ("293 cells"), and 293 cells transfected with plasmid constructs containing: a CMV promoter driving transcription of E5 ("CMV-E5"); and a CMV promoter driving transcription of an E5-ODC fission protein ("CMV-E5-ODC"). Cells were treated at 6 or 18 hours, as indicated, with cycloheximide (CHX).

Figure 16:
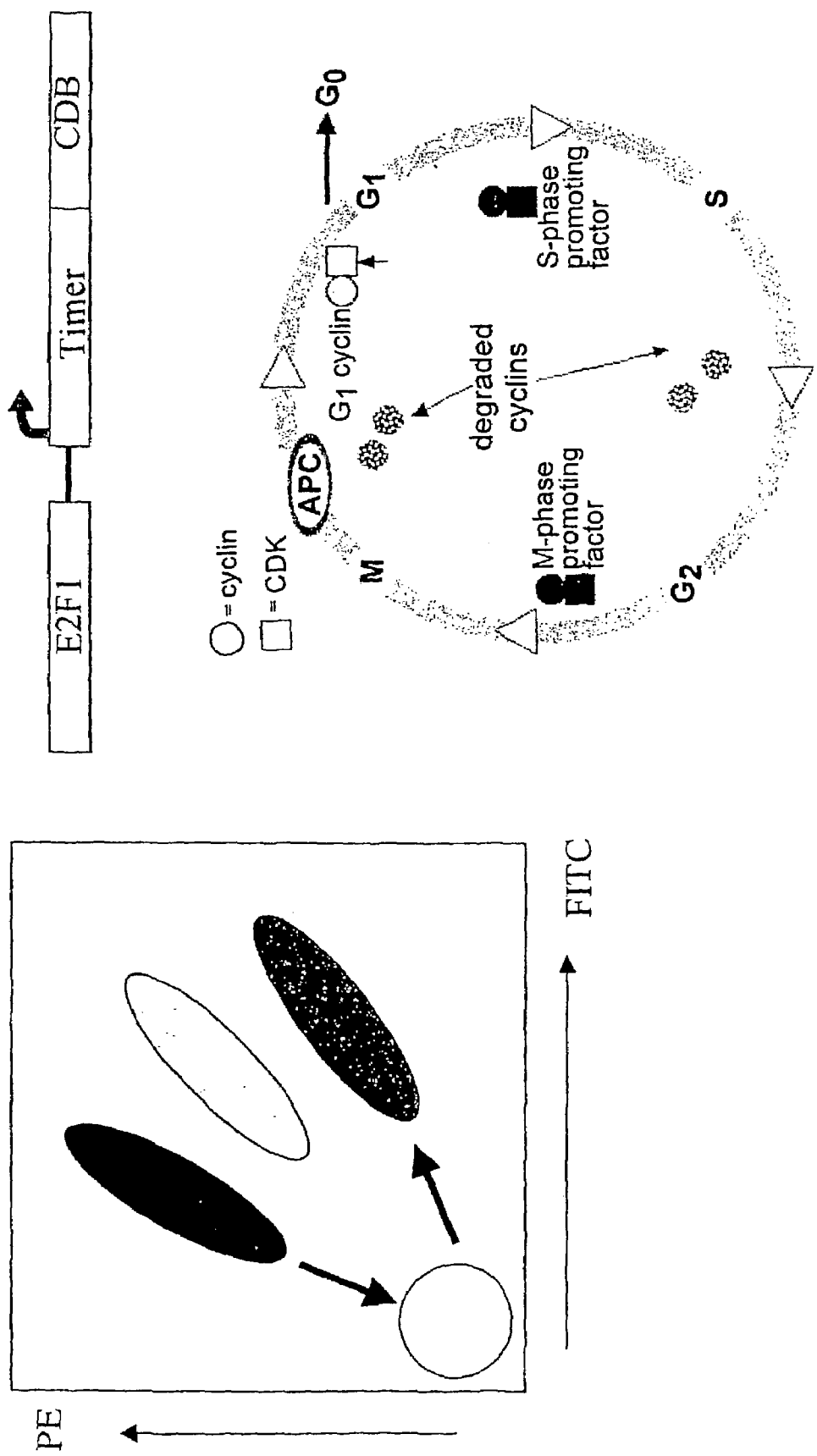

FIG. 16 depicts experiments using plasmid constructs including an E2F1 promoter driving the transcription of a nucleic acid molecule encoding a timer protein fused to a cyclin B1 degradation signal (CDB).

Figure 17:
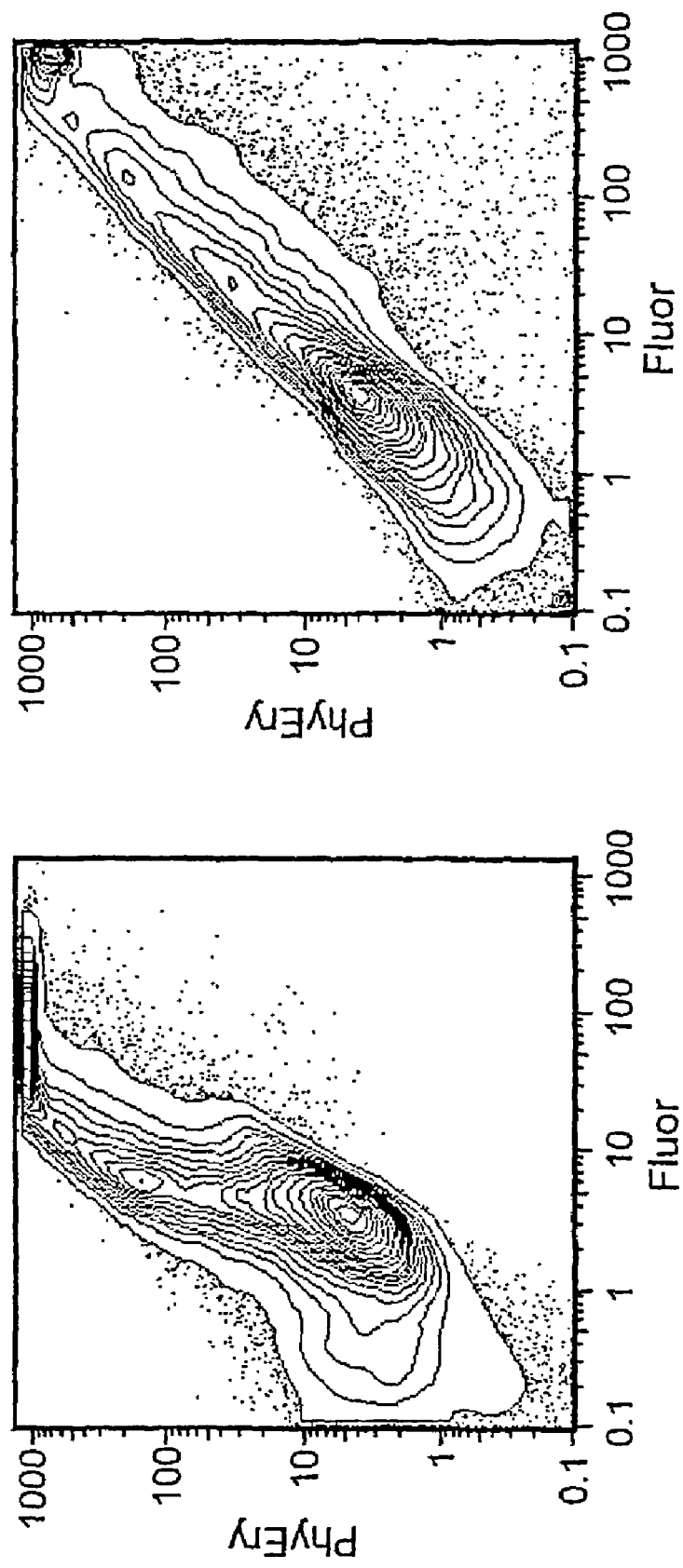

FIG. 17 depicts FACS analysis of MSCV-E5NA expression in 293 cells.

Figure 18:
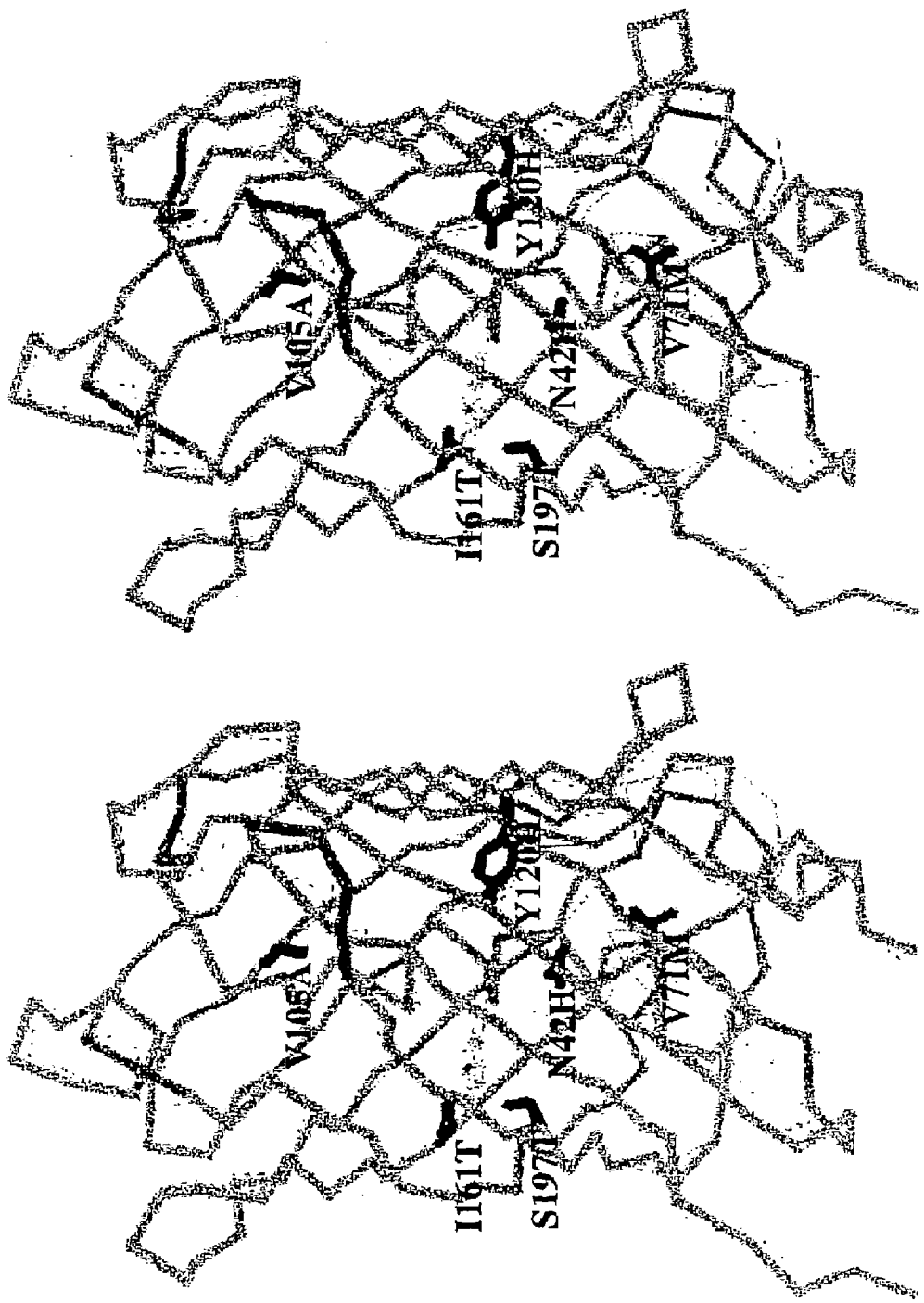

FIG. 18 depicts the overall protein structure of E5.

Figure 19:
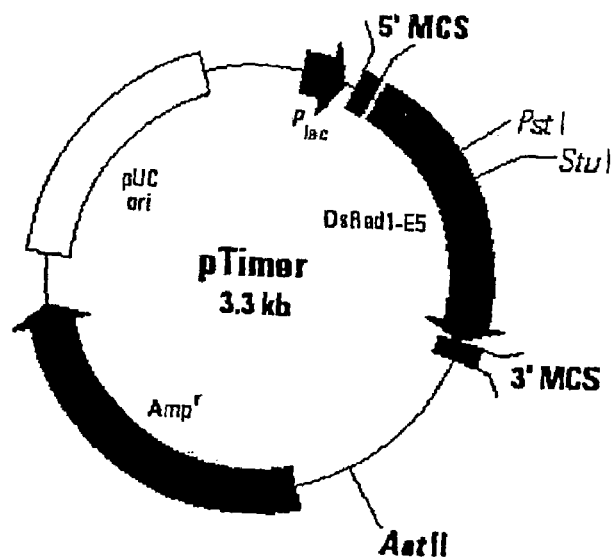

FIG. 19 depicts a recombinant vector that includes an E5 coding region flanked by a 5' multiple cloning site (SEQ ID NO:23) and a 3' multiple cloning site (SEQ ID NO:24).

Figure 20:
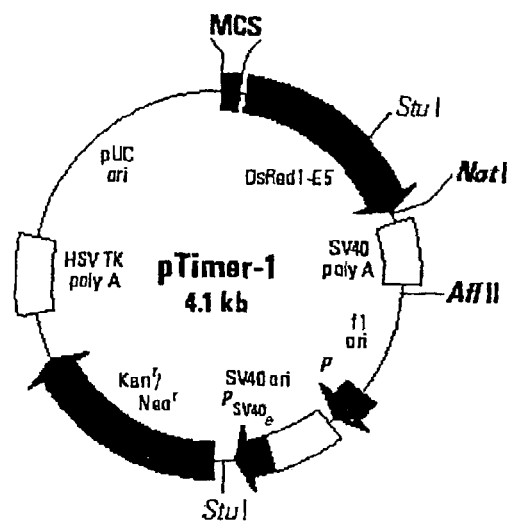

FIG. 20 depicts a recombinant vector that includes an E5 coding region, a multiple cloning site (SEQ ID NO:25), and regulatory sequences suitable for expression in eukaryotic cells.

DEFINITIONS

A "vector" is a replicon, such as plasmid, phage or cosmid, to which another DNA segment may be attached so as to bring about the replication of the attached segment.

The terms "polynucleotide" and "nucleic acid molecule" are used interchangeably herein to refer to polymeric forms of nucleotides of any length. The polynucleotides may contain deoxyribonucleotides, ribonucleotides, and/or their analogs. Nucleotides may have any three-dimensional structure, and may perform any function, known or unknown. The term "polynucleotide" includes single-, double-stranded and triple helical molecules. "Oligonucleotide" generally refers to polynucleotides of between about 5 and about 100 nucleotides of single- or double-stranded DNA. However, for the purposes of this disclosure, there is no upper limit to the length of an oligonucleotide. Oligonucleotides are also known as oligomers or oligos and may be isolated from genes, or chemically synthesized by methods known in the art. The term "polynucleotide" includes double-stranded DNA found, inter alia, in linear DNA molecules (e.g., restriction fragments), viruses, plasmids, and chromosomes.

The following are non-limiting embodiments of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A nucleic acid molecule may also comprise modified nucleic acid molecules, such as methylated nucleic acid molecules and nucleic acid molecule analogs. Analogs of purines and pyrimidines are known in the art. Nucleic acids may be naturally occurring, e.g. DNA or RNA, or may be synthetic analogs, as known in the art. Such analogs may be preferred for use as probes because of superior stability under assay conditions. Modifications in the native structure, including alterations in the backbone, sugars or heterocyclic bases, have been shown to increase intracellular stability and binding affinity. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2–5'-O-phosphonate and 3'-NH-5'-O-phosphoroamidate. Peptide nucleic acids replace the entire ribose phosphodiester backbone with a peptide linkage.

A DNA "coding sequence" is a DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and synthetic DNA sequences. A polyadenylation signal and transcription termination sequence may be located 3' to the coding sequence.

As used herein, the term "hybridization" refers to the process of association of two nucleic acid strands to form an antiparallel duplex stabilized by means of hydrogen bonding between residues of the opposite nucleic acid strands.

A polynucleotide or polypeptide has a certain percent "sequence identity" to another polynucleotide or polypeptide, meaning that, when aligned, that percentage of bases or amino acids are the same when comparing the two sequences. Sequence similarity can be determined in a number of different manners. To determine sequence identity, sequences can be aligned using the methods and computer programs, including BLAST, available over the world wide web at ncbi.nlm.nih.gov/BLAST. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See *Meth. Mol. Biol.* 70: 173–187 (1997). Also, the GAP program using the Needleman and Wunsch alignment method can be utilized to align sequences. See *J. Mol. Biol.* 48: 443–453 (1970)

Of interest is the BestFit program using the local homology algorithm of Smith Waterman (Advances in Applied Mathematics 2: 482–489 (1981) to determine sequence identity. The gap generation penalty will generally range from 1 to 5, usually 2 to 4 and in many embodiments will be 3. The gap extension penalty will generally range from about 0.01 to 0.20 and in many instances will be 0.10. The program has default parameters determined by the sequences inputted to be compared. Preferably, the sequence identity is determined using the default parameters determined by the program. This program is available also from Genetics Computing Group (GCG) package, from Madison, Wis., USA.

Another program of interest is the FastDB algorithm. FastDB is described in Current Methods in Sequence Comparison and Analysis, Macromolecule Sequencing and Synthesis, Selected Methods and Applications, pp. 127–149, 1988, Alan R. Liss, Inc. Percent sequence identity is calculated by FastDB based upon the following parameters:

| | |
|---|---|
| Mismatch Penalty: | 1.00; |
| Gap Penalty: | 1.00; |
| Gap Size Penalty: | 0.33; and |
| Joining Penalty: | 30.0. |

One parameter for determining percent sequence identity is the "percentage of the alignment region length" where the strongest alignment is found.

The percentage of the alignment region length is calculated by counting the number of residues of the individual sequence found in the region of strongest alignment. This number is divided by the total residue length of the target or query polynucleotide sequence to find a percentage. An example is shown below:

```
Target sequence:  GCGCGAAATACTCACTCGAGG   (SEQ ID NO:26)
                      ||| |||| |||
Query sequence:   TATAGCCCTAC.CACTAGAGTCC (SEQ ID NO:27)
                  1   5    10   15
```

The region of alignment begins at residue 9 and ends at residue 19. The total length of the target sequence is 20 residues. The percent of the alignment region length is 11 divided by 20 or 55%, for example.

Percent sequence identity is calculated by counting the number of residue matches between the target and query polynucleotide sequence and dividing total number of matches by the number of residues of the target or query sequence found in the region of strongest alignment. For the example above, the percent identity would be 10 matches divided by 11 residues, or approximately, 90.9%.

The percent of the alignment region length is typically at least about 55% of total length of the sequence, more typically at least about 58%, and even more typically at least about 60% of the total residue length of the sequence. Usually, percent length of the alignment region can be as great as about 62%, more usually as great as about 64% and even more usually as great as about 66%.

The term "oligonucleotide" refers to a short (under 100 bases in length) nucleic acid molecule.

The terms "DNA regulatory sequences", and "regulatory elements", used interchangeably herein, refer to transcriptional and translational control sequences, such as promoters, enhancers, polyadenylation signals, terminators, protein degradation signals, and the like, that provide for and/or regulate expression of a coding sequence and/or production of an encoded polypeptide in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding regions responsible for the binding of RNA polymerase. Eukaryotic promoters will often, but not always, contain "TATA" boxes and "CAT" boxes. Various promoters, including inducible promoters, may be used to drive expression.

A cell has been "transformed" or "transfected" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA.

A "clone" is a population of cells derived from a single cell or common ancestor by mitosis. A "cell line" is a clone of a primary cell that is capable of stable growth in vitro for many generations.

A "heterologous" region of the DNA construct is an identifiable segment of DNA within a larger DNA molecule that is not found in association with the larger molecule in nature. Thus, e.g., when the heterologous region encodes a mammalian gene, the gene will usually be flanked by DNA that does not flank the mammalian genomic DNA in the genome of the source organism. In another example, heterologous DNA includes coding sequence in a construct where portions of genes from two different sources have been brought together so as to produce a fusion protein product. Allelic variations or naturally-occurring mutational events do not give rise to a heterologous region of DNA as defined herein.

As used herein, the term "reporter gene" refers to a coding sequence attached to heterologous promoter or enhancer elements and whose product may be assayed easily and quantifiably when the construct is introduced into tissues or cells.

The amino acids described herein are preferred to be in the "L" isomeric form. The amino acid sequences are given in one-letter code (A: alanine; C: cysteine; D: aspartic acid; E: glutamic acid; F: phenylalanine; G: glycine; H: histidine; I: isoleucine; K: lysine; L: leucine; M: methionine; N: asparagine; P: proline; Q: glutamine; R: arginine; S: serine; T: threonine; V: valine; W: tryptophan; Y: tyrosine; X: any residue). $NH_2$ refers to the free amino group present at the amino terminus of a polypeptide. COOH refers to the free carboxyl group present at the carboxyl terminus of a polypeptide. In keeping with standard polypeptide nomenclature, *J Biol. Chem.*, 243 (1969), 3552–59 is used.

The term "immunologically active" defines the capability of the natural, recombinant or synthetic chromo/fluorescent protein, or any oligopeptide thereof, to induce a specific immune response in appropriate animals or cells and to bind with specific antibodies. As used herein, "antigenic amino acid sequence" means an amino acid sequence that, either alone or in association with a carrier molecule, can elicit an antibody response in a mammal. The term "specific binding," in the context of antibody binding to an antigen, is a term well understood in the art and refers to binding of an antibody to the antigen to which the antibody was raised, but not other, unrelated antigens.

A "host cell", as used herein, denotes microorganisms or eukaryotic cells or cell lines cultured as unicellular entities which can be, or have been, used as recipients for recombinant vectors or other transfer polynucleotides, and include the progeny of the original cell which has been transfected. It is understood that the progeny of a single cell may not necessarily be completely identical in morphology or in genomic or total DNA complement as the original parent, due to natural, accidental, or deliberate mutation.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a protein" includes a plurality of such proteins and reference to "the labeling method" includes reference to one or more labeling methods and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. (1985)); "Transcription and Translation" (B. D. Hames & S. J. Higgins eds. (1984)); "Animal Cell Culture" (R. I. Freshney, ed. (1986)); "Immobilized Cells and Enzymes" (IRL Press, (1986)); B. Perbal, "A Practical Guide To Molecular Cloning" (1984).

DETAILED DESCRIPTION OF THE INVENTION

The present invention provides fluorescent timer proteins, nucleic acid molecules encoding the proteins, and methods of using the proteins. The subject fluorescent timer proteins undergo a spectral shift over time after synthesis, and thus serve as "clocks" to track the amount of time elapsed after synthesis of a protein. The subject timer proteins are useful in a variety of applications, e.g., monitoring temporal aspects of promoter activity, protein trafficking, and protein stability.

Protein/Polypeptide Compositions

The present invention provides fluorescent timer proteins, as well as polypeptide compositions related thereto. The term polypeptide composition as used herein refers to both the full-length protein, as well as portions or fragments thereof. Also included in this term are variants of the naturally occurring protein, where such variants are homologous or substantially similar to the naturally occurring protein, as described in greater detail below.

The subject fluorescent timer proteins exhibit fluorescence, by which is meant that they can be excited at one wavelength of light following which they will emit light at another wavelength. In addition, the subject fluorescent timer proteins undergo a spectral shift over time after synthesis, i.e., the excitation wavelength and the emission wavelength change over time. This phenomenon is referred to as "the timer phenotype," and the subject proteins that exhibit the timer phenotype are referred to as "fluorescent timer proteins." A fluorescent timer protein of the subject invention has an emission spectrum that changes over time from a first wavelength to at least a second wavelength. At a first time, e.g., at the time of synthesis of the timer protein, the protein emits at a first wavelength. At a time after emission at the first wavelength begins (e.g., "a second time"), the timer protein begins to emit at a second wavelength of light which is different from the first wavelength and which can be distinguished from the first wavelength. The time after synthesis at which a subject protein emits at the first and the second wavelengths (and possibly additional wavelengths) of light is a characteristic of the protein.

In some embodiments, a fluorescent timer protein emits, in succession, at a first wavelength, a second wavelength, a third wavelength, and possibly additional wavelengths. In the following discussion of fluorescent timer protein properties, various parameters relating to changes in spectral properties, e.g., the amount of time elapsed between beginning of emission at a first wavelength to the beginning of emission at a second wavelength, also apply to changes in spectral properties at second, third, fourth, fifth, and possibly subsequent wavelengths.

In some embodiments, a subject timer protein is used as a single molecule. In these embodiments, emission shifts from a first wavelength to at least a second wavelength in a matter of seconds or less. In other embodiments, a population of timer proteins is used. In these embodiments, individual timer proteins in a population of timer proteins typically do not undergo a spectral shift simultaneously.

Instead, individual members of a population undergo a spectral shift over a period of time. The discussion of the properties of timer protein that follows applies generally to populations of timer protein, but can also apply to single timer protein molecules as well.

As used herein, the term "wavelength" refers to a discrete spectrum of wavelengths. For example, a particular timer protein that is said to emit at a first wavelength of about 500 nm and a second wavelength of about 580 nm may actually emit initially at from about 480 nm to about 520 nm, and, over time, emit at from about 560 to about 600 nm.

A lag time of seconds, minutes, hours, or days may exist between synthesis of the protein and emission at the first wavelength. The time which elapses between synthesis and emission at the first wavelength is from about 1 second to about 60 seconds, from about 1 minute to about 15 minutes, from about 15 minutes to about 30 minutes, from about 30 minutes to about 60 minutes, from about 1 hour to about 2 hours, from about 2 hours to about 4 hours, from about 4 hours to about 8 hours, from about 8 hours to about 12 hours, from about 12 hours to about 16 hours, from about 16 hours to about 24 hours, from about 1 day to about 1.5 days, from about 1.5 days to about 2 days, from about 2 days to about 3 days, from about 3 days to about 4 days, or longer. Timer proteins having a shorter or longer lag period between synthesis and emission at a first wavelength are advantageous in specific applications.

The amount of time which elapses between the start of emission at the first wavelength and the start of emission at the second wavelength (e.g., the difference between the first time and the second time) is from about 1 second to about 30 seconds, from about 30 seconds to about 60 seconds, from about 1 minute to about 15 minutes, from about 15 minutes to about 30 minutes, from about 30 minutes to about 60 minutes, from about 1 hour to about 2 hours, from about 2 hours to about 4 hours, from about 4 hours to about 8 hours, from about 8 hours to about 12 hours, from about 12 hours to about 16 hours, from about 16 hours to about 24 hours, from about 1 day to about 1.5 days, from about 1.5 days to about 2 days, from about 2 days to about 3 days, from about 3 days to about 4 days, from about 4 days to about 7 days, from about 1 week to about 2 weeks, or longer. The aforementioned elapsed time also applies to the time that elapses between the start of emission at the second wavelength and a third wavelength (or the third wavelength and the fourth wavelength, etc.).

In general, each timer protein is calibrated, such that the lag time between synthesis and emission at the first wavelength, the amount of time that elapses between the start of emission at the first wavelength and the start of emission at the second wavelength (and between the start of emission at the second wavelength and a third wavelength, etc.) for a given timer protein is known. The change in fluorescence intensity at each wavelength is plotted versus time following synthesis. For some applications, the ratio of fluorescence intensity at a first wavelength to the fluorescence intensity at a second wavelength is plotted versus time following synthesis. Calibration of a timer protein provides information about the temporal aspects of its spectral properties, which information can be used in various applications, such as determining the amount of time elapsed from synthesis of a protein, determining the time elapsed from synthesis of a protein to degradation of the protein, determining the amount of time elapsed from activation of a promoter or inactivation of a promoter. Typically, a protein is calibrated in a given cell type (e.g., 293 cells) at a particular temperature. In some embodiments, the spectral properties of a timer protein are temperature dependent. In these embodiments, the timer protein is calibrated at various temperatures. In other embodiments, the spectral properties may depend on other factors such as pH, the presence in a cell of a particular chaperone protein, and the like. In these embodiments, calibration is conducted under conditions that are of interest.

The change in the spectral properties over time can be expressed as the ratio of fluorescence (e.g., fluorescence intensity) at the first wavelength to fluorescence at the second wavelength over time. In some embodiments, the ratio of fluorescence at the first wavelength to fluorescence at the second wavelength ("the ratio") varies from about 200:1 to about 1:200, from about 150:1 to about 1:150, from about 100:1 to about 1:100, from about 50:1 to about 1:50, from about 25:1 to about 1:25, or from about 10:1 to about 1:10 overtime. In many embodiments, the change in the ratio is linear over time. In these embodiments, once change in the ratio versus time for a given protein is known, the ratio at any given time can be used to calculate the amount of time elapsed from synthesis of the protein.

In particular embodiments of interest, the linear ratio versus time relationship for a given protein is substantially the same in a variety of cell types in which the subject timer protein is synthesized. For example, the linear ratio versus time relationship is substantially the same in a prokaryotic cell and a eukaryotic cell; among different cell types within a multicellular organism; and the like. In some embodiments, the slope of the linear ratio versus time relationship varies from cell type to cell type.

The duration of emission at a given wavelength that is any wavelength except the final wavelength is generally from about 10 minutes to about 24 hours, from about 30 minutes to about 20 hours, from about 1 hour to about 12 hours, from about 3 hours to about 9 hours, or from about 4 hours to about 7 hours. Thus, a subject fluorescent timer protein fluoresces at a first wavelength for a first period of time, and at a second wavelength for a second period of time. The duration of emission at the final wavelength is generally from the beginning of emission at that wavelength through the remaining life of the protein, e.g., until the protein is degraded, denatured, unfolded, or otherwise ceases to fluoresce. In a population of timer proteins, the majority (typically more than about 90%) of the members of the population undergoes a spectral shift.

In some embodiments, emission at the first wavelength and the second wavelength is overlapping. For example, a timer protein population may emit at about 500 nm from time zero to about 10 hours, and may emit at about 580 nm from about 8 hours to about 20 hours. Thus, in these embodiments, the protein population emits at two different wavelengths for a period of time.

In some embodiments of interest, the linear ratio versus time relationship for a given protein is substantially the same over a range of temperatures from about 4° C. to about 70° C., from about 15° C. to about 65° C., from about 20° C. to about 60° C., or from about 37° C. to about 50° C.

In other embodiments, one or more of the spectral properties, including the lag time between synthesis of the protein and emission at a first wavelength, and the amount of time elapsed between the start of emission at a first wavelength and beginning of emission at a second wavelength, is temperature dependent.

The excitation of the subject proteins typically occurs at a wavelength in the range of from about 250 to 750, usually from about 500 to 600 and more usually from about 540 to 580 nm. Excitation can also be achieved using ultraviolet light.

The emitted wavelengths are in the visible spectrum, e.g., red, orange, yellow, green, blue, indigo, and violet; ultraviolet light; and infrared light. Thus, in many embodiments, the emission spectrum is in the range of from about 200 nm to about 300 nm, from about 300 nm to about 400 nm, from about 380 nm to about 400 nm, from about 400 nm to about 430 nm, from about 430 nm to about 500 nm, from about 500 m to about 560 nm, from about 560 nm to about 620 nm, from about 620 nm to about 700 nm, from about 700 nm to about 1.5 sum, from about 1.5 µm to about 20 µm, or from about 20 µm to about 1000 µm.

The difference between any two emissions (e.g., between the first wavelength and the second wavelength) varies, but is generally from about 10 nm to about 15 nm, from about 15 nm to about 20 nm, from about 20 nm to about 25 nm, from about 25 nm to about 30 nm, from about 30 nm to about 35 nm, from about 35 nm to about 40 nm, from about 40 nm to about 45 nm, from about 45 nm to about 50 nm, from about 50 nm to about 55 nm, from about 55 nm to about 60 nm, from about 60 nm to about 65 nm, from about 65 nm to about 70 nm, from about 70 nm to about 75 nm, from about 75 m to about 80 nm, from about 80 nm to about 85 nm, from about 85 m to about 90 nm, from about 90 nm to about 95 nm, from about 95 nm to about 100 nm, from about 100 nm to about 120 nm, from about 120 nm to about 140 nm, from about 140 nm to about 160 nm, from about 160 nm to about 180 nm, or from about 180 nm to about 200 nm, or more.

Emission can be detected, and the various emission wavelengths can be distinguished, using any known means, using e.g., a fluorescent microscope, a laser confocal microscope, a fluorescent plate reader, a flow cytometry apparatus (e.g., a fluorescence-activated cell sorter), and the like. For example, filters can be used to visualize a particular range of wavelengths. For example, a fluorescein isothiocyanate (FITC) filter can be used to visualize fluorescence in the green range (500–560 nm); a phycoerythirin (PE) filter can be used to visualize fluorescence in the red range (620–700 nm).

Fluorescent timer proteins are derived from natural sources, including, but not limited to, members of the phylum Cnidaria. Cnidarians include anthozoan species (which are, in many embodiments, non-luminescent species, i.e., non-bioluminescent species), scyphozoan species, and hydrozoan species. Specific proteins of interest are fluorescent timer proteins from the following specific anthozoa species: *Anemonia majano, Clavularia* sp., *Zoanthus* sp., *Discosoma striata, Discosoma* sp. "red". *Anemonia sulcata, Discosoma* sp., *Discosoma* sp "green", *Discosoma* sp. "magenta," *Heteractis* sp., e.g., *Heteractis crispa*, and *Condylactis* sp., e.g., *Condylactis gigantea*. In certain embodiments, the organism is *Discosoma* sp. "red". In addition, fluorescent timer proteins include variants of naturally-occurring proteins, including mutants of naturally-occurring proteins made using site-directed and/or random mutagenesis, as well as variants of such mutants, and fusion proteins including a timer fluorescent protein.

In one particular embodiment, a subject fluorescent timer protein is designated E5 and has an amino acid sequence as shown in FIG. 2B and identified as SEQ ID NO:04. E5 differs in amino acid sequence from the wild-type Anthozoa protein drFP583 by a Val-to-Ala substitution at amino acid 105 (V105A) and a Ser-to-Thr substitution at amino acid 197 (S 197T). The nucleotide sequence of E5 is "humanized" i.e., the nucleotide sequence reflects preferred codon usage in humans. The nucleotide sequence encoding E5 is shown in FIG. 2 and is identified as SEQ ID NO:03. E5 emits first at between 350 and 400 nm, then emits at about 500 nm (green fluorescence), then emits at about 580 nm (red fluorescence), over time.

A single amino acid substitution in drFP583, i.e., a Ser-to-Thr substitution at amino acid 197, results in a protein that undergoes a spectral shift. $Ser^{197}$ in drFP583 is analogous to $Thr^{203}$ in green fluorescent protein from *Aequorea victoria*. Any fluorescent protein having a substitution of $S^{197}$ or its counterpart, wherein the amino acid substitution results in a spectral shift, is encompassed by the term "fluorescent timer protein." In some embodiments, a timer protein contains a Ser-to-Thr substitution at amino acid 197 (or its counterpart). Other amino acid substitutions of interest include a substitution of $Ser^{197}$ or its counterpart with glycine, asparagine, glutamine, aspartic acid, or glutamic acid.

In many embodiments, mutations of amino acids that are in direct contact with the fluorophore result in the timer phenotype. Determination of which amino acid in a given fluorescent protein is a counterpart to $S^{197}$ of drFP583, and determination of amino acids that are in direct contact with the fluorophore is readily achieved by those skilled in the art. An example of how one makes such a determination is described in Ormö et al. (1996) *Science* 273:1392. In general, modeling of a given fluorescent protein on the basis of the crystal structure of a known fluorescent protein, such as *A. victoria* GFP, allows one to determine which amino acid is a counterpart of $S^{197}$ of drFP583, and which amino acids contact the fluorophore. In addition, alignment of the amino acid sequence of a given protein with drFP583 allows determination of the counterpart in that protein of $S^{197}$.

In other embodiments of interest, a subject fluorescent timer protein exhibits a shorter elapsed time between fluorescence at a first wavelength and fluorescence at a second wavelength, as compared to a reference protein. For example, of particular interest in many embodiments are mutants of E5 that exhibit a shorter elapsed time between green fluorescence and red fluorescence. Mutants are generated by random mutagenesis, or by site-directed mutagenesis. As non-limiting examples, site-directed mutagenesis is carried out to generate one or more of the following amino acid substitutions: I161T, N42H, Y120H, and V71M. Mutants that display a shorter elapsed time between emission at a first wavelength and emission at a second wavelength are identified by measuring the spectral shift over time, using methods described above.

The subject proteins typically range in length from about 200 to 250, usually from about 220 to 240 amino acid residues, and generally have a molecular weight ranging from about 20 to 30, usually from about 22.50 to 27.50 kDa. In some embodiments, the fluorescent timer protein is part of a larger macromolecule (e.g., is part of a larger protein) that has a molecular weight greater than about 27.50 kDa. In these embodiments, the portion of the larger protein that exhibits the timer phenotype is in the range of from about 200 to 250 amino acids long and from about 22.50 to about 27.50 kDa.

Subject fluorescent timer proteins are typically tetrameric proteins, but in some embodiments are dimers or monomers. Without wishing to be bound by any one theory, it is believed that amino acid side chains of the fluorophore of the monomeric subunits are responsible for fluorescence, and that a cyclization step followed by a first oxidation of the fluorophore initiates fluorescence, while an isomerization step and a second oxidation step are required for the spectral shift. Furthermore, without wishing to be bound by theory, it is believed that individual subunits of a tetramer or a dimer can undergo a spectral shift independently of the other subunits.

In some embodiments, a subject fluorescent timer protein forms higher order aggregates. In other embodiments, a subject timer protein is a non-aggregating variant. As used herein, an "aggregate" refers to a higher order molecular complex, e.g., a complex that comprises two or more tetramers of the protein.

Of particular interest in many embodiments are mutants that show decreased aggregation in vitro relative to drFP583, or relative to E5. Such mutants are referred to as "non-aggregating timer proteins." "Reduced aggregation in vitro" refers to reduced aggregation in a cell-free system or in solution. In some embodiments, a non-aggregating timer protein shows less than about 90%, less than about 80%, less than about 70%, less than about 60%, less than about 50%, less than about 40%, less than about 30%, less than about 25%, less than about 20%, less than about 15%, less than about 10%, or less than about 5% of the aggregation shown by E5 under the same in vitro conditions, e.g., less than about 60%, less than about 50%, less than about 40%, less than about 30%, less than about 20%, less than about 10%, or less than about 5%, of the timer protein present in a sample is aggregated.

In some embodiments, a non-aggregating timer protein of the invention is present in vitro as a non-aggregated multimer. In these embodiments, more than about 40%, more than about 50%, more than about 60%, more than 70%, more than about 80%, more than about 90%, or more than about 95% of the timer protein in a sample is present as a multimer, e.g., a dimer, a trimer, a tetramer. In other embodiments, a non-aggregating timer protein of the invention is present in vitro as a monomer. In these embodiments, more than about 40%, more than about 50%, more than about 60%, more than 70%, more than about 80%, more than about 90%, or more than about 95% of the non-aggregating timer protein in a sample is present as a monomer.

In some embodiments, a subject non-aggregating timer protein exhibits reduced aggregation in vivo. "Reduced aggregation in vivo" refers to reduced aggregation in a cell. In some embodiments, a non-aggregating timer protein shows less than about 90%, less than about 80%, less than about 70%, less than about 60%, less than about 50%, less than about 40%, less than about 30%, less than about 25%, less than about 20%, less than about 15%, less than about 10%, or less than about 5% of the aggregation shown by drFP583 or E5 under the same in vivo conditions, e.g., in another eukaryotic cell from the same cell line, in an identical prokaryotic cell, or in a eukaryotic cell or cell population of the same cell type. In general, less than about 60%, less than about 50%, less than about 40%, less than about 30%, less than about 20%, less than about 10%, or less than about 5%, of a non-aggregating timer protein present in a cell or a cell population is aggregated.

In some embodiments, a non-aggregating timer protein of the invention is present in a cell as a non-aggregated multimer. In these embodiments, more than about 40%, more than about 50%, more than about 60%, more than 70%, more than about 80%, more than about 90%, or more than about 95% of the non-aggregating timer protein in a cell or a cell population is present as a multimer, e.g., a tetramer. In other embodiments a non-aggregating timer protein of the invention is present in a cell as a monomer. In these embodiments, more than about 40%, more than about 50%, more than about 60%, more than 70%, more than about 80%, more than about 90%, or more than about 95% of the non-aggregating timer protein in a cell or a cell population is present as a monomer.

In vitro conditions suitable for comparing an aggregating protein such as drFP583 or E5 and a subject non-aggregating timer protein are conditions that do not prevent aggregation of the protein, e.g., standard physiological conditions. Any of a wide variety of buffer systems used in the art to study physiological phenomena can be used for in vitro comparisons. Non-limiting examples of such conditions include, but are not limited to, a salt concentration in the range of from about 0.01 mM to about 0.1 mM; a temperature in the range of from about 19° C. to about 25° C.; and a pH in the range of from about 6.5 to about 8.0. Buffers that are suitable for comparison of aggregation include, but are not limited to, any physiological buffer; Tris-Cl, phosphate buffered saline; Tris buffered saline; borate buffered saline; and the like. An example is 1×Tris-Ci buffer, pH 8.8, 0.1% SDS, room temperature. For example, a standard sodium dodecyl sulfate-polyacrylamide gel electrophoresis (SDS-PAGE) protocol is used to separate proteins produced recombinantly in a bacterial cell, e.g., E. coli. Samples are not boiled before loading onto the gel. Standard conditions for SDS-PAGE are described in Short Protocols in Molecular Biology, 4$^{th}$ Ed. 1999, F M Ausubel et al., eds., John Wiley & Sons, Inc. Typically, samples are electrophoresed in the presence of about 0.1% SDS in 1×Tris-Cl buffer (pH about 8.8).

Methods of measuring the degree of aggregation are known in the art; any known method can be used to determine whether a given mutant shows a reduction in aggregation, e.g., when compared to dsFP583 or when compared to E5. Such methods include, but are not limited to, gel filtration; ultracentrifugation; circular dichroism; and light scattering.

A specific non-aggregating timer protein of interest has the following amino acid substitutions compared to E5 (i.e., compared to SEQ ID NO:04): an Arg-to-Ala substitution at amino acid 2; a Lys-to-Glu substitution at amino acid 5; and a Lys-to-Thr substitution at amino acid 9. This mutant, referred to herein as "E5NA," has the same spectral properties as E5. E5NA has the amino acid sequence set forth in SEQ ID NO:06, and is encoded by the nucleotide sequence set forth in SEQ ID NO:05.

Any other non-aggregating timer proteins containing amino acid substitutions, and/or deletions, and/or insertions that give rise to a non-aggregating timer protein with one or more of the above-described characteristics (e.g., reduced aggregation in vivo, reduced aggregation in vitro, etc.) are encompassed by the term "non-aggregating timer protein." In general, a non-aggregating timer protein that is derived from an aggregating timer protein, e.g., by site-directed or random mutagenesis of a nucleic acid molecule encoding all or part of an aggregating timer protein, displays substantially the same spectral properties as the aggregating timer protein from which it was derived.

Homologs or proteins (or fragments thereof) that vary in sequence from the sequence of the E5 protein are also provided. By homolog is meant a protein having at least about 35%, usually at least about 40% and more usually at least about 60% amino acid sequence identity to the E5 protein, as determined using MegAlign, DNAstar (1998) clustal algorithm as described in D. G. Higgins and P. M. Sharp, "Fast and Sensitive multiple Sequence Alignments on a Microcomputer," (1989) CABIOS, 5: 151–153. (Parameters used are ktuple 1, gap penalty 3, window, 5 and diagonals saved 5). In many embodiments, homologues of interest have much higher sequence identify, e.g., 65%, 70%, 75%, 80%, 85%, 90% or higher.

Also provided are proteins that are substantially identical to the E5 protein, where by substantially identical is meant that the protein has an amino acid sequence identity to the sequence of wild type protein of at least about 60%, usually at least about 65% and more usually at least about 70%, where in some instances the identity may be much higher, e.g., 75%, 80%, 85%, 90%, 95%, 98%, or higher.

The proteins of the subject invention are present in a non-naturally occurring environment, e.g., are separated from their naturally occurring environment. In certain embodiments, the subject proteins are present in a composition that is enriched for the subject protein as compared to its naturally occurring environment, or from the environment in which it was synthesized. For example, purified protein is provided, where by purified is meant that the protein is present in a composition that is substantially free of proteins other than a fluorescent timer protein, where by substantially free is meant that less than 90%, usually less than 60% and more usually less than 50%, e.g., less than 40%, less than 30%, less than 25%, less than 20%, less than 15%, less than 10%, or less than 5%, of the composition is made up of proteins other than fluorescent timer proteins.

The proteins of the subject invention may also be present as an isolate, by which is meant that the protein is substantially free of other proteins and other naturally occurring biologic molecules, such as oligosaccharides, lipids, polynucleotides and fragments thereof, and the like, where the term "substantially free" in this instance means that less than 80%, less than 70%, usually less than 60% and more usually less than 50%, e.g., less than 40%, less than 30%, less than 25%, less than 20%, less than 15%, less than 10%, or less than 5%, of the composition containing the isolated protein is some other naturally occurring biological molecule. In certain embodiments, the proteins are present in substantially pure form, where by "substantially pure form" is meant at least 95%, usually at least 97% and more usually at least 99% pure. Concentration of a fluorescent timer protein in a sample is expressed as weight/volume.

Fragments of fluorescent timer proteins are also provided. In some embodiments, a fluorescent timer protein includes at least about 4 amino acids, at least about 15, at least about 25, at least about 50, at least about 75, at least about 100, at least about 125, at least about 150, at least about 175, at least about 200, or at least about 220, contiguous amino acids of the sequence set forth in SEQ ID NOS:04 or :06, up to the entire sequence set forth in SEQ ID NO:04 or :06. In other embodiments, a fluorescent timer protein includes fragments of at least about 4, at least about 15, at least about 25, at least about 50, at least about 75, at least about 100, at least about 125, at least about 150, at least about 175, at least about 200, or at least about 220 contiguous amino acids of a protein that shares at least about 60%, at least about 65%, at least about 70%, at least about 75%, at least about 80%, at least about 85%, at least about 90%, or at least about 95%, with the amino acid sequence set forth in SEQ ID NO:04 or :06.

In addition to the E5 and E5NA proteins described above, variant proteins are also provided. Generally such polypeptides include an amino acid sequence encoded by an open reading frame (ORF) of the gene encoding a fluorescent timer protein, including the full length protein and fragments thereof, particularly biologically active fragments and/or fragments corresponding to functional domains, e.g., a fluorophore domain (e.g., amino acids 66, 67, and 68), and the like; including fusions of the subject polypeptides to other proteins or parts thereof; and including variants with conserved amino acid substitutions. Conserved amino acid substitutions include, but are not limited to, alanine-to-valine, leucine-to-isoleucine, serine-to-threonine, asparagine-to-glutamine, lysine-to-arginine, aspartic acid-to-glutamic acid, and vice versa; and the like.

Fragments of interest will typically be at least about 4 amino acids (aa), at least about 10 aa in length, usually at least about 50 aa in length, and may be as long as 300 aa in length or longer, but will usually not exceed about 1000 aa in length, where the fragment will have a stretch of amino acids that is identical to the subject protein of at least about 10 aa, and usually at least about 15 aa, and in many embodiments at least about 50 aa in length.

Also provided are fusion proteins, i.e., a subject fluorescent timer protein, or fragment thereof, which is fused to a second protein. In many embodiments, fusion proteins comprise a subject fluorescent timer protein, or fragment thereof, and a non-fluorescent polypeptide ("the fusion partner") fused in-frame at the N-terminus and/or C-terminus of the subject polypeptide. Fusion partners include, but are not limited to, any polypeptide whose stability and/or position within a cell is being monitored; structural proteins; regulatory proteins; polypeptides that provide a catalytic function; polypeptides that induce a cellular response; ligands or receptors or mimetics thereof, polypeptides that can bind antibody specific to the fusion partner (e.g., epitope tags); and antibodies or binding fragments thereof.

In some embodiments, a subject fluorescent timer protein, or a subject fusion protein, further includes additional peptides or amino acid sequences, including, but not limited to, a peptide that provides for localization to a particular subcellular organelle; a peptide that provides for degradation of the protein; a peptide that provides for insertion into a membrane; a peptide that provides for secretion of the protein from the cell, and the like. Peptides that provide for localization to a particular subcellular organelle include, but are not limited to, a nuclear localization signal (NLS); nuclear export signals, and the like.

NLSs include PKKKRKV (SEQ ID NO:7) and KKKRKVC (SEQ ID NO:8) (Kalderon et al. (1984) Cell 39:499); GKKRSKA (SEQ ID NO:9) (Moreland et al. (1987) Mol. Cell. Biol. 7:4048); KRPRP (SEQ ID NO: 10) (Lyons et al. (1987) Mol. Cell. Biol. 7:2451); GNKAKRQRST (SEQ ID NO:11) (Gilmore et al. (1988) J. Virol. 62:703); GGAAKRVKLD (SEQ ID NO:12) (Chelsky et al. (1989) Mol. Cell. Biol. 9:2487); SALIKKKKKMAP (SEQ ID NO: 13) (Van Etten et al. (1989) Cell 58:669); RKLKKLGN (SEQ ID NO: 14) (Guiochon-Mantel et al. (1989) Cell 57:1147); PQPKKKP (SEQ ID NO: 15) (Dang et al. (1989) J. Biol. Chem. 264:18019); ASKSRKRKL (SEQ ID NO:16) (Chida et al. (1992) Proc. Natl. Acad. Sci. USA 89:4290); KKKYK (SEQ ID NO:17) and KKKYKC (SEQ ID NO:18), (Bukrinsky et al. (1993) Nature 365:666); KSKKK (SEQ ID NO:19) (Bukrinsky et al. (1993), supra); and AKRVKL (SEQ ID NO:20) and KRVKLC (SEQ ID NO:21) (Chelsky et al. (1989), supra). Additional examples of nuclear localization signals include RRMKWKK (SEQ ID NO:22) (Moede et al. (1999) *FEBS Lett.* 461:229–234; and nuclear localization signals described in Boulikas (1993) *Crit. Rev. Eukaryot. Gene Expr.* 3:193–227; Hsieh et al. (1998) *J. Cell. Biochem.* 70:94–109; Truant and Cullen (1999) *Mol. Cell. Biol.* 19:1210–1217; and Irie et al. (2000) *J. Biol. Chem.* 275:2647–2653.

Degradation signals include, but are not limited to, a cyclin B1 degradation box (CDB); a PEST sequence from the ornithine decarboxylase (ODC) gene (Olmo et al. (1999) *Biochem. Biophys. Res. Comm.* 257:269–272); N-terminal amino acids (e.g., 1–33) from stearoyl-CoA desaturase (Mziant et al. (2000) *Proc. Natl. Acad. Sci. USA* 97:8883–8888); a KEN box (Pfleger and Kirscher (2000) *Genes Dev.* 14:655–665); a D-box (Pfleger and Kirscher (2000) *Genes Dev.* 14:655–665); an F-box (Craig and Tyler (1999) *Prog. Biophys. Mol. Biol.* 72:299–328; Galan and Peter (1999) *Proc. Natl. Acad. Sci. USA* 96:9124–9129), e.g., the F-box of Cdc4p (Mathias et al. (1999) *Mol. Cell Biol.* 19:1759–1767); and the like.

The subject proteins and polypeptides may be obtained from naturally occurring sources or synthetically produced. For example, wild type proteins may be derived from biological sources which express the proteins, e.g., phylum Cnidaria. The subject proteins may also be derived from synthetic means, e.g. by expressing a recombinant gene encoding protein of interest in a suitable host, as described above. Any convenient protein purification procedures may be employed, where suitable protein purification methodologies are described in Guide to Protein Purification, (Deuthser ed.) (Academic Press, 1990). For example, a lysate may be prepared from the original source and purified using HPLC, exclusion chromatography, gel electrophoresis, affinity chromatography, and the like.

In certain embodiments, the present invention is directed to an isolated and purified fluorescent timer protein selected from the group consisting of: (a) an isolated protein encoded by a nucleic acid molecule which encodes a fluorescent timer protein wherein the nucleic acid molecule is from an organism from phylum Cnidaria and wherein the organism does not exhibit bioluminescence; (b) an isolated protein encoded by a nucleic acid molecule which hybridizes to isolated nucleic acid molecule of (a); and (c) an isolated protein encoded by a nucleic acid molecule differing from the isolated nucleic acid molecules of (a) and (b) in codon sequence due to degeneracy of the genetic code. In certain embodiments, the isolated and purified fluorescent protein is E5 or a variant thereof Nucleic Acid Compositions The subject invention provides nucleic acid compositions encoding fluorescent timer proteins or fragments thereof, as well as the homologues thereof. By nucleic acid composition is meant a composition comprising a sequence of a nucleic acid molecule having an open reading frame that encodes a fluorescent timer polypeptide of the subject invention, i.e., fluorescent timer protein gene, and is capable, under appropriate conditions, of being expressed as a fluorescent timer protein. Also encompassed in this term are nucleic acids that are homologous or substantially similar or identical to the nucleic acids encoding fluorescent timer proteins. Thus, the subject invention provides genes encoding the fluorescent timer proteins of the subject invention and homologs thereof.

In many embodiments, the organism from which the subject fluorescent timer proteins of the present invention are derived is an organism from members of the phylum Cnidaria. Cnidarians include anthozoan species, scyphozoan species, and hydrozoan species. Specific proteins of interest are fluorescent timer proteins from the following specific anthozoa species: *Anemonia majano, Clavularia* sp., *Zoanthus* sp., *Discosoma striata, Discosoma* sp. "red", *Anemonia sulcata* sp., *Discosoma* sp "green", *Discosoma* sp. "magenta," Heteractis sp., e.g., *Heteractis crispa*, and *Condylactis* sp., e.g., *Condylactis gigantea*. In certain embodiments, the organism is *Discosoma* sp. "red".

The fluorescent timer protein designated E5, which is a mutant of the humanized version of drFP583, as well as homologues and mutants of E5, are of particular interest in many embodiments.

The cDNA coding sequence and amino acid sequence for E5 are provided in SEQ ID NOs: 03 and 04, respectively, and are shown in FIG. 2. The cDNA coding sequence and amino acid sequence for a non-aggregating variant of E5 are provided in SEQ ID NOs:05 and :06, respectively, and are shown in FIG. 3.

In some embodiments, a subject nucleic acid molecule includes a nucleotide sequence that encodes at least about 5, at least about 6, at least about 10, at least about 15, at least about 25, at least about 50, at least about 100, at least about 125, at least about 150, at least about 175, at least about 200, or at least about 220, contiguous amino acids of the sequence set forth in SEQ ID NO:04 or SEQ ID NO:06. In a particular embodiment, a subject nucleic acid molecule includes a sequence that encodes the entire amino acid sequence set forth in SEQ ID NO:04 or :06.

In some embodiments, a subject nucleic acid molecule includes at least about 15, at least about 18, at least about 25, at least about 50, at least about 75, at least about 100, at least about 125, at least about 150, at least about 175, at least about 200, at least about 225, at least about 250, at least about 300, at least about 350, at least about 400, at least about 450, at least about 500, at least about 550, at least about 600, at least about 650, or at least about 690 contiguous nucleotides of the sequence set forth in SEQ ID NO:03 or :05. In one particular embodiment, a subject nucleic acid molecule includes the entire nucleotide sequence set forth in SEQ ID NO:03.

With respect to homologues of the subject nucleic acids, the source of homologous genes may be any species of plant or animal. Between closely related species, e.g., two different species of Anthozoa, homologs have substantial sequence similarity, e.g. at least 75% sequence identity, usually at least 90%, more usually at least 95% between nucleotide sequences. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990), *J. Mol. Biol.* 215:403–10 (using default settings, i.e. parameters w=4 and T=17). The sequences provided herein are essential for recognizing fluorescent timer protein related and homologous proteins, and the nucleic acids encoding the same, in database searches. Of particular interest in certain embodiments are nucleic acids of substantially the same length as the nucleic acid identified as SEQ ID NO:03 and have sequence identity to this sequence of at least about 90%, usually at least about 95% and more usually at least about 99% over the entire length of the nucleic acid.

Nucleic acids encoding the proteins and polypeptides of the subject invention may be cDNA or genomic DNA or a fragment thereof. The term "fluorescent timer protein gene," as used herein, refers to the open reading frame encoding specific fluorescent proteins and polypeptides, and introns, as well as adjacent 5' and 3' non-coding nucleotide sequences involved in the regulation of expression, up to about 20 kb beyond the coding region, but possibly further in either direction. The gene may be introduced into an appropriate vector for extrachromosomal maintenance or for integration into a host genome, as described in greater detail below.

The term "cDNA" as used herein is intended to include all nucleic acids that share the arrangement of sequence elements found in native mature mRNA species, where sequence elements are exons and 5' and 3' non-coding regions. Normally mRNA species have contiguous exons, with the intervening introns, when present, being removed by nuclear RNA splicing, to create a continuous open reading frame encoding the protein.

A genomic sequence of interest comprises the nucleic acid present between the initiation codon and the stop codon, as defined in the listed sequences, including all of the introns that are normally present in a native chromosome. It may further include 5' and 3' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence. The genomic DNA flanking the coding region, either 3' or 5', or internal regulatory sequences as sometimes found in introns, contains sequences required for proper tissue and stage specific expression.

The nucleic acid compositions of the subject invention may encode all or a part of the subject fluorescent proteins. Double or single stranded fragments may be obtained from the DNA sequence by chemically synthesizing oligonucleotides in accordance with conventional methods, by restriction enzyme digestion, by PCR amplification, etc. For the most part, DNA fragments will be of at least 15 nucleotides (nt), usually at least 18 nt or 25 nt, and may be at least about 50 nt.

The subject genes are isolated and obtained in substantial purity, generally as other than an intact chromosome. Usually, the DNA will be obtained substantially free of other nucleic acid sequences that do not include an Anthozoa fluorescent protein gene sequence or fragment thereof, generally being at least about 50%, usually at least about 90% pure and are typically "recombinant", i.e. flanked by one or more nucleotides with which it is not normally associated on a naturally occurring chromosome.

The subject polynucleotides (e.g., a polynucleotide having a sequence of SEQ ID NO:03 or :05), the corresponding cDNA, the full-length gene and constructs of the subject polynucleotides, as well as homologs and mutants thereof, are provided. These molecules can be generated synthetically by a number of different protocols known to those of skill in the art. Appropriate polynucleotide constructs are purified using standard recombinant DNA techniques as described in, for example, Sambrook et al., *Molecular Cloning: A Laboratory Manual*, $2^{nd}$ Ed., (1989) Cold Spring Harbor Press, Cold Spring Harbor, N.Y., and under current regulations described in United States Dept. of HHS, National Institute of Health (NIH) Guidelines for Recombinant DNA Research.

Also provided are nucleic acids that encode fusion proteins of the subject proteins, or fragments thereof, which are fused to a second protein, e.g., a degradation sequence, a signal peptide, etc. In many embodiments, fusion proteins comprise a subject polypeptide, or fragment thereof, and a non-fluorescent polypeptide ("the fusion partner") fused in-frame at the N-terminus and/or C-terminus of the subject polypeptide. Fusion partners include any polypeptide whose stability and/or position within a cell is being monitored; structural proteins; regulatory proteins; polypeptides that provide a catalytic function; polypeptides that induce a cellular response; ligands or receptors or mimetics thereof, polypeptides that can bind antibody specific to the fusion partner (e.g., epitope tags); antibodies or binding fragments thereof, subcellular localization signals; degradation signals; and the like.

Also provided are constructs comprising the subject nucleic acids inserted into a vector, where such constructs may be used for a number of different applications, including propagation, protein production, etc. Viral and non-viral vectors may be prepared and used, including plasmids. The choice of plasmid will depend on the type of cell in which propagation is desired and the purpose of propagation. Certain vectors are useful for amplifying and making large amounts of the desired DNA sequence. Other vectors are suitable for expression in cells in culture. Still other vectors are suitable for transfer and expression in cells in a whole animal or person. The choice of appropriate vector is well within the skill of the art. Many such vectors are available commercially. To prepare the constructs, the partial or full-length polynucleotide is inserted into a vector typically by means of DNA ligase attachment to a cleaved restriction enzyme site in the vector. Alternatively, the desired nucleotide sequence can be inserted by homologous recombination in vivo. Typically this is accomplished by attaching regions of homology to the vector on the flanks of the desired nucleotide sequence. Regions of homology are added by ligation of oligonucleotides, or by polymerase chain reaction using primers comprising both the region of homology and a portion of the desired nucleotide sequence, for example.

Also provided are expression cassettes or systems that find use in, among other applications, the synthesis of the subject proteins. For expression, the gene product encoded by a polynucleotide of the invention is expressed in any convenient expression system, including, for example, bacterial, yeast, insect, amphibian, and mammalian systems. Suitable vectors and host cells are described in U.S. Pat. No. 5,654,173. In the expression vector, fluorescent timer protein-encoding polynucleotide, e.g., as set forth in SEQ ID NO: 03, is linked to a regulatory sequence as appropriate to obtain the desired expression properties. These can include promoters (attached either at the 5' end of the sense strand or at the 3' end of the antisense strand), enhancers, terminators, operators, repressors, and inducers.

The promoters can be regulated or constitutive, and in many instances are regulated (e.g., conditionally active). In some situations it may be desirable to use conditionally active promoters, including, but not limited to, tissue-specific promoters; cell type specific promoters; developmental stage-specific promoters; promoters controlled by the cell cycle; promoters controlled by Circadian rhythm; and promoters whose activity is increased (e.g., activated) or decreased (e.g., suppressed) in response to an external or internal signal.

External and internal signals that affect promoter activity include, but are not limited to, infection of a cell by a microorganism, including, but not limited to, a bacterium (e.g., *Mycobacterium* spp., *Shigella*, *Chlamydia*, and the like), a protozoan (e.g., *Trypanosoma* spp., *Plasmodium* spp., *Toxoplasma* spp., and the like), a fungus, a yeast (e.g., *Candida* spp.), or a virus (including viruses that infect mammalian cells, such as human immunodeficiency virus, foot and mouth disease virus, Epstein-Barr virus, and the like; viruses that infect plant cells; etc.); change in pH of the medium in which a cell is maintained or a change in internal pH; excessive heat relative to the normal range for the cell or the multicellular organism; excessive cold relative to the normal range for the cell or the multicellular organism; an effector molecule such as a hormone, a cytokine, a chemokine, a neurotransmitter; an ingested or applied drug; a ligand for a cell-surface receptor; a ligand for a receptor that exists internally in a cell, e.g., a nuclear receptor; hypoxia; light; dark; mitogens, including, but not limited to, lipopolysaccharide (LPS), pokeweed mitogen; antigens; sleep pattern; electrical charge; ion concentration of the medium in which a cell is maintained or an internal ion concentration, exemplary ions including sodium ions, potassium ions, chloride ions, calcium ions, and the like; presence or absence of a nutrient; metal ions; a transcription factor; a tumor suppressor; cell-cell contact; and the like.

Cell-cycle controlled promoters include, but are not limited to, an E2F 1 promoter; a cyclin A promoter; a cyclin B promoter; a cyclin C promoter; a cyclin D promoter; a cyclin E promoter; and the like. Cell-cycle controlled promoters are known in the art, and any such promoter can be used. The nucleotide sequences of many such promoters are publicly available, including the following: (GenBank Accession Nos shown in parentheses): human cyclin A1 gene promoter (AF124143); human cyclin B1 gene promoter (U22364; S74452; U36838); mouse cyclin C promoter (U49050); mouse cyclin D1 promoter (AF212040; AF182716); rat cyclin D1 promoter (AF 148946); human cyclin D1 promoter (Z29078); human cyclin D2 promoter (U47284); human cyclin D3 promoter (U47285).

Exemplary tissue-specific or cell type-specific promoters include, but are not limited to, myosin heavy chain promoter for muscle specific expression, Madsen et al. (1998) Circ Res 82(8):908–917; lysosomal acid lipase promoter, Du et al. (1998) Gene 208(2):285–295; pancreatic expression using the amylase promoter, Dematteo et al. (1997) J Surg Res72(2):155–161; cardiac-specific overexpression, Kubota et al. (1997) Circ Res 81(4):627–635; folylpoly-gamma-glutamate synthetase promoter, Freemantle et al. (1997) J Biol Chem 272(40):25373–25379; tissue specific expression using neural restrictive silencer element, Kallunki et al. (1997) J Cell Biol 138(6):1343–1354, placenta specific expression using the HGH promoter, Nogues et al. (1997) Endocrinology 138(8):3222–3227, expression during pregnancy using the prolactin promoter, Schuler et al. (1997) Endocrinology 138(8):3187–3194, tissue specific expression using the alpha1(VI) collagen promoter, Braghetta et al. (1997) Eur J Biochem 247(1):200–208; B cell specific expression, Lennon et al. (1997) Immunogenetics 45(4): 266–273; endothelium specific expression, Ronicke et al. (1996) Circ Res 79(2):277–285, the keratin promoters (e.g., human keratin 14 promoter (Wang et al. 1997 Proc Natl Acad Sci US 94:219–26); bovine cytokeratin gene promoters, BKIII and BKVI (Alexander et al. 1995 Hum Mol Genet 4:993–9); keratin 10 gene promoter (Bailleul et al. 1990 Cell 62:697–708); and tyrosinase promoters (specific for melanocytes)). Epidermal-specific promoters are reviewed in Fuchs et al. 1994 (Princess Takamatsu Symp 24:290–302). Additional cell type-specific and/or tissue-specific promoters include promoters such as albumin (liver specific; Pinkert et al., 1987 Genes Dev. 1:268–277), lymphoid specific promoters (Calame et al., 1988 Adv. Immunol. 43:235–275); in particular promoters of T-cell receptors (Winoto et al., 1989 EMBO J. 8:729–733) and immunoglobulins; Banerji et al., 1983 Cell 33729–740; Queen and Baltimore, ibid. 741–748), neuron-specific promoters (e.g. the neurofilament promoter; Byrne et al., 1989 Proc. Natl. Acad. Sci. USA 86:5473–5477), pancreas-specific promoters (Edlunch et al., 1985 Science 230:912–916) and mammary gland-specific promoters (milk whey promoter, U.S. Pat. No. 4,873,316 and European Application Publication No. 264,166).

Developmentally regulated promoters include, but are not limited to, notch, numb, homeotic genes, murine homeobox promoters (Kessel et al., 1990 Science 249:374–379), and the like.

A promoter, and optionally additional regulatory element(s), is linked to the desired nucleotide sequence using the techniques described above for linkage to vectors. Any techniques known in the art can be used. In other words, the expression vector will provide a transcriptional and translational initiation region, which may be inducible or constitutive, where the coding region is operably linked under the transcriptional control of the transcriptional initiation region, and a transcriptional and translational termination region. These control regions may be native to the subject fluorescent timer protein gene, or may be derived from exogenous sources.

Expression vectors generally have convenient restriction sites located near the promoter sequence to provide for the insertion of nucleic acid sequences encoding heterologous proteins. A selectable marker operative in the expression host may be present. Expression vectors may be used for, among other things, the production of fusion proteins, as described above.

Expression cassettes may be prepared comprising a transcription initiation region, the gene or fragment thereof, and a transcriptional termination region. Of particular interest is the use of sequences that allow for the expression of functional epitopes or domains, usually at least about 8 amino acids in length, more usually at least about 15 amino acids in length, to about 25 amino acids, and up to the complete open reading frame of the gene. After introduction of the DNA, the cells containing the construct may be selected by means of a selectable marker, the cells expanded and then used for expression.

The above described expression systems may be employed with prokaryotes or eukaryotes in accordance with conventional ways, depending upon the purpose for expression. For large scale production of the protein, a unicellular organism, such as *E. coli, B. subtilis, S. cerevisiae*, insect cells in combination with baculovirus vectors, or cells of a higher organism such as vertebrates, e.g. COS 7 cells, HEK 293, CHO, *Xenopus oocytes*, etc., may be used as the expression host cells. In some situations, it is desirable to express the gene in eukaryotic cells, where the expressed protein will benefit from native folding and post-translational modifications. Small peptides can also be synthesized in the laboratory. Polypeptides that are subsets of the complete protein sequence may be used to identify and investigate parts of the protein important for function.

Specific expression systems of interest include bacterial, yeast, insect cell and mammalian cell derived expression systems. Representative systems from each of these categories is are provided below:

Bacteria. Expression systems in bacteria include those described in Chang et al., *Nature* (1978) 275:615; Goeddel et al., *Nature* (1979)281:544; Goeddel et al.,*Nucleic Acids Res*. (1980) 8:4057; EP 0 036,776; U.S. Pat. No. 4,551,433; DeBoer et al., *Proc. Natl. Acad. Sci*. (*USA*) (1983) 80:21–25; and Siebenlist et al., *Cell* (1980) 20:269.

Yeast. Expression systems in yeast include those described in Hinnen et al., *Proc. Natl. Acad. Sci*. (*USA*) (1978) 75:1929; Ito et al., *J. Bacteriol*. (1983) 153:163; Kurtz et al., *Mol Cell. Biol*. (1986) 6:142; Kunze et al., *J.*

Basic Microbiol. (1985) 25:141; Gleeson et al., *J. Gen. Microbiol*. (1986) 132:3459; Roggenkamp et al., *Mol. Gen. Genet*. (1986) 202:302; Das et al., *J. Bacterial*. (1984) 158:1165; De Louvencourt et al., *J. Bacteriol*. (1983) 154: 737; Van den Berg et al., *Bio/Technology* (1990) 8:135; Kunze et al., *J. Basic Microbiol*. (1985) 25:141; Cregg et al., *Mol. Cell. Biol*. (1985) 5:3376; U.S. Pat. Nos. 4,837,148 and 4,929,555; Beach and Nurse, *Nature* (1981) 300:706; Davidow et al., *Curr. Genet*. (1985) 10:380; Gaillardin et al., *Curr. Genet*. (1985) 10:49; Ballance et al., *Biochem. Biophys. Res. Commun*. (1983) 112:284–289; Tilburn et al., *Gene* (1983) 26:205–221; Yelton et al., *Proc. Natl Acad. Sci*. (*USA*) (1984) 81:1470–1474; Kelly and Hynes, *EMBO J*. (1985) 4:475479; EP 0 244,234; and WO 91/00357.

Insect Cells. Expression of heterologous genes in insects is accomplished as described in U.S. Pat. No. 4,745,051; Friesen et al., "The Regulation of Baculovirus Gene Expression", in: *The Molecular Biology Of Baculoviruses* (1986) (W. Doerfler, ed.); EP 0 127,839; EP 0 155,476; and Vlak et al., *J. Gen. Virol*. (1988) 69:765–776; Miller et al., *Ann. Rev. Microbiol*. (1988) 42:177; Carbonell et al., *Gene* (1988) 73:409; Maeda et al., *Nature* (1985) 315:592–594; Lebacq-Verheyden et al., *Mol. Cell. Biol*. (1988) 8:3129; Smith et al., *Proc. Natl. Acad. Sci*. (USA) (1985) 82:8844; Miyajima et al., *Gene* (1987) 58:273; and Martin et al., *DNA* (1988) 7:99. Numerous baculoviral strains and variants and corresponding permissive insect host cells from hosts are described in Luckow et al., *Bio/Technology* (1988) 6:47–55, Miller et al., *Generic Engineering* (1986) 8:277–279, and Maeda et al., *Nature* (1985) 315:592–594.

Mammalian Cells. Mammalian expression is accomplished as described in Dijkema et al., *EMBO J*. (1985) 4:761, Gorman et al., *Proc. Natl. Acad. Sci*. (*USA*) (1982) 79:6777, Boshart et al., *Cell* (1985) 41:521 and U.S. Pat. No. 4,399,216. Other features of mammalian expression are facilitated as described in Ham and Wallace, *Meth. Enz*. (1979) 58:44, Barnes and Sato, *Anal. Biochem*. (1980) 102:255, U.S. Pat. Nos. 4,767,704, 4,657,866, 4,927,762, 4,560,655, WO 90/103430, WO 87/00195, and U.S. Pat. No. RE 30,985.

Plant cells. Plant cell culture is amply described in various publications, including, e.g., *Plant Cell Culture: A Practical Approach* (1995) R. A. Dixon and R. A. Gonzales, eds., IRL Press; and U.S. Pat. No. 6,069,009. Vectors for use with plant cells are well known in the art and include plant viruses, plasmids such as Ti plasmids, and the like.

When any of the above host cells, or other appropriate host cells or organisms, are used to replicate and/or express the polynucleotides or nucleic acids of the invention, the resulting replicated nucleic acid, RNA, expressed protein or polypeptide, is within the scope of the invention as a product of the host cell or organism. The product is recovered by any appropriate means known in the art.

Once the gene corresponding to a selected polynucleotide is identified, its expression can be regulated in the cell to which the gene is native. For example, an endogenous gene of a cell can be regulated by an exogenous regulatory sequence inserted into the genome of the cell at location sufficient to at least enhance expressed of the gene in the cell. The regulatory sequence may be designed to integrate into the genome via homologous recombination, as disclosed in U.S. Pat. Nos. 5,641,670 and 5,733,761, the disclosures of which are herein incorporated by reference, or may be designed to integrate into the genome via non-homologous recombination, as described in WO 99/15650, the disclosure of which is herein incorporated by reference. As such, also encompassed in the subject invention is the production of the subject proteins without manipulation of the encoding nucleic acid itself, but instead through integration of a regulatory sequence into the genome of cell that already includes a gene encoding the desired protein, as described in the above incorporated patent documents.

Also provided are homologs of the subject genes. Homologues are identified by any of a number of methods. A fragment of the provided cDNA may be used as a hybridization probe against a cDNA library from the target organism of interest, where low stringency conditions are used. The probe may be a large fragment, or one or more short degenerate primers. Nucleic acids having sequence similarity are detected by hybridization under low stringency conditions, for example, at 50° C. and 6×SSC (0.9 M sodium chloride/0.09 M sodium citrate) and remain bound when subjected to washing at 55° C. in 1×SSC (0.15 M sodium chloride/0.015 M sodium citrate).

Nucleic acids having a region of substantial identity to the provided sequences, e.g. allelic variants, genetically altered versions of the gene, etc., bind to the provided sequences under stringent hybridization conditions. By using probes, particularly labeled probes of DNA sequences, one can isolate homologous or related genes.

Also provided are nucleic acids that hybridize to the above-described nucleic acids (e.g., SEQ ID NO:03) under stringent conditions. An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C. Stringent hybridization conditions are hybridization conditions that are at least as stringent as the above representative conditions. Other stringent hybridization conditions are known in the art and may also be employed to identify nucleic acids of this particular embodiment of the invention.

Also of interest are promoter elements of the subject fluorescent timer protein genes, where the sequence of the 5' flanking region may be utilized for promoter elements, including enhancer binding sites, e.g., that provide for regulation of expression in cells/tissues where the subject proteins gene are expressed.

Also provided are small DNA fragments of the subject nucleic acids, which fragments are useful as primers for PCR, hybridization screening probes, etc. Larger DNA fragments, i.e., greater than 100 nt are useful for production of the encoded polypeptide, as described in the previous section. For use in geometric amplification reactions, such as geometric PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The DNA may also be used to identify expression of the gene in a biological specimen. The manner in which one probes cells for the presence of particular nucleotide sequences, as genomic DNA or RNA, is well established in the literature. Briefly, DNA or mRNA is isolated from a cell sample. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to the subject sequence is indicative of fluorescent timer protein gene expression in the sample.

The sequence of a fluorescent timer protein gene, including flanking promoter regions and coding regions, may be mutated in various ways known in the art to generate targeted changes in promoter strength, sequence of the encoded protein, properties of the encoded protein, including fluorescent properties of the encoded protein, etc. The DNA sequence or protein product of such a mutation will usually be substantially similar to the sequences provided herein, e.g., will differ by at least one nucleotide or amino acid, respectively, and may differ by at least two but not more than about ten nucleotides or amino acids. The sequence changes may be substitutions, insertions, deletions, or a combination thereof. Deletions may further include larger changes, such as deletions of a domain or exon, e.g. of stretches of 10, 20, 50, 75, 100, 150 or more aa residues. Techniques for in vitro mutagenesis of cloned genes are known. Examples of protocols for site specific mutagenesis may be found in Gustin et al. (1993), *Biotechniques* 14:22; Barany (1985), *Gene* 37:111–23; Colicelli et al. (1985), *Mol. Gen. Genet.* 199:537–9; and Prentki et al. (1984), *Gene* 29:303–13. Methods for site specific mutagenesis can be found in Sambrook et al., *Molecular Cloning: A Laboratory Manual*, CSH Press 1989, pp. 15.3–15.108; Weiner et al. (1993), *Gene* 126:35–41; Sayers et al. (1992), *Biotechniques* 13:592–6; Jones and Winistorfer (1992), *Biotechniques* 12:528–30; Barton et al. (1990), *Nucleic Acids Res* 18:7349–55; Marotti and Tomich (1989), *Gene Anal. Tech.* 6:67–70; and Zhu (1989), *Anal Biochem* 177:120–4. Such mutated genes may be used to study structure-function relationships of a fluorescent timer protein, or to alter properties of the protein that affect its function or regulation.

In addition, the present invention is directed to an isolated nucleic acid molecule selected from the group consisting of: (a) isolated DNA or RNA from an organism from the phylum Cnidaria which encodes a fluorescent protein; (b) isolated DNA or RNA which hybridizes to isolated DNA or RNA of (a) and which encodes a fluorescent protein, e.g., under stringent conditions, as described supra; and (c) isolated DNA or RNA differing from the isolated DNAs or RNAs of (a) and (b) in codon sequence due to the degeneracy of the genetic code, and which encodes a fluorescent protein. In certain embodiments, the DNA or RNA is E5 or mutant thereof.

In another specific embodiment of the present invention, there is provided a vector capable of expressing the nucleic acid molecule of the present invention in a recombinant cell comprising the nucleic acid molecule and regulatory elements necessary for expression of the nucleic acid molecule in the cell. Specifically, the nucleic acid molecule encodes a fluorescent timer protein.

In still another specific embodiment of the present invention, there is provided a host cell into which a vector of the present invention has been introduced, which host cell expresses a fluorescent timer protein of the present invention. Host cells include isolated host cells (e.g., in vitro cell culture); host cells that are part of a tissue, both in vitro and in vivo; host cells that are part of an organ, both in vitro (e.g., in vitro organ culture) and in vivo; and host cells in a multicellular organism. A subject vector is introduced into a host cell in vitro, ex vivo, or in vivo. Cell transfected with a vector of the present invention include, but are not limited to, bacterial cells; yeast cells; fungal cells; animal cells, including, but not limited to, frog cells (e.g., *Xenopus laevis*), fish cells (e.g., Zebrafish), *Caenorhabditis elegans*, insect cells, and mammalian cells; and plant cells (e.g., *Arabidopsis*), including monocotyledons and dicotyledons. A representative example of a mammalian cell is an HEK 293 cell and an example of a bacterial cell is an *E. coli* cell.

Antibody Compositions

Also provided are antibodies to the subject fluorescent timer proteins. Suitable antibodies are obtained by immunizing a host animal with peptides comprising all or a portion of the subject protein. Suitable host animals include mouse, rat sheep, goat, hamster, rabbit, etc. The origin of the protein immunogen will generally be an Anthozoa species. The host animal will generally be a different species than the immunogen, e.g., nice, etc.

The immunogen may comprise the complete protein, or fragments and derivatives thereof Preferred immunogens comprise all or a part of the protein, where these residues contain the post-translation modifications found on the native target protein. Immunogens are produced in a variety of ways known in the art, e.g., expression of cloned genes using conventional recombinant methods, isolation from Anthozoa species, etc.

For preparation of polyclonal antibodies, the first step is immunization of the host animal with the target protein, where the target protein will preferably be in substantially pure form, comprising less than about 1% contaminant. The immunogen may comprise the complete target protein, fragments or derivatives thereof. To increase the immune response of the host animal, the target protein may be combined with an adjuvant, where suitable adjuvants include alum, dextran, sulfate, large polymeric anions, oil and water emulsions, e.g. Freund's adjuvant, Freund's complete adjuvant, and the like. The target protein may also be conjugated to synthetic carrier proteins or synthetic antigens. A variety of hosts may be immunized to produce the polyclonal antibodies. Such hosts include rabbits, guinea pigs, rodents, e.g. mice, rats, sheep, goats, and the like. The target protein is administered to the host, usually intradermally, with an initial dosage followed by one or more, usually at least two, additional booster dosages. Following immunization, the blood from the host will be collected, followed by separation of the serum from the blood cells. The Ig present in the resultant antiserum may be further fractionated using known methods, such as ammonium salt fractionation, DEAE chromatography, and the like.

Monoclonal antibodies are produced by conventional techniques. Generally, the spleen and/or lymph nodes of an immunized host animal provide a source of plasma cells. The plasma cells are immortalized by fusion with myeloma cells to produce hybridoma cells. Culture supernatant from individual hybridomas is screened using standard techniques to identify those producing antibodies with the desired specificity. Suitable animals for production of monoclonal antibodies to the human protein include mouse, rat, hamster, etc. To raise antibodies against the mouse protein, the animal will generally be a hamster, guinea pig, rabbit, etc. The antibody may be purified from the hybridoma cell supernatants or ascites fluid by conventional techniques, e.g. affinity chromatography using protein bound to an insoluble support, protein A SEPHAROSE™, etc.

The antibody may be produced as a single chain, instead of the normal multimeric structure. Single chain antibodies are described in Jost et al. (1994) *J Biol. Chem.* 269: 26267–73, and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

Also of interest in certain embodiments are humanized antibodies. Methods of humanizing antibodies are known in the art. The humanized antibody may be the product of an animal having transgenic human immunoglobulin constant region genes (see for example International Patent Applications WO 90/10077 and WO 90/04036). Alternatively, the antibody of interest may be engineered by recombinant DNA techniques to substitute the CH1, CH2, CH3, hinge domains, and/or the framework domain with the corresponding human sequence (see WO 92/02190).

The use of Ig cDNA for construction of chimeric immunoglobulin genes is known in the art (Liu et al (1987) *Proc. Natl. Acad. Sci. USA* 84:3439 and (1987) *J. Immunol.* 139:3521). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) *Sequences of Proteins of Immunological Interest*, N.I.H. publication no. 91–3242. Human C region genes are readily available from known clones. The choice of isotype will be guided by the desired effector functions, such as complement fixation, or activity in antibody-dependent cellular cytotoxicity. Preferred isotypes are IgG1, IgG3 and IgG4. Either of the human light chain constant regions, kappa or lambda, may be used. The chimeric, humanized antibody is then expressed by conventional methods.

Antibody fragments, such as Fv, F(ab')$_2$ and Fab may be prepared by cleavage of the intact protein, e.g. by protease or chemical cleavage. Alternatively, a truncated gene is designed. For example, a chimeric gene encoding a portion of the F(ab')$_2$ fragment would include DNA sequences encoding the CHI domain and hinge region of the H chain, followed by a translational stop codon to yield the truncated molecule.

Consensus sequences of H and L J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g. SV-40 early promoter, (Okayama et al. (1983) *Mol. Cell. Bio.* 3:280), Rous sarcoma virus LTR (Gorman et al. (1982) *P.N.A.S.* 79:6777), and moloney murine leukemia virus LTR (Grosschedl et al. (1985) *Cell* 41:885); native Ig promoters, etc.

Transgenics

The subject nucleic acid molecules can be used to generate transgenic, non-human plants or animals or site specific gene modifications in cell lines. Transgenic animals may be made through homologous recombination, where the endogenous locus is altered. Alternatively, a nucleic acid construct is randomly integrated into the genome. Vectors for stable integration include plasmids, retroviruses and other animal viruses, YACs, and the like.

Transgenic organisms of the subject invention include cells and multicellular organisms, e.g., plants and animals, that are endogenous knockouts in which expression of endogenous gene is at least reduced if not eliminated. Transgenic organisms of interest also include cells and multicellular organisms, e.g., plants and animals, in which the protein or variants thereof is expressed in cells or tissues where it is not normally expressed and/or at levels not normally present in such cells or tissues.

DNA constructs for homologous recombination will comprise at least a portion of the gene of the subject invention, wherein the gene has the desired genetic modification(s), and includes regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. (1990), *Meth. Enzymol.* 185:527–537.

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of leukemia inhibiting factor (LIF). When ES or embryonic cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting offspring screened for the construct. By providing for a different phenotype of the blastocyst and the genetically modified cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture. The transgenic animals may be any non-human mammal, such as laboratory animals, domestic animals, etc. The transgenic animals may be used in functional studies, drug screening, etc. Representative examples of the use of transgenic animals include those described infra.

Transgenic plants may be produced in a similar manner. Methods of preparing transgenic plant cells and plants are described in U.S. Pat. Nos. 5,767,367; 5,750,870; 5,739,409; 5,689,049; 5,689,045; 5,674,731; 5,656,466; 5,633,155; 5,629,470; 5,595,896; 5,576,198; 5,538,879; 5,484,956; the disclosures of which are herein incorporated by reference. Methods of producing transgenic plants are also reviewed in Plant Biochemistry and Molecular Biology (eds Lea & Leegood, John Wiley & Sons)(1993) pp 275–295. In brief, a suitable plant cell or tissue is harvested, depending on the nature of the plant species. As such, in certain instances, protoplasts will be isolated, where such protoplasts may be isolated from a variety of different plant tissues, e.g. leaf, hypoctyl, root, etc. For protoplast isolation, the harvested cells are incubated in the presence of cellulases in order to remove the cell wall, where the exact incubation conditions vary depending on the type of plant and/or tissue from which the cell is derived. The resultant protoplasts are then separated from the resultant cellular debris by sieving and centrifugation. Instead of using protoplasts, embryogenic explants comprising somatic cells may be used for preparation of the transgenic host. Following cell or tissue harvesting, exogenous DNA of interest is introduced into the plant cells, where a variety of different techniques are available for such introduction With isolated protoplasts, the opportunity arise for introduction via DNA-mediated gene transfer protocols, including: incubation of the protoplasts with naked DNA, e.g. plasmids, comprising the exogenous coding sequence of interest in the presence of polyvalent cations, e.g. PEG or PLO; and electroporation of the protoplasts in the presence of naked DNA comprising the exogenous sequence of interest. Protoplasts that have successfully taken up the exogenous DNA are then selected, grown into a callus, and ultimately into a transgenic plant through contact with the appropriate amounts and ratios of stimulatory factors, e.g. auxins and cytokinins. With embryogenic explants, a convenient method of introducing the exogenous DNA in the target somatic cells is through the use of particle acceleration or "gene-gun" protocols. The resultant explants are then allowed to grow into chimera plants, cross-bred and transgenic progeny are obtained. Instead of the naked DNA approaches described above, another convenient method of producing transgenic plants is Agrobacterium mediated transformation. With Agrobacterium mediated transformation, co-integrative or binary vectors comprising the exogenous DNA are prepared and then introduced into an appropriate Agrobacterium strain, e.g. A. tumefaciens. The resultant bacteria are then incubated with prepared protoplasts or tissue explants, e.g. leaf disks, and a callus is produced. The callus is then grown under selective conditions, selected and subjected to growth media to induce root and shoot growth to ultimately produce a transgenic plant.

Utility

The subject fluorescent timer proteins of the present invention (as well as other components of the subject invention described above) find use in a variety of different applications. Representative uses are described below, where the following described uses are merely representative and are in no way meant to limit the use of the subject proteins to those described below.

The subject proteins are particularly useful for monitoring the activity of a regulatory element, for monitoring protein trafficking, and for monitoring protein stability. Of particular interest is the use of a subject timer protein to investigate temporal aspects of the activity of a regulatory element, protein trafficking, and protein stability. In some embodiments, the methods are used in a multicellular organism. In these embodiments, the methods are useful for determining cell fate during development and organ remodeling, thus distinguishing between cell migration and cell expansion (e.g., proliferation) or differentiation. The methods are also useful for spatial and temporal visualization of newly synthesized proteins and accumulated proteins. For example, a construct is introduced into a fertilized egg, or into a cell during a very early stage of development, and the fate of the cell is monitored. The methods are further useful to visualize and distinguish newly synthesized proteins in various subcellular compartments. The methods are also useful in distinguishing between newly formed and preexisting structures, e.g., membrane junctions, and components of the extracellular matrix.

Monitoring Activity of a Gene Regulatory Element

The present invention provides methods of measuring the activity of a gene regulatory element in a cell. Fluorescent timer proteins are used to determine the activation/deactivation of gene expression, e.g., developmental gene expression; cell type-specific gene expression; tissue-specific expression; cell cycle dependent gene expression; circadian rhythm specific gene expression; differential gene expression caused by a mutation (e.g., in a tumor suppressor, a transcription factor, a cell-cycle control element) or de-regulation of a gene; and expression induced or suppressed, directly or indirectly, by an external or an internal signal.

External and internal signals that affect promoter activity include, but are not limited to, infection of a cell by a microorganism, including, but not limited to, a bacterium (e.g., Mycobacterium spp., Shigella, Chlamydia, and the like), a protozoan (e.g., Trypanosoma spp., Plasmodium spp., Toxoplasma spp., and the like), a fungus, a yeast (e.g., Candida spp.), or a virus (including viruses that infect mammalian cells, such as human immunodeficiency virus, foot and mouth disease virus, Epstein-Barr virus, and the like; viruses that infect plant cells; etc.); change in pH of the medium in which a cell is maintained or a change in internal pH; excessive heat relative to the normal range for the cell or the multicellular organism; excessive cold relative to the normal range for the cell or the multicellular organism; an effector molecule such as a hormone, a cytokine, a chemokine, a neurotransmitter; an ingested or applied drug; a ligand for a cell-surface receptor; a ligand for a receptor that exists internally in a cell, e.g., a nuclear receptor; hypoxia; light; dark; sleep patterns; electrical charge; ion concentration of the medium in which a cell is maintained or an internal ion concentration, exemplary ions including sodium ions, potassium ions, chloride ions, calcium ions, and the like; presence or absence of a nutrient; metal ions; a transcription factor; mitogens, including, but not limited to, lipopolysaccharide (LPS), pokeweed mitogen; antigens; a tumor suppressor; cell-cell contact; and the like.

In some embodiments, the methods involve introducing into a cell a construct that includes a promoter (and optionally additional regulatory elements) operably linked to a nucleic acid molecule that encodes a fluorescent timer protein, and detecting fluorescence in the cell. In other embodiments, the methods involve introducing into a cell a construct that includes a nucleic acid molecule that encodes a fluorescent timer protein, where the nucleic acid molecule is not operably linked to a promoter, and detecting fluorescence in the cell.

After being synthesized in the cell, the fluorescent timer protein initially fluoresces at a first wavelength, and, over time, fluoresces at at least a second wavelength. The time that elapses between emission at the first wavelength and emission at the second wavelength (and subsequent wavelengths) is characteristic of the age (e.g., time after synthesis) of a given fluorescent timer protein, and may be employed to determine the age of a given fluorescent protein.

In some embodiments, the change in the ratio of fluorescence intensity at the first wavelength to fluorescence intensity at the second wavelength ("the ratio") is linear over time. Where the ratio versus time relationship is linear, the ratio at any given time can be used to calculate the amount of time elapsed from synthesis of the protein. Therefore, the activity of a promoter can be monitored by detecting the fluorescence at the first and second wavelengths, and relating the ratio to the amount of time elapsed since synthesis of the protein.

Determination of the time elapsed from synthesis of the protein is qualitative or quantitative. For example, where the fluorescent timer protein undergoes a spectral shift from green to red over time, the protein can be visualized, e.g., by fluorescence microscopy, and the age of the protein estimated. Alternatively, where the ratio of fluorescence intensity is linear over time, the amount of time elapsed since synthesis of the protein can be calculated as described above.

In many embodiments, the time elapsed since synthesis of the protein is essentially the same as the time elapsed since activation of the regulatory element. Thus, the methods provide for determination of the amount of time elapsed since activation of a promoter. In other embodiments, a lag time exists between synthesis of the protein and emission at a first wavelength. As discussed above, the timer protein is calibrated, and thus the lag time from synthesis to emission at a first wavelength is known. In these embodiments, the amount of time elapsed between activation of a promoter is determined by visualizing the fluorescence or by measuring fluorescence intensity at a first and a second wavelength, and subtracting the lag time from the estimated or calculated amount of time elapsed from synthesis.

In other embodiments, the methods provide for determination of the amount of time elapsed since shut down (e.g., transcriptional inactivation) of a promoter. Detecting emission at a second wavelength is used to determine when a promoter is inactivated in response to an external signal, when a promoter is inactivated during the normal course of development, etc. A construct including a regulatory element, e.g., a promoter, operably linked to a nucleic acid molecule encoding a subject timer protein is introduced into a cell of a multicellular organism. The timer protein is produced in the cell when the promoter is active, and this timer protein emits at a first wavelength. Once the promoter is inactivated, the timer protein is no longer produced. The population of timer protein produced during the time period when the promoter was active begins to "age," i.e., members of the population begin to undergo a spectral shift and emit at a second wavelength that is distinguishable from the first wavelength. Thus, the amount of time elapsed since inactivation of the promoter can be determined by determining the ratio of fluorescence intensity at the second wavelength to the fluorescence intensity at the first wavelength. Alternatively, the amount of time elapsed can be estimated by observing the fluorescence in the cell.

In some embodiments, the promoter is active and is subsequently inactivated in the same cell. In other embodiments, the promoter is active in a first cell, and is subsequently inactivated in a progeny cell. In some of these embodiments, the first cell and the progeny cell are in the same multicellular organism.

In some embodiments, a construct is used that includes, in order from 5' to 3' and in operable linkage, a regulatory element and a nucleic acid molecule that has a sequence encoding a fluorescent timer protein. The construct is introduced into a cell, and, after a period of time, fluorescence at a first and a second wavelength is detected.

Regulatory elements include promoters, enhancers, polyadenylation signals, terminators, protein degradation signals, and the like. Promoters of interest include, but are not limited to, cell cycle-regulated promoters; inducible and regulated promoters (e.g., inducible or regulated by internal or external signals); tissue-specific promoters; developmentally regulated promoters (e.g., promoters of homeotic genes); and the like.

A timer protein is useful to monitor temporal aspects of a cell-cycle-dependent promoter. A construct including a cell cycle-dependent promoter operably linked to a timer protein is introduced into a cell, and the spectral shift of the fluorescent timer protein monitored. In these embodiments, it is frequently of interest to include a cell cycle dependent degradation signal in the construct. For example, a timer protein is fused in frame to a cyclin degradation box. The choice of cell cycle-dependent degradation signal will depend on various factors, including the particular cell cycle-regulated promoter chosen. For example, if the promoter is one that is active ("turned on") early in the cell cycle, the cell cycle-dependent degradation signal is one that leads to degradation of the timer protein late in the cell cycle.

In other embodiments, a construct is used that includes a nucleic acid molecule having a sequence encoding a fluorescent timer protein, where the nucleic acid molecule is not operably linked to a promoter. The construct is introduced into a cell, and, after a period of time, fluorescence at a first and a second wavelength is detected. When the construct integrates into the genome of the cell such that the fluorescent timer protein-encoding nucleic acid molecule integrates at or near an endogenous promoter that is transcriptionally active, or that becomes transcriptionally active, the timer protein will be produced, and fluorescence can be detected. Such constructs are useful for detecting activity of an endogenous promoter in a cell, and are therefore useful to identify a regulatory element that is temporally regulated in a cell.

The construct is introduced into a cell, e.g., an isolated cell (e.g., a cell in in vitro culture); a cell in a multicellular organism; a cell in a tissue; or a cell in an organ. Cells include eukaryotic cells and prokaryotic cells. The construct is introduced into the cell using any known method, including, but not limited to, transformation, transfection, electroporation, calcium phosphate precipitation, microinjection, infection, and the like.

Fluorescence is detected in the cell into which the construct is introduced, and/or in the progeny of such a cell. Detecting fluorescence in progeny cells is useful for monitoring developmental regulation of a gene, e.g., where a given regulatory element is active in a particular cell, but not in its progeny, or vice versa. Thus, in some embodiments, the invention provides methods for determining the activity of a promoter in the progeny of a cell into which a construct that encodes a fluorescent timer protein operably linked to a regulatory element(s). Where a regulatory element is active in a first cell, the first cell will contain a population of timer proteins that emit at a first wavelength. Where the regulatory element is inactive in a second, progeny cell, the progeny cell will contain a population of timer proteins that emit at a second wavelength.

Drug Screening Applications

A cell containing a construct that includes a regulatory element operably linked to a fluorescent timer protein is useful in drug screening applications to identify agents that modulate the activity of a regulatory element. Accordingly, the invention provides methods of identifying an agent that modulates the activity of a regulatory element. The methods generally involve contacting a cell harboring a construct that includes a regulatory element operably linked to a nucleic acid molecule encoding a subject fluorescent timer protein with an agent being tested; and determining the effect, if any, of the agent on the activity of the regulatory element. In some embodiments, the construct is stably introduced into the cell (e.g., the construct integrates into the genome of the cell or is stably maintained as an extrachromosomal element). In other embodiments, the construct is transiently maintained in the cell. Cells useful in such assays include animal, plant, and bacterial cells, including, but not limited to, mammalian cell lines (e.g., 293 cells, COS cells, and the like); insect cell lines (e.g., *Drosophila* S2 cells, and the like); and plant cell lines.

A variety of different candidate agents ("test agents") may be screened by the screening methods of the invention. Candidate agents encompass numerous chemical classes, though typically they are organic molecules, and may be small organic compounds having a molecular weight of more than 50 and less than about 2,500 daltons. Candidate agents comprise functional groups necessary for structural interaction with proteins, e.g., hydrogen bonding, and can include at least an amine, carbonyl, hydroxyl or carboxyl group, or at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents, also referred to herein as "test agents," are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

An "agent that modulates the activity of a regulatory element", as used herein, describes any molecule, e.g. synthetic or natural organic or inorganic compound, protein or pharmaceutical, with the capability of altering the activity of a regulatory element, as described herein. Generally a plurality of assay mixtures is run in parallel with different agent concentrations to obtain a differential response to the various concentrations. Typically, one of these concentrations serves as a negative control, i.e. at zero concentration or below the level of detection. The activity of the regulatory element is determined by measuring the fluorescence intensity at a first wavelength and at a second wavelength, as described above.

An agent of interest that modulates the activity of a regulatory element increases or decreases the activity by at least about 10%, at least about 15%, at least about 20%, at least about 25%, more preferably at least about 50%, more preferably at least about 100%, or 2-fold, more preferably at least about 5-fold, more preferably at least about 10-fold or more when compared to a suitable control.

As noted above, the methods generally involve contacting a cell harboring a construct that includes a regulatory element operably linked to a subject fluorescent timer protein with a test agent. In some embodiments, a known inducer or suppressor of the activity of the regulatory element (e.g., an external signal, as described above) is also included in the assay. The above components of the method may be combined at substantially the same time or at different times. Incubations are performed at any suitable temperature, typically between 4° and 40° C. Incubation periods are selected for optimum activity, but may also be optimized to facilitate rapid high-throughput screening. Typically between 0.1 and 1 hours will be sufficient.

In some embodiments, a test agent reduces the activity of the regulatory element. Such agents are useful to downregulate a regulatory element, e.g., to decrease the production of a protein that is normally produced when the regulatory element is active.

As one non-limiting example, the invention provides screening methods to identify agents that reduce the activity of a cell cycle regulated promoter. Agents that reduce the activity of a cell cycle regulated promoter are candidate anti-cancer agents.

In other embodiments, a test agent increases the activity of the regulatory element. In some of these embodiments, the test agent increases the activity of the regulatory element in the presence of a suppressor of the regulatory element.

Flow Cytometry Applications

The invention provides methods of isolating a cell from a population of cells, and methods of enriching a population of cells for a particular sub-population of cells, the isolated cell or enriched cell population containing an active regulatory element operably linked to a subject fluorescent timer protein such that the fluorescent timer protein is produced in the cell. The methods generally involve introducing into a starting cell population a construct containing a regulatory element operably linked to a nucleic acid molecule encoding a subject fluorescent timer protein, and sorting a population of cells that contains subject timer protein emitting at a first wavelength. One or more rounds of cell sorting are performed to obtain an enriched population. In some embodiments, one or more additional rounds of cell sorting are performed to sort for cells containing fluorescent timer protein that emits at a second wavelength.

The term "enriched" as used herein to describe a cell population that has been sorted from a starting cell population refers to a cell population that contains at least about 50%, at least about 60%, at least about 70%, at least about 75%, at least about 80%, at least about 85%, at least about 90%, or at least about 95% or more, exhibiting the characteristic that is the basis for the cell sorting protocol. For example, if the characteristic is fluorescence between 490 and 510 nm, then an enriched population contains at least about 50%, at least about 60%, at least about 70%, at least about 75%, at least about 80%, at least about 85%, at least about 90%, or at least about 95% or more, cells that exhibit fluorescence between 490 and 510 nm.

The methods are useful for enriching a cell population in which the regulatory element operably linked to the timer protein-encoding nucleic acid molecule is active. In some embodiments, the regulatory element is one that is activated in response to an external or internal signal. In these embodiments, the methods further include the step of contacting the starting population with an agent that activates the regulatory element in the introduced construct, or subjecting the starting cell population to an internal or external signal that activates the regulatory element. For example, a staring population is a population of hematopoietic stem cells, and the introduced construct contains a promoter that is expressed transiently in a progenitor cell. The starting population is grown in vitro under culture conditions that favor differentiation of at least a portion of the stem cells into the progenitor cells. This population is subjected to cell sorting on the basis of emission at a first wavelength. The enriched population is then cultured in vitro under conditions that favor differentiation into a particular lineage, e.g., T cells, B cells, macrophages, monocytes, and the like. Progeny cells are sorted on the basis of emission at a second wavelength, to yield a second population that are enriched for cells that are differentiated.

The methods are also applicable to sorting multicellular organisms. In these embodiments, a population enriched for multicellular organisms, in which the regulatory element operably linked to the timer protein-encoding nucleic acid molecule is active in one or more cells of the multicellular organisms, is obtained. Non-limiting examples of multicellular organisms include embryos of non-human transgenic animals, plants grown in in vitro culture, and the like.

The methods are useful to enrich for a population of cells that are synchronized, e.g., that are in the same phase of the cell cycle at substantially the same time. For example, a construct having a cell cycle regulated promoter operably linked to a subject fluorescent timer protein is introduced into a starting population of cells. When a cell(s) of the starting population enters the phase of the cell cycle at which the cell cycle regulated promoter is active, the subject fluorescent timer protein is produced in the cell. The starting cell population is subjected to a first round of cell sorting, such that cells containing timer protein emitting at a first wavelength are sorted, to obtain an enriched population. A further round of cell sorting can be performed to sort for cells in the enriched population that are in a subsequent phase of the cell cycle at which the cell cycle regulated promoter is inactive. This entails subjecting the enriched population to a second round of cell sorting, such that cells containing timer protein emitting at a second wavelength are sorted. Further rounds of cell sorting can be performed, as desired or as required for a particular purpose.

Protein Trafficking

Fluorescent timer proteins find use in applications for monitoring movement of a protein, and for monitoring protein turnover. Protein movement is monitored within a living cell (e.g., between organelles, between subcellular compartments, between regions of a cell (e.g., along an axon of a neuronal cell), or within a cell membrane), i.e., intracellular movement; between two or more cells, i.e., intercellular movement; or from a living cell to an extracellular fluid (e.g., interstitial fluid, serum, cerebrospinal fluid, or other bodily fluid). Protein movement is monitored within a living tissue; during the course of development of a multicellular organism; in response to an external effect; in response to an ingested or applied agent; in response to an internal signal (e.g., a hormone, etc.); and the like. External and internal signals include those described above.

The methods generally involve exposing a fluorescent timer protein in a cell to an excitation wavelength, and detecting fluorescence. Where the ratio of fluorescence at the first wavelength to fluorescence at the second wavelength is linear over time, the ratio at any given time after exposure to the excitation wavelength is determined, and the time elapsed from synthesis calculated. Thus, the amount of time that it takes for a protein to move from one region in a cell to another, from one cell to another, or from a cell to another location in a multicellular organism, can be determined.

In these methods, a construct that has a nucleotide sequence encoding a fusion protein is used. The fusion protein includes a protein that is being studied, and a fluorescent timer protein, fused in-frame at the amino- or carboxyl-terminus of the protein being studied.

A subject fluorescent timer protein is useful to monitor temporal aspects of movement of a protein into a subcellular organelle. As one non-limiting example, a fusion protein that includes a subject fluorescent timer protein fused in-frame to a nuclear localization signal is produced in the cytoplasm of a cell. In response to an external signal, the fusion protein moves from the cytoplasm into the nucleus. The re-distribution of the fusion protein over time is monitored by detecting emission at a first and at a second wavelength over time. As an example, a timer protein is used that first shows green fluorescence, and, after a time, red fluorescence. Initially, green fluorescence is detected in the cytoplasm, and, after a time, the protein moves into the nucleus. Newly synthesized protein emits in the green spectrum, while "older" protein emits in the red spectrum. Protein that has moved into the nucleus is red, while protein in the cytoplasm is green.

Fluorescent timer proteins are useful in investigations in which photobleaching techniques are currently employed. Thus, a fluorescent timer protein can be used to label a protein to trace the movement of the protein within an intact cell, the nucleus, an organelle, or a cell membrane, from one cell to another, or from one location to another in a multicellular organism. Two prevalent photobleaching techniques are fluorescence recovery after photobleaching (FRAP) and fluorescence loss in photobleaching (FLIP). FRAP is used to estimate the turnover rates of molecules by the rate of influx of a bleached region by unbleached molecules from areas surrounding the bleached region. FRAP is described in numerous publications, including, e.g., Misteli et al. (2000) *Nature* 408:877–881; Snaar et al. (2000) *J. Cell. Biol.* 151:653–662; Dundr et al. (2000) *J. Cell Biol.* 150:433–446; Estes et al. (2000) *J. Neurogenet.* 13;233–255; and Vos et al. (2000) *Curr. Biol.* 10:1–7. FLIP is based on monitoring the loss of fluorescence outside a repeatedly bleached region. FLIP studies show continuity of transport between different populations of fluorophores. FLIP has been described in the literature, including, e.g., in White and Stelzer (1999) *Trends Cell Biol.* 9:61–65, and references cited therein.

In some embodiments, the methods comprise exposing a defined region of a cell containing a fluorescent timer protein to an excitation wavelength of light and detecting fluorescence. Defined regions of a cell include, but are not limited to, a mitochondria, a nucleus, a Golgi apparatus, an endoplasmic reticulum, a rough endoplasmic reticulum, a lysosome, a secretory vesicle, a pseudopodium, a chloroplast, an axon of a neuronal cell, and the like.

In some applications, fluorescent timer proteins are used to track the movement of a protein in a cell or an organism, e.g., a transgenic cell or organism that synthesizes a protein tagged with a fluorescent timer protein, in response to exposure to a particular external or internal signal, as described above. Agents (e.g., ingested or applied drugs) include, e.g., an agent being tested for therapeutic efficacy; an agent being tested for negative effects on a cell or an organism. The movement of the protein in the cell or organism exposed to a particular condition or agent is compared to a suitable control, e.g., a non-transgenic cell or organism of the same type; or a transgenic cell or organism not exposed to the test agent.

As one non-limiting example, a construct that includes a promoter that drives transcription of a nucleic acid molecule encoding a fusion protein consisting of a subject fluorescent timer protein fused in-frame to a nuclear localization signal is introduced into a eukaryotic cell. Where the timer protein is E5, the fusion protein exhibits green fluorescence soon after it is synthesized. Initially, the fusion protein (and green fluorescence) is cytoplasmic. Over time, the protein enters the nucleus of the cell. Newly synthesized protein in the cytoplasm will fluoresce green. Protein that has moved into the nucleus will shift to red fluorescence. The appearance of red fluorescence in the nucleus is related to established timing of the spectral shift for E5.

The invention further provides methods of identifying agents that affect protein movement. The methods generally involve contacting a cell that harbors a construct that includes a regulatory element operably linked to a fusion protein that includes a protein whose movement is being monitored, and a subject fluorescent timer protein, with a test agent. Test agents are described above. In some embodiments, test agents are added to determine the effect, if any, on translocation of the fusion protein from a first region of a cell to at least a second region of the cell. In some embodiments, the promoter is an inducible promoter. In these embodiments, the test agent may be added simultaneously with the inducer, or shortly before or after (e.g., within an hour before or an hour after) adding the inducer. Assays are designed essentially as described above. Fluorescence is detected in a first region of the cell and in a second region of the cell. The rate of translocation of the fusion protein is determined either by visualizing fluorescence at a first and at least a second wavelength, or by measuring the ratio of fluorescence intensity over time. An agent of interest is one that affects translocation of the fusion protein, e.g., that reduces or increases the rate of translocation by at least about 10%, at least about 20%, at least about 30%, at least about 40%, at least about 50%, at least about 60%, at least about 70%, at least about 80%, at least about 90%, at least about 100%, or 2-fold, at least about 5-fold, or more, when compared to a suitable control. Suitable controls include a sample to which no test agent is added.

Protein Stability and Protein Turnover

In other embodiments, methods are provided for determining protein stability. The methods generally involve exposing a fluorescent timer protein to an excitation wavelength, and monitoring fluorescence of the protein over time. Where the ratio of fluorescence at the first wavelength to fluorescence at the second wavelength is linear over time, the ratio at any given time after exposure to the excitation wavelength is determined, and the time elapsed from synthesis calculated. In these methods, a construct that has a nucleotide sequence encoding a fusion protein is used. The fusion protein includes a protein that is being studied, and a fluorescent timer protein, fused in-frame at the amino- or carboxyl-terminus of the protein being studied.

Other Applications

Fluorescent timer proteins find use in a variety of different applications. One application of interest is the use of the fluorescent timer proteins as detectable labels which are capable of imparting fluorescence to a particular composition of matter. Of particular interest in certain embodiments are non-toxic fluorescent timer proteins. Fluorescent timer proteins may be incorporated into a variety of different compositions of matter, where representative compositions of matter include: food compositions, pharmaceuticals, cosmetics, living organisms, e.g., animals and plants, and the like. Where used as a detectable label, a sufficient amount of the fluorescent timer protein is incorporated into the composition of matter to impart the desired fluorescence thereto. The fluorescent timer protein may be incorporated into the composition of matter using any convenient protocol, where the particular protocol employed will necessarily depend, at least in part, on the nature of the composition of matter to be labeled. Protocols that may be employed include, but are not limited to: blending, diffusion, friction, spraying, injection, tattooing, and the like.

The fluorescent timer proteins may also find use as labels in analyte detection assays, e.g., assays for biological analytes of interest. For example, the fluorescent timer proteins may be incorporated into adducts with analyte specific antibodies or binding fragments thereof and subsequently employed in immunoassays for analytes of interest in a complex sample, as described in U.S. Pat. No. 4,302,536; the disclosure of which is herein incorporated by reference. Instead of antibodies or binding fragments thereof, fluorescent timer proteins or fluorescent fragments thereof may be conjugated to ligands that specifically bind to an analyte of interest, or other moieties, growth factors, hormones, and the like; as is readily apparent to those of skill in the art.

In yet other embodiments, the subject fluorescent timer proteins may be used as selectable markers in recombinant DNA applications, e.g., the production of transgenic cells and organisms, as described above. As such, one can engineer a particular transgenic production protocol to employ expression of the subject fluorescent timer proteins as a selectable marker, either for a successful or unsuccessful protocol. Thus, appearance of the color of the subject fluorescent timer proteins in the phenotype of the transgenic organism produced by a particular process can be used to indicate that the particular organism successfully harbors the transgene of interest, often integrated in a manner that provides for expression of the transgene in the organism. When used a selectable marker, a nucleic acid encoding a fluorescent timer protein can be employed in the transgenic generation process, where this process is described in greater detail supra. Particular transgenic organisms of interest where a fluorescent timer protein may be employed as a selectable marker include transgenic plants, animals, bacteria, fungi, and the like.

Fluorescent timer proteins find use in fluorescence resonance energy transfer (FRET) applications. In these applications, fluorescent timer proteins serve as donor and/or acceptors in combination with a second fluorescent protein or dye, e.g., a fluorescent protein as described in Matz et al., Nature Biotechnology (October 1999) 17:969–973, a green fluorescent protein from *Aequoria victoria* or fluorescent mutant thereof, e.g., as described in U.S. Pat. No. 6,066,476; 6,020,192; 5,985,577; 5,976,796; 5,968,750; 5,968,738; 5,958,713; 5,919,445; 5,874,304, the disclosures of which are herein incorporated by reference, other fluorescent dyes, e.g., coumarin and its derivatives, e.g. 7-amino-4-methyl-coumarin, aminocoumarin, bodipy dyes, such as Bodipy FL, cascade blue, fluorescein and its derivatives, e.g. fluorescein isothiocyanate, Oregon green, rhodamine dyes, e.g. texas red, tetramethylrhodamine, eosins and erythrosins, cyanine dyes, e.g. Cy3 and Cy5, macrocyclic chelates of lanthanide ions, e.g. quantum dye, etc., chemiluminescent dyes, e.g., luciferases, including those described in U.S. Pat. Nos. 5,843,746; 5,700,673; 5,674,713; 5,618,722; 5,418,155; 5,330,906; 5,229,285; 5,221,623; 5,182,202; the disclosures of which are herein incorporated by reference.

Specific examples of where FRET assays employing fluorescent timer proteins may be used include, but are not limited to: the detection of protein-protein interactions, e.g., mammalian two-hybrid system, transcription factor dimerization, membrane protein multimerization, multiprotein complex formation, etc., as a biosensor for a number of different events, where a peptide or protein covalently links a FRET fluorescent combination including the subject fluorescent proteins and the linking peptide or protein is, e.g., a protease specific substrate, e.g., for caspase mediated cleavage, a linker that undergoes conformational change upon receiving a signal which increases or decreases FRET, e.g., PKA regulatory domain (cAMP-sensor), phosphorylation, e.g., where there is a phosphorylation site in the linker or the linker has binding specificity to phosphorylated/dephosphorylated domain of another protein, or the linker has $Ca^{2+}$ binding domain. Representative fluorescence resonance energy transfer or FRET applications in which the subject proteins find use include, but are not limited to, those described in: U.S. Pat. Nos. 6,008,373; 5,998,146; 5,981, 200; 5,945,526; 5,945,283; 5,911,952; 5,869,255; 5,866, 336; 5,863,727; 5,728,528; 5,707,804; 5,688,648; 5,439, 797; the disclosures of which are herein incorporated by reference.

Another application in which fluorescent timer proteins find use is BRET (Bioluminescence Resonance Energy Transfer). BRET is a protein-protein interaction assay based on energy transfer from a bioluminescent donor to a fluorescent acceptor protein. The BRET signal is measured by the amount of light emitted by the acceptor to the amount of light emitted by the donor. The ratio of these two values increases as the two proteins are brought into proximity. The BRET assay has been amply described in the literature. See, e.g., U.S. Pat. Nos. 6,020,192; 5,968,750; and 5,874,304; and Xu et al. (1999) *Proc. Natl. Acad. Sci. USA* 96:151–156. BRET assays may be performed by genetically fusing a bioluminescent donor protein and a fluorescent acceptor protein independently to two different biological partners to make partner A-bioluminescent donor and partner B-fluorescent acceptor fusions. Changes in the interaction between the partner portions of the fusion proteins, modulated, e.g., by ligands or test compounds, can be monitored by a change in the ratio of light emitted by the bioluminescent and fluorescent portions of the fusion proteins. In this application, the subject proteins serve as donor and/or acceptor proteins. BRET assays can be used in many of the assays as FRET, which assays are noted above.

Fluorescent timer proteins also find use as biosensors in prokaryotic and eukaryotic cells, e.g. as $Ca^{2+}0$ ion indicator; as pH indicator, as phorphorylation indicator, as an indicator of other ions, e.g., magnesium, sodium, potassium chloride and halides. For example, for detection of Ca ion, proteins containing an EF-hand motif are known to translocate from the cytosol to membranes upon $Ca^{2+}0$ binding. These proteins contain a myristoyl group that is burried within the molecule by hydrophobic interactions with other regions of the protein. Binding of $Ca^{2+}$ induces a conformational change exposing the myristoyl group which then is available for the insertion into the lipid bilayer (called a "$Ca^{2+}$-myristoyl switch"). Fusion of such an EF-hand containing protein to Fluorescent Proteins (FP) could make it an indicator of intracellular $Ca^{2+}$ by monitoring the translocation from the cytosol to the plasma membrane by confocal microscopy. EF-hand proteins suitable for use in this system include, but are not limited to: recoverin (1–3), calcineurin B, troponin C, visinin, neurocalcin, calmodulin, parvalbumin, and the like. For pH, a system based on hisactophilins may be employed. Hisactophilins are myristoylated histidine-rich proteins known to exist in *Dictyostelium*. Their binding to actin and acidic lipids is sharply pH-dependent within the range of cytoplasmic pH variations. In living cells membrane binding seems to override the interaction of hisactophilins with actin filaments. At pH≦6.5 they locate to the plasma membrane and nucleus. In contrast, at pH 7.5 they evenly distribute throughout the cytoplasmic space. This change of distribution is reversible and is attributed to histidine clusters exposed in loops on the surface of the molecule. The reversion of intracellular distribution in the range of cytoplasmic pH variations is in accord with a pK of 6.5 of histidine residues. The cellular distribution is independent of myristoylation of the protein. By fusing FPs (Fluoresent Proteins) to hisactophilin the intracellular distribution of the fusion protein can be followed by laser scanning, confocal microscopy or standard fluorescence microscopy. Quantitative fluorescence analysis can be done by performing line scans through cells (laser scanning confocal microscopy) or other electronic data analysis (e.g., using metamorph software (Universal Imaging Corp) and averaging of data collected in a population of cells. Substantial pH-dependent redistribution of hisactophilin-FP from the cytosol to the plasma membrane occurs within 1–2 min and reaches a steady state level after 5–10 min. The reverse reaction takes place on a similar time scale. As such, hisactophilin-fluorescent protein fusion protein that acts in an analogous fashion can be used to monitor cytosolic pH changes in real time in live mammalian cells. Such methods have use in high throughput applications, e.g., in the measurement of pH changes as consequence of growth factor receptor activation (e.g. epithelial or platelet-derived growth factor) chemotactic stimulation/cell locomotion, in the detection of intracellular pH changes as second messenger, in the monitoring of intracellular pH in pH manipulating experiments, and the like. For detection of PKC activity, the reporter system exploits the fact that a molecule called MARCKS (myristoylated alanine-rich C kinase substrate) is a PKC substrate. It is anchored to the plasma membrane via myristoylation and a stretch of positively charged amino acids (ED-domain) that bind to the negatively charged plasma membrane via electrostatic interactions. Upon PKC activation the ED-domain becomes phosphorylated by PKC, thereby becoming negatively charged, and as a consequence of electrostatic repulsion MARCKS translocates from the plasma membrane to the cytoplasm (called the "myristoyl-electrostatic switch"). Fusion of the N-terminus of MARCKS ranging from the myristoylation motif to the ED-domain of MARCKS to fluorescent proteins of the present invention makes the above a detector system for PKC activity. When phosphorylated by PKC, the fusion protein translocates from the plasma membrane to the cytosol. This translocation is followed by standard fluorescence microscopy or confocal microscopy e.g. using the Cellomics technology or other High Content Screening systems (e.g. Universal Imaging Corp./Becton Dickinson). The above reporter system has application in High Content Screening, e.g., screening for PKC inhibitors, and as an indicator for PKC activity in many screening scenarios for potential reagents interfering with this signal transduction pathway. Methods of using fluorescent proteins as biosensors also include those described in U.S. Pat. Nos. 972,638; 5,824,485 and 5,650,135 (as well as the references cited therein) the disclosures of which are herein incorporated by reference.

Fluorescent timer proteins also find use in applications involving the automated screening of arrays of cells expressing fluorescent reporting groups by using microscopic imaging and electronic analysis. Screening can be used for drug discovery and in the field of functional genomics: e.g., where the subject proteins are used as markers of whole cells to detect changes in multicellular reorganization and migration, e.g., formation of multicellular tubules (blood vessel formation) by endothelial cells, migration of cells through Fluoroblok Insert System (Becton Dickinson Co.), wound healing, neurite outgrowth, etc.; where the proteins are used as markers fused to peptides (e.g., targeting sequences) and proteins that allow the detection of change of intracellular location as indicator for cellular activity, for example: signal transduction, such as kinase and transcription factor translocation upon stimuli, such as protein kinase C, protein kinase A, transcription factor NFkB, and NFAT; cell cycle proteins, such as cyclin A, cyclin B1 and cyclinE; protease cleavage with subsequent movement of cleaved substrate, phospholipids, with markers for intracellular structures such as endoplasmic reticulum, Golgi apparatus, mitochondria, peroxisomes, nucleus, nucleoli, plasma membrane, histones, endosomes, lysosomes, microtubules, actin) as tools for High Content Screening: co-localization of other fluorescent fusion proteins with these localization markers as indicators of movements of intracellular fluorescent fusion proteins/peptides or as marker alone; and the like. Examples of applications involving the automated screening of arrays of cells in which the subject fluorescent proteins find use include: U.S. Pat. No. 5,989,835; as well as WO/0017624; WO 00/26408; WO 00/17643; and WO 00/03246; the disclosures of which are herein incorporated by reference.

Fluorescent timer proteins also find use in high throughput screening assays. Fluorescent timer proteins are stable proteins with half-lives of more than 24 hours. Also provided are destabilized versions of the subject fluorescent proteins with shorter half-lives that can be used as transcription reporters for drug discovery. For example, a fluorescent timer protein can be fused with a putative proteolytic signal sequence derived from a protein with shorter half-life, e.g., PEST sequence from the mouse ornithine decarboxylase gene, mouse cyclin B1 destruction box and ubiquitin, etc. Promoters in signal transduction pathways can be detected using destabilized versions of the subject fluorescent proteins for drug screening, e.g., AP1, NFAT, NFkB, Smad, STAT, p53, E2F, Rb, myc, CRE, ER, GR and TRE, and the like.

Fluorescent timer proteins can be used as second messenger detectors, e.g., by fusing the subject proteins to specific domains: e.g., PKCgamma Ca binding domain, PKCgamma DAG binding domain, SH2 domain and SH3 domain, etc.

Secreted forms of fluorescent timer proteins can be prepared, e.g. by fusing secreted leading sequences to the subject proteins to construct secreted forms of fluorescent timer proteins, which in turn can be used in a variety of different applications.

Fluorescent timer proteins also find use in fluorescence activated cell sorting applications. In such applications, a fluorescent timer protein is used as a label to mark a population of cells and the resulting labeled population of cells is then sorted with a fluorescent activated cell sorting device, as is known in the art. FACS methods are described in U.S. Pat. Nos. 5,968,738 and 5,804,387; the disclosures of which are herein incorporated by reference.

Fluorescent timer proteins also find use as in vivo marker in animals (e.g., transgenic animals). For example, expression of a fluorescent timer protein can be driven by tissue specific promoters, where such methods find use in research for gene therapy, e.g., testing efficiency of transgenic expression, among other applications. A representative application of fluorescent timer proteins in transgenic animals that illustrates this class of applications of the subject proteins is found in WO 00/02997, the disclosure of which is herein incorporated by reference.

Additional applications of fluorescent timer proteins include: as markers following injection into cells or animals and in calibration for quantitative measurements (fluorescence and protein); as markers or reporters in oxygen biosensor devices for monitoring cell viability, as markers or labels for animals, pets, toys, food, etc.; and the like.

Fluorescent timer proteins also find use in protease cleavage assays. For example, cleavage inactivated fluorescence assays can be developed using fluorescent timer proteins, where fluorescent timer proteins are engineered to include a protease specific cleavage sequence without destroying the fluorescent character of the protein. Upon cleavage of the fluorescent timer protein by an activated protease fluorescence would sharply decrease due to the destruction of a functional chromophor. Alternatively, cleavage activated fluorescence can be developed using the subject proteins, where the fluorescent timer proteins are engineered to contain an additional spacer sequence in close proximity/or inside the chromophor. This variant would be significantly decreased in its fluorescent activity, because parts of the functional chromophor would be divided by the spacer. The spacer would be framed by two identical protease specific cleavage sites. Upon cleavage via the activated protease the spacer would be cut out and the two residual "subunits" of the fluorescent protein would be able to reassemble to generate a functional fluorescent protein. Both of the above types of application could be developed in assays for a variety of different types of proteases, e.g., caspases, etc.

Fluorescent timer proteins can also be used in assays to determine the phospholipid composition in biological membranes. For example, fusion proteins of fluorescent timer proteins (or any other kind of covalent or non-covalent modification of fluorescent timer proteins) that allows binding to specific phospholipids to localize/visualize patterns of phospholipid distribution in biological membranes also allowing colocalization of membrane proteins in specific phospholipid rafts can be accomplished with fluorescent timer proteins. For example, the PH domain of GRP1 has a high affinity to phosphatidyl-inositol tri-phosphate (PIP3) but not to PIP2. As such, a fusion protein between the PH domain of GRP1 and a fluorescent timer protein can be constructed to specifically label PIP3 rich areas in biological membranes.

The antibodies of the subject invention, described above, also find use in a number of applications, including the differentiation of fluorescent timer proteins from other fluorescent proteins.

Kits

Also provided by the subject invention are kits for use in practicing one or more of the above described applications, where the subject kits include a fluorescent timer protein or a means for making the protein, e.g., a construct comprising a vector that includes a coding region for a fluorescent timer protein. The protein or construct therefore is present in a suitable storage medium, e.g., buffered solution, typically in a suitable container. Also present in the subject kits may be antibodies to the provided protein. In certain embodiments, the kit comprises a plurality of different vectors each encoding the subject protein, where the vectors are designed for expression in different environments and/or under different conditions, e.g., constitutive expression where the vector includes a strong promoter for expression in mammalian cells, a promoterless vector with a multiple cloning site for custom insertion of a promoter and tailored expression, etc.

In some embodiments, a kit includes a construct ("recombinant vector") that includes a coding region encoding a timer protein. More than one restriction endonuclease site may be provided in a tandem and/or partially overlapping arrangement, such theft a "multiple cloning site" is provided. The recombinant vector may further comprise control sequences, such as a promoter, a translation initiation site, a polyadenylation site, and the like, for controlling expression of the timer coding region in prokaryotic or eukaryotic cells.

Thus, in some embodiments, the recombinant vector comprises, in order from 5' to 3', a transcription control sequence, a restriction endonuclease recognition site, and a nucleotide sequence encoding a timer protein. In other embodiments, the recombinant vector comprises, in order from 5' to 3', a transcription control sequence, a nucleotide sequence encoding a timer protein, and a restriction endonuclease recognition site. In some embodiments, restriction endonuclease recognition sequences are positioned both 5' and 3' of the coding region for the timer protein. The restriction endonuclease recognition site is typically within less than about 50 bases from the sequences encoding the timer protein. The recombinant vector typically further comprises a nucleotide sequence encoding a selectable marker (e.g., antibiotic resistance), and an origin of replication.

An example of a construct is presented in FIG. 19. In this plasmid, the E5 coding region is flanked on 5' and 3' sides by multiple cloning sites shown in the lower portion of FIG. 19. The E5 coding sequence expressed from the lac promoter ($P_{lac}$) in *E. coli*. A Kozak consensus sequence is located immediately 5' of E5 to enhance translation efficiency for expression in eukaryotic systems. The construct has a pUC backbone, which contains a high copy number origin of replication and an ampicillin resistance gene for propagation and selection in *E. coli*.

Another example of a construct is presented in FIG. 20. In this construct, the E5 coding region is flanked on the 5' side by a multiple cloning site (shown in the lower portion of FIG. 20) and a Kozak consensus sequence (Kozak (1987) *Nucl. Acids Res.* 15:8125–8148); and on the 3' side by an SV40 polyadenylation signal. The vector backbone contains an SV40 origin of replication for replication in mammalian cells expressing the SV40 T antigen, a pUC origin of replication for propagation in *E. coli*, and an f1 origin for single-stranded DNA production. A neomycin-resistance cassette ($Neo^r$) allows stably transfected eukaryotic cells to be selected using G418. This cassette consists of the SV40 early promoter, the neomycin/kanamycin resistance gene of Tn5, and polyadenylation signals from the herpes simplex virus thymidine kinase (HSV-TK) gene. A bacterial promoter 5' of the cassette expresses kanamycin resistance in *E. coli*. The regulatory elements and selectable markers in the recombinant constructs shown in FIGS. 19 and 20 are well known in the art.

The kit may further comprise appropriate restriction enzyme(s), ligases, and other reagents for inserting a heterologous nucleic acid molecule into the recombinant vector. The kit may further include oligonucleotide primers for use in amplifying (e.g., by a polymerase chain reaction) the timer coding sequences. The kit may further comprise bacteria; reagents for introducing the recombinant vector into the bacteria; reagents for selecting bacteria that comprise the recombinant vector; reagents for inducing expression of the timer protein.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

Example 1

Generating the E5 Mutant

A humanized version of the wild-type Anthozoa protein drFP583 was generated, since the preferred codon usage for humans results in better expression in mammalian cells. Humanized drFP583 was generated by changing wild type drFP583 nucleotide sequence to optimize the codons for expression of the fluorescent protein. The nucleotide sequence of the humanized drFP583 is shown in FIG. 1 and identified as SEQ ID No. 01.

Mutants of the humanized drFP583 were generated with an error-prone polymerase chain reaction, using a well-known protocol. Cadwell and Joyce (1992) *PCR Methods Appl.* 2:28. Random mutagenesis was performed with Diversity PCR Random Mutagenesis kit (Clontech) according to the manufacturer's protocol optimized for three to four mutations per 1000 base pairs. PCR products were cloned into the pQE-30/BamHI/HindIII vector. *Escherichia coli* DH5-α (Clontech) were transformed by electroporation in 10% glycerol with the ligation mixture, and were grown on Luria broth (LB)/agar/Ampicillin plates with 0.1 mM isopropyl-β-D-thiogalactopyranoside at 37° C. overnight. Colonies (up to 2000 to 5000 per plate) were screened visually, using a fluorescent microscope (Karl Zeiss) with a 31001 filter set (Chroma). For the study of fluorescence kinetics, bacteria harboring the recombinant plasmid were grown overnight on the LB plates at high density, scraped off, resuspended in ice-cold phosphate buffered saline (PBS), and sonicated. The lysate was cleared by centrifugation at 4° C., and the protein was purified from the supernatant on ice with a TALON resin (Clontech). All spectra were measured on purified proteins with a LS50B Luminescence Spectrometer (Perkin Elmer).

Mutations resulted in proteins with varying fluorescent properties. Of particular interest was the E5 mutant, which changes fluorescence over time. E5 contains two amino acid substitutions relative to humanized drFP583: V105A, and S197T. E5 changes its fluorescence from green to red over time both in vitro and in vivo, in *E. coli* and in mammalian cells (as described below). In addition, ES develops fluorescence faster than wild type drFP583 both in *E. coli* and mammalian cells.

Example 2

In vitro Characterization of the ES Mutant

Figure 4:
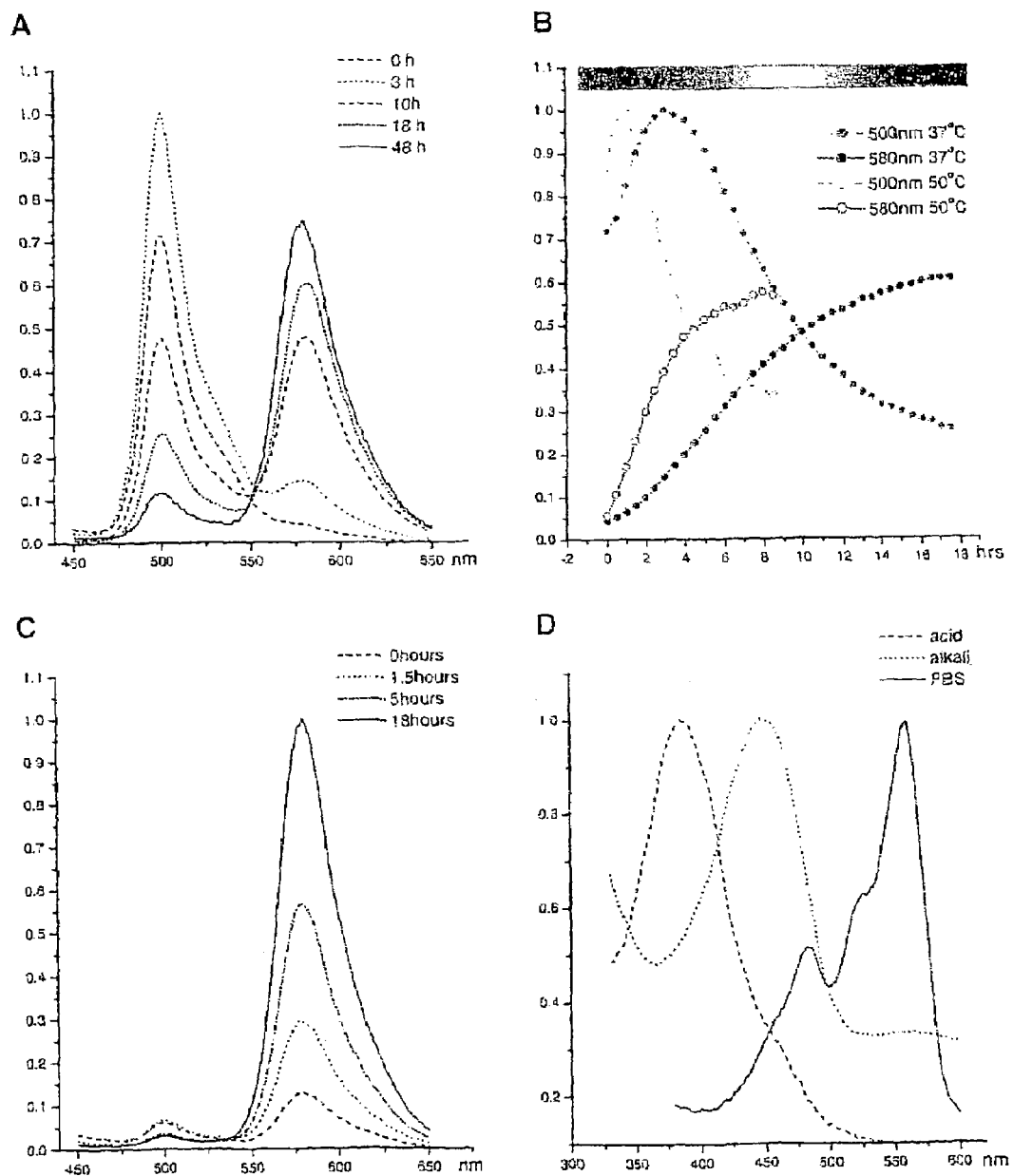

The E5 mutant undergoes a spectral shift over time. This mutant changes from initial bright green fluorescence to yellow, orange, and finally red over time, as shown in FIG. 4A. As shown in FIG. 4B, yellow and orange fluorescence indicate that protein species with green and red fluorophores are both present. Changing the temperature had the same effect on the rates of decay of green fluorescence and growth of red fluorescence, which suggests that these processes reflect the same chemical reaction (FIG. 4B). In addition, the overall reaction rate was independent of the initial concentration of ES protein in the range from 10 μg/ml to 1 mg/ml, as shown in FIG. 4B. The overall reaction rate was also insensitive to variations in ionic strength in the range from 10 mM to 1M NaCl, to the presence of 150 mM EDTA, or to changes in pH between 7.0 and 8.0. pH values below 4.5 or about 12 resulted in the disappearance of the red-shifted absorption and the appearance of 386-nm or 448-nm absorption peaks for acid and alkali, respectively, as shown in FIG. 1D.

As compared to drFP583, ES has two substitutions: $Val^{105}$ to $Ala^{105}$ (V105A) and $Ser^{197}$ to $Thr^{197}$ (S197T). The impact of each substitution on the fluorescent properties of ES was assessed in single mutants. Mutation of V105A resulted in a profound increase in brightness, compared to drFP583. The S197T mutant essentially recapitulated the fluorescent timer phenotype.

We modeled the structure of drFP583 on the basis of GFP crystal structure. Ormo et al. (1996) *Science* 273:1392. We found that $Ser^{197}$ in drFP583 is analogous to $Thr^{203}$ in GFP. $Thr^{203}$ is in direct contact with the fluorophore.

Example 3

In vivo Characterization of E5

Expression in HEK293 Cells

We characterized ES in a HEK293 mammalian cell line engineered with Tet-On or Tet-Off expression systems. The cDNA fragments coding for wild-type drFP583 and the E5 mutant were subcloned into the pTRE2 vector (Clontech). HEK293 Tet-On or 293 Tet-Off cells (Clontech) were transiently transfected with a CalPhos kit (Clontech). Doxycycline at a final concentration of 2 g/ml was added after 24 or 48 hours for Tet-On and Tet-Off cells, respectively. Cells were analyzed by FACS Calibur (Becton Dickinson). The images were taken with a XF35 Omega filter set, using a cooled charge-coupled device camera, and analyzed with MetaMorph Software (Universal Imaging).

Figure 5:
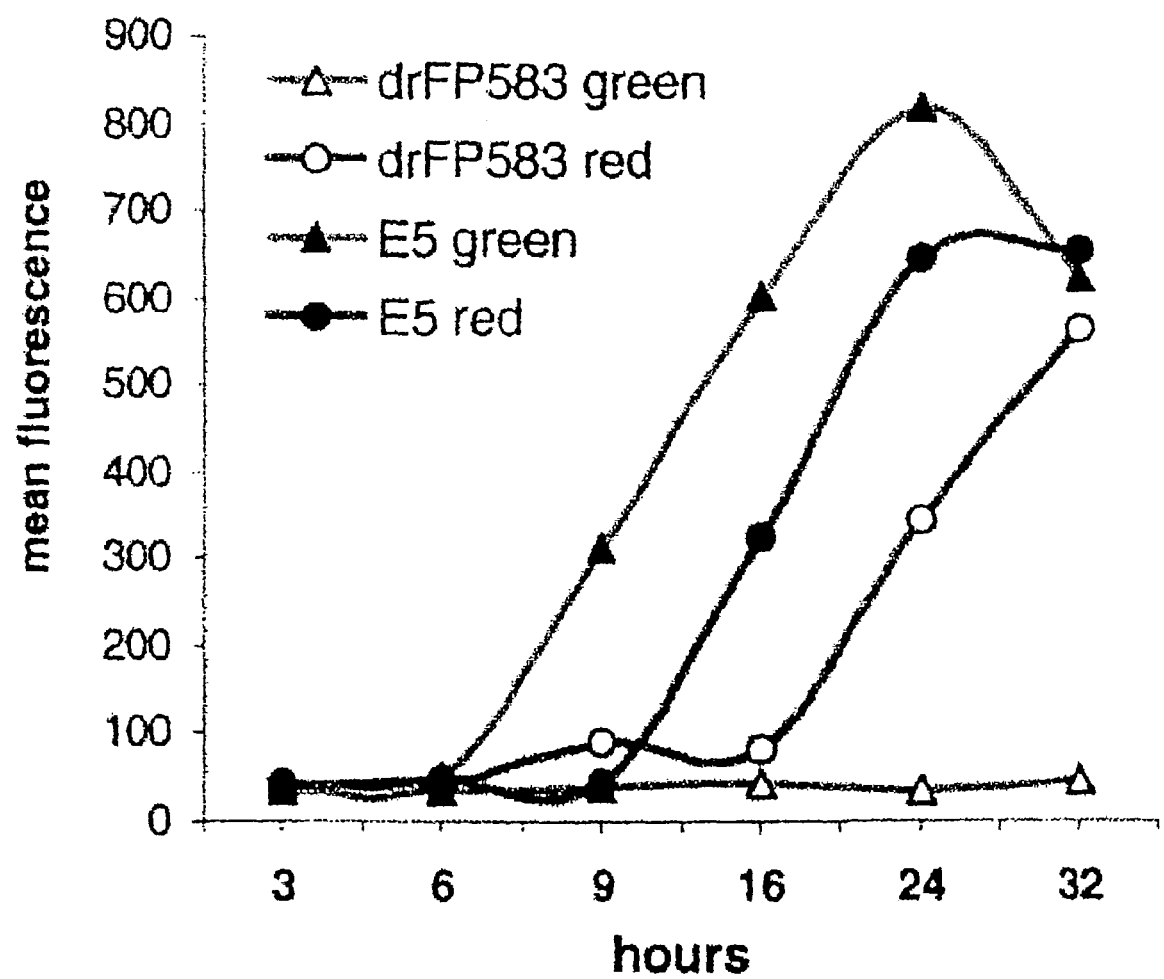
FIG. 5 is a graph depicting expression of E5 in HEK293 cells.

For 293 cells transfected with ES, a distinct green fluorescence was visible and was detected by flow cytometry between 6 and 9 hours after induction, as shown graphically in FIG. 5. Similar to bacterial expression, in mammalian cells, red fluorescence developed faster in the ES mutant than in wild-type drFP583 protein. When 293 Tet-Off cells were used, the majority of cells initially demonstrated strong green and red fluorescence at the beginning (a fully induced promoter) but lost the strong green fluorescence upon transcription shutdown, as shown in FIG. 6. These changes could be readily observed under a fluorescence microscope.

Expression in *C. elegans*

The E5 mutant was placed under the control of the *C. elegans* heat shock promoter hsp 16-41. The promoter exhibits minimal expression in unstressed animals, robust induction of transcription after heat shock, and rapid inactivation upon subsequent recovery to ambient temperature. Jones et al. (1989) *DNA* 8:481. An hsp-E5 transgene was microinjected into worms, and several independent lines carrying the transgene as an extrachromosomal array were established.

An E5 cDNA was subcloned into the pPD49.83 vector, which contains the hsp 16-41 promoter and a 3' UTR derived from the unc-54 gene. Germ line transformants were obtained by microinjection of a mixture of DNA containing the [hsp-E5(+)] transgene (100 μg/ml) and the unc-29 (+) gene (F35D3, 100 μg/ml into unc-29(e1072) mutant animals. Animals were heat-shocked by floating an agar plate containing the worms in a water bath preheated to 33° C. The images were taken with a Chroma Polychroich beamsplitter 86100bs filter set (for 4',6'-diamino-2-phenylindole, fluorescein isothiocyanate (FITC), and R-phycoeryhrin (PE)) and analyzed with MetaMorph Software (Universal Imaging).

The results are shown in FIG. 7. No fluorescence was observed in [hsp-E5(+)] worms maintained at room temperature. However, after a standard heat shock regime (1 hour at 33° C.), green fluorescence was observed in embryos as early as 2 hours into the recovery period. Red fluorescence was detected in [hsp-E5(+)] embryos at 5 hours after heat shock, and increased in intensity over time, so that at 50 hours after heat shock, the red:green signal ratio was close to 9:1. Similar kinetics of the fluorescent timer were observed in [hsp-E5(+)] worms at larval and adult stages. The prolonged periods of green fluorescence observed in these experiments are due to stabilization of the E5 mRNA, caused by the presence of a 3' untranslated region derived from the unc-54 gene. In our experiments, the color hue of transgenic embryos at different time points after heat shock could be readily distinguished by eye.

Moreover, within experimental error, the red:green fluorescence ratio changed linearly with time (at least within the first 14 hours), thus providing a unique measurement of time elapsed since heat shock. Remarkably, despite considerable heterogeneity in the absolute fluorescence intensities of individual embryos at any given time point, the red:green fluorescence ratios among embryos at the same time point were similar. In addition, the fluorescence ratio was uniform throughout the embryo, despite differences in cell types; indicating that, at least under our experimental conditions, the process of E5 maturation is independent of cellular environment.

We also showed that E5 displays very similar spectral properties both in vivo and in vitro, as shown in FIG. 8. FIG. 8 shows a comparison of the spectral shift that E5 undergoes in vivo in *C. elegans*, and in vitro.

Expression of E5 in *Xenopus*

We used the E5 mutant to trace the activity of the Oxt-2 promoter. The homeobox gene Oxt-2 is involved in the patterning of the anterior structures, which are common to all bilaterian animals. Galliot et al. (2000) *Trends Genet.* 16:1. In *Xenopus*, at the midgastrula stage, the major domain of Oxt-2 expression is in the head neuroectoderm. As development proceeds, the expression is almost completely suppressed in parts of this domain, namely, in the presumptive rostral area, telencephalon, and ventral diencephalon. Thus, in the tadpole's brain, Oxt-2 expression revealed by in situ hybridization is strong in the mesencephalon and dorsal diencephalon, but is much weaker in the telencephalon and ventral diencephalons, as shown in FIG. 9C.

We assembled a plasmid containing the E5 gene under the control of the *Xenopus* Oxt-2 promoter and microinjected this into both dorsal blastomers of the *X. laevis* embryo at the eight-cell stage. Plasmids containing the E5 mutant under the control of the Oxt-2 and Xanf-1 promoters were made as previously described. Matz et al. (1999) *Nature Biotechnol.* 17:969. The fluorescence of the E5 mutant in *Xenopus* was visualized by FITC filter set B1 of the Polyvar photomicroscope (Reihart-Jung).

The results are shown in FIGS. 9A–D. We observed a mosaic fluorescent image composed of clones of cells, which acquired the plasmid during blastomere cleavage. The telencephalon and rostral region of the tadpole are marked orange, indicating that the Oxt-2 promoter was once active there but is now mostly silent, giving the accumulated protein time to mature. Simultaneously, the mesencephalon and ventral diencephalons are green, indicating that Oxt-2 promoter activity is driving expression of E5 in these regions. In a control experiment, the expression of E5 was driven by the promoter of another homeobox gene, Xanf-1. The expression of Xanf-1 also occurs in neuroectoderm, but, unlike Oct-2, does not have distinct spatiotemporal domains and ceases before the tadpole stage. Correspondingly, the signal from the Xanf-1/ E5 construct appeared uniformly orange in the tadpole brain.

Example 4

Use of a Timer Protein to Analyze Cell Cycle-Regulated Promoters

FIG. 10 shows the strategy for using a fluorescent timer protein to study cell cycle-regulated promoters. The left panel of FIG. 10 schematically depicts the cell cycle. A construct that includes a cell cycle regulated promoter controlling transcription of a fluorescent timer protein is introduced into a cell, and fluorescence is monitored over time. Fluorescence is monitored using a fluorescence activated cell sorter. The right panel of FIG. 10 depicts schematically an expected distribution of fluorescence intensity at various times. Where the timer protein is E5, initially cells will emit green, then, over time, red. Use of a timer protein for cell cycle analysis is advantageous over previously available methods. See, e.g., Cheshier et al. (1999) *Proc. Natl. Acad. Sci. USA* 96:3120–3125. As shown in FIG. 11, previously available methods generally relied upon measuring incorporation of propidium iodide, which would be expected to increase during S (synthesis) phase; or upon measuring staining with a combination of pyronin Y (a stain for RNA) and Hoechst (a stain for DNA), which would be expected to increase during S phase.

A schematic representation of a construct including a cell cycle-regulated promoter, E2F 1, driving transcription of a timer protein is shown in FIG. 12. FIG. 12 also depicts schematically the points in the cell cycle during which various cyclins are active, and where they are degraded.

A plasmid was constructed that contains E5 coding sequences under transcriptional control of the mouse E2F1 promoter. The activity of the E2F1 promoter increases approximately 80-fold at the G1/S-phase boundary (as determined by the amount of transcription driven by the E2FI promoter), and is regulated by G0-specification repression via the E2F sites in the promoter. Hsiao et al. (1994) *Genes Dev.* 8:1526–1537. Constructs were made with the E2F1 promoter including sequences to $^+36$ relative to the E2F1 transcription start site ("E2F1+36-E5"); and with the E2F1 promoter including sequences to +98 relative to the E2F1 transcription start site ("E2F1+98-E5"). A further construct included the E5 coding region under transcriptional control of the CMV promoter ("CMV-E5").

The constructs were introduced into 293 cells, and the recombinant cells were analyzed by FACS. The results are shown in FIG. 13. FIG. 13 presents FACS plots showing phycoerythrin ("PhyEry") versus FITC ("Fluor"). The panel labeled "293 cells" shows results with mock-transfected 293 cells. The results shown in FIG. 13 demonstrate that the E2F1 promoter is functional in this system.

The E5 protein is a stable protein, and therefore the spectral shift did not occur until after the cells had already undergone a further mitotic event. To reduce the half-life of the E5 protein, plasmids were constructed that encode E5 fused in-frame to the ornithine decarboxylase (ODC) degradation signal. A first plasmid was constructed that encodes E5 fused in-frame to the ornithine decarboxylase (ODC) degradation signal, under transcriptional control of a cytomegalovirus promoter. FIG. 14 shows this construct schematically (right panel), and provides an expected distribution of fluorescence (left panel).

FIG. 15 shows the results of FACS analysis of CMV-driven synthesis of the E5-ODC fusion protein in 293 cells, in the presence or absence of cyclohexamide (CHX). Cells were analyzed 6 hours ("6h CHX") or 18 hours ("18 h CHX") after addition of CHX to inhibit protein synthesis.

When ODC is fused in-frame to E5, E5 is degraded, and red fluorescence accumulates. In contrast, in the absence of ODC, E5 is not degraded within the time frame of this analysis, and red fluorescence does not accumulate.

In another series of experiments, plasmids were constructed that contain a coding sequence for E5 fused in-frame to a cyclin B1 degradation signal, under transcriptional control of the E2F1 promoter. Cyclin B1 is degraded during late metaphase. FIG. 16 provides a schematic depiction of a construct, and provides a schematic depiction of the phases in the cell cycle.

Another construct includes E5NA coding sequences under transcriptional control of a murine stem cell virus (MSCV) promoter. Cherry et al. (2000) *Mol. Cell Biol.* 20:7419–7426. A control construct includes a fluorescent protein (DsRed2) that does not undergo a spectral shift over time. These constructs were introduced into 293 cells, and fluorescence measured by FACS. The results are shown in FIG. 17. The results show that E5NA behaves in a similar manner as E5 in a eukaryotic cell.

The experiments described above demonstrate the feasibility of using a timer protein in studies of cell cycle regulated promoters.

For cell cycle studies, it is of interest to develop mutants of E5 that exhibit red fluorescence sooner after green fluorescence than E5, i.e., mutants in which the period of time between green fluorescence and red fluorescence is less than for E5. FIG. 18 depicts the overall protein structure of E5. Superimposed on this structure are the amino acid substitutions V105A and S197T that distinguish E5 from the humanized version of drFP583 ("E"), as well as the amino acid substitutions I161T, N42H, Y120H, and V71M. Mutants of E5 are selected that exhibit red fluorescence at an earlier time after green fluorescence than E5. Mutants are generated by random mutagenesis. Alternatively, mutants are generated by site-directed mutagenesis to include, in addition to V105A and S197T, one or more of I161T, N42H, Y120H, and V71M. Mutants that display a shorter elapsed time between emission at a first wavelength and emission at a second wavelength are identified by measuring the spectral shift over time, using methods described above.

Example 5

Use of Timer Proteins to Study Protein Translocation

A construct that includes a promoter that drives transcription of a nucleic acid molecule encoding a fusion protein consisting of a subject fluorescent timer protein fused in-frame to a nuclear localization signal (NLS) is introduced into a eukaryotic cell. Where the timer protein is E5, the fusion protein exhibits green fluorescence soon after it is synthesized. Initially, the fusion protein (and green fluorescence) is cytoplasmic. Over time, the protein enters the nucleus of the cell. Newly synthesized protein in the cytoplasm exhibits green fluorescence. Protein that has moved into the nucleus will shift to red fluorescence. The appearance of red fluorescence in the nucleus is related to the established timing of the spectral shift for E5, e.g., as shown in Examples 2 and 3.

An external agent, such as a test agent, is added to determine the effect, if any, on translocation of the fusion protein to the nucleus. Where the promoter is an inducible promoter, the test agent is added simultaneously with, shortly before (e.g., within an hour) or shortly after, addition of the inducer.

Example 6

Use of a Fluorescent Timer Protein to Study Promoter Shut-Down

A construct that includes a regulatable promoter driving expression of a timer protein is introduced into a eukaryotic cell. Where the timer protein is E5, the protein that is initially synthesized exhibits green fluorescence. An external signal is provided that results in down-regulation, or shut-down, of the promoter. New protein is no longer synthesized. The population of E5 protein that was synthesized before promoter shut down "ages" and undergoes a spectral shift such that it exhibits red fluorescence. The timing of shut-down is followed as an increase of the ratio of red to green fluorescence over time.

It is evident from the examples above that the instant invention provides fluorescent timer proteins that are undergo a spectral shift over time following synthesis. These proteins are particularly useful in applications that cannot be practiced effectively with fluorescent proteins that do not undergo a spectral shift over time. Use of currently available fluorescent proteins that do not undergo a spectral shift over time does not allow one to distinguish between, e.g., a decrease in fluorescence due to shut-down of a promoter and a decrease in fluorescence due to protein degradation. Applications for which the subject timer proteins are particularly suited include methods of monitoring promoter activity (e.g., during development, during cell differentiation, in response to an applied or ingested agent, in response to tissue-specific signals, and the like); methods of tracking movement of a protein, both intracellular movement and intercellular movement; methods of studying cell fate, differentiation, and migration; and methods of assessing protein stability. As such the subject invention represents a significant contribution to the art.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A fluorescent timer protein present in other than its natural environment having an emission spectrum that changes over time after synthesis from a first wavelength to at least a second wavelength, wherein said fluorescent timer protein has a sequence identity of at least 95% with SEQ ID NO:02, and comprises at least one amino acid substitution at a position that corresponds to position 197 in SEQ ID NO:02.

2. The fluorescent timer protein according to claim 1, wherein said fluorescent timer protein comprises amino acid substitutions at positions that correspond to positions 105 and 197 in SEQ ID NO:02.

3. The fluorescent timer protein according to claim 1, wherein said first wavelength is in the range of about 480 to about 520 nm, and the second wavelength is from about 560 to about 600 nm.

4. The fluorescent timer protein according to claim 1, wherein said protein emits at said first wavelength from about six hours to about 24 hours after synthesis, and emits at said second wavelength from about nine hours to about 50 hours after synthesis.

5. The fluorescent timer protein according to claim 1, wherein the ratio of fluorescence intensity at the first wavelength to the fluorescence intensity at the second wavelength is linear over time.

6. The fluorescent timer protein according to claim 1, wherein the protein has the amino acid sequence set forth in SEQ ID NO:04 or SEQ ID NO:06.

7. The fluorescent timer protein according to claim 1, wherein the protein is isolated.

8. A nucleic acid molecule present in other than its natural environment comprising a nucleotide sequence encoding a fluorescent timer protein having an emission spectrum that changes over time after synthesis from a first wavelength to at least a second wavelength, wherein said fluorescent timer protein has a sequence identity of at least 95% with SEQ ID NO:02 and comprises at least one amino acid substitution at a position that corresponds to position 197 in SEQ ID NO:02.

9. The nucleic acid molecule according to claim 8, wherein said nucleic acid molecule encodes a fluorescent timer protein that comprises amino acid substitutions at positions that correspond to positions 105 and 197 in SEQ ID NO:02.

10. A recombinant vector comprising a nucleic acid according to claim 8.

11. The recombinant vector according to claim 10, wherein said vector comprises a transcriptional initiation region functional in an expression host and a transcriptional termination region functional in said expression host wherein the nucleotide sequence encoding said timer protein is under the transcriptional regulation of said transcriptional initiation region.

12. The recombinant vector according to claim 10, further comprising a multiple cloning site 5' of the nucleotide sequence encoding the fluorescent timer protein.

13. The recombinant vector according to claim 12, further comprising a multiple cloning site 3' of the nucleotide sequence encoding the fluorescent timer protein.

14. The recombinant vector according to claim 10, wherein the nucleotide sequence encoding the fluorescent timer protein is operably linked to a regulatory element.

15. A host cell comprising a recombinant vector according to claim 10.

16. A method of producing a protein according to claim 1, said method comprising:
 growing a cell according to claim 15, whereby said protein is expressed; and
 isolating said protein substantially free of other proteins.

17. A method of monitoring the activity of a promoter, comprising:
 a) introducing into a cell a recombinant vector comprising, in order from 5' to 3' and in operable linkage, a promoter and a nucleic acid molecule comprising a nucleotide sequence that encodes a fluorescent timer protein, wherein said fluorescent timer protein has an emission spectrum that changes over time after synthesis from a first wavelength to at least a second wavelength and wherein said fluorescent timer protein has a sequence identity of at least 95% with SEQ ID NO:02, and comprises at least one amino acid substitution at a position that corresponds to position 197 in SEQ ID NO:02;
 b) detecting emission at the first wavelength and at least a second wavelength; and
 c) relating the emission at the second or subsequent wavelength to the activity of the promoter.

18. The method according to claim 17, wherein said fluorescent timer protein comprises amino acid substitutions at positions that correspond to positions 105 and 197 in SEQ ID NO:02.

19. The method according to claim 17, wherein the ratio of fluorescence intensity at the first wavelength to the fluorescence intensity at the second wavelength is linear over time, and wherein said relating step comprises calculating the time elapsed from activation of the promoter based on the ratio of fluorescence intensity at the first wavelength to fluorescence intensity at the second wavelength.

20. The method according to claim 17, wherein the promoter is selected from the group consisting of a developmentally regulated promoter, a cell cycle-regulated promoter, a tissue-specific promoter, a cell type-specific promoter, and an inducible promoter.

21. The method according to claim 17, wherein the activity of the promoter is modulated in response to an external or internal signal.

22. The method according to claim 17, further comprising the steps of contacting the cell with an agent that modulates the activity of the promoter between step a) and step b).

23. A method of determining the age of a protein, comprising
 a) introducing into a cell a recombinant vector comprising, in order from 5' to 3' and in operable linkage, a promoter and a nucleic acid molecule comprising a nucleotide sequence that encodes a fusion protein comprising a protein fused in-frame at its amino- or carboxyl-terminus to a fluorescent timer protein, wherein said fluorescent timer protein has an emission spectrum that changes over time after synthesis from a first wavelength to at least a second wavelength and wherein said fluorescent timer protein has a sequence identity of at least 95% with SEQ ID NO:02, and comprises at least one amino acid substitution at a position that corresponds to position 197 in SEQ ID NO:02;
 b) detecting emission at the first wavelength and at least a second wavelength; and
 c) relating the emission at the second or subsequent wavelength to the age of the protein.

24. The method according to claim 23, wherein said fluorescent timer protein comprises amino acid substitutions at positions that correspond to positions 105 and 197 in SEQ ID NO:02.

25. The method according to claim 23, wherein the protein is translocated from a first region of the cell to at least a second region of the cell, and wherein said detecting step detects the timer protein in the first and second regions of the cell.

26. A method of enriching a population of cells comprising a fluorescent timer protein that emits at a wavelength from a starting population of cells, the method comprising:
 a) introducing into said starting population a construct comprising a regulatory element operably linked to a nucleic acid molecule comprising a nucleotide sequence that encodes a fluorescent timer protein having a sequence identity of at least 95% with SEQ ID NO:02, and comprising at least one amino acid substitution at a position that corresponds to position 197 in SEQ ID NO:02; and
 b) sorting a population of cells in which the timer protein emits at a first wavelength, thereby obtaining a cell population enriched for cells containing timer protein that emits at a first wavelength.

27. The method according to claim 26, wherein said fluorescent timer protein comprises amino acid substitutions at positions that correspond to positions 105 and 197 in SEQ ID NO:02.

28. The method of claim 26, wherein the regulatory element is a cell cycle regulated promoter, and the enriched population is enriched for cells in a phase of the cell cycle in which the cell cycle regulated promoter is active.

29. The method of claim 26, further comprising subjecting the enriched population to a second sorting step, wherein the second sorting step comprises sorting a population for cells containing timer protein that emits at a second wavelength.

30. A method of identifying an agent that modulates the activity of a promoter, comprising:
- a) contacting a cell comprising a nucleic acid molecule that comprises a nucleotide sequence encoding a fluorescent timer protein having a sequence identity of at least 95% with SEQ ID NO:02, and comprising at least one amino acid substitution at a position that corresponds to position 197 in SEQ ID NO:02, said nucleotide sequence operably linked to a promoter, with a test agent; and
- b) determining the effect of the test agent on promoter activity, wherein said determining comprises detecting emission at a first wavelength and at least a second wavelength.

31. The method according to claim 30, wherein said fluorescent timer protein comprises amino acid substitutions at positions that correspond to positions 105 and 197 in SEQ ID NO:02.

32. A kit comprising a recombinant vector according to claim 10.

* * * * *